US009540649B2

(12) United States Patent
Humphries et al.

(10) Patent No.: US 9,540,649 B2
(45) Date of Patent: Jan. 10, 2017

(54) METHOD FOR OPENING TIGHT JUNCTIONS

(75) Inventors: Peter Humphries, Dublin (IE); Matthew Campbell, Dublin (IE); Anna-Sophia Kiang, County Wicklow (IE)

(73) Assignee: The Provost, Fellows and Scholars of the College of the Holy and Undivided Trinity of Queen Elizabeth near Dublin, Dublin (IE)

( * ) Notice: Subject to any disclaimer, the term of this patent is extended or adjusted under 35 U.S.C. 154(b) by 583 days.

(21) Appl. No.: 12/682,331

(22) PCT Filed: Oct. 13, 2008

(86) PCT No.: PCT/EP2008/063734
§ 371 (c)(1),
(2), (4) Date: Nov. 19, 2010

(87) PCT Pub. No.: WO2009/047362
PCT Pub. Date: Apr. 16, 2009

(65) Prior Publication Data
US 2011/0064792 A1    Mar. 17, 2011

(30) Foreign Application Priority Data

Oct. 12, 2007   (EP) ..................................... 07118412
Sep. 12, 2008   (IE) ..................................... 2008/0743

(51) Int. Cl.
C12N 15/11       (2006.01)
C12N 15/113      (2010.01)
C07H 21/04       (2006.01)

(52) U.S. Cl.
CPC ......... *C12N 15/1138* (2013.01); *C12N 15/111* (2013.01); *C12N 2310/14* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| 5,260,210 | A  | * | 11/1993 | Rubin et al.    | 435/325 |
| 6,041,252 | A  | * | 3/2000  | Walker et al.   | 604/20  |
| 6,346,613 | B1 | * | 2/2002  | O'Mahony et al. | 536/24.5|
| 6,514,221 | B2 | * | 2/2003  | Hynynen et al.  | 601/2   |
| 2005/0129679 | A1 | * | 6/2005 | Cui et al.     | 424/130.1 |
| 2008/0113351 | A1 | * | 5/2008 | Naito et al.   | 435/6   |
| 2010/0196393 | A1 | * | 8/2010 | Banks et al.   | 424/152.1 |

FOREIGN PATENT DOCUMENTS

| JP | 2001-517436   | 10/2001 |
| WO | 99/15649 A2   | 4/1999  |
| WO | 2005/058362 A2| 6/2005  |

OTHER PUBLICATIONS

Stamatovic et al., Protein kinase C-alpha-RhoA cross-talk in CCL2-induced alterations in brain endothelial permeability, 2006, The Journal of Biological Chemistry, vol. 281, pp. 8379-8388.*
Mark A. Behlke, Progress towards in vivo use of siRNAs, 2006, Molecular Therapy, vol. 13, pp. 644-670.*
Shlosberg et al., Blood-brain barrier breakdown as a therapeutic target in traumatic brain injury, 2010, Nature Reviews Neurology, vol. 6, pp. 393-403.*
Harutjunyan et al., Efficiency of 7.2% hypertonic saline hydroxyethyl starch 200/0.5 versus mannitol 15% in the treatment of increased intracranial pressure in neurosurgical patients—a randomized clinical trial [ISRCTN62699180], 2005, Critical Care, vol. 9, R530-R540.*
Habgood et al., Changes in blood-brain barrier permeability to large and small molecules following brain injury in mice, 2007, European Journal of Neuroscience, vol. 25, pp. 231-238.*
Vyas, et al., "Formulation and physiological factors influencing CNS delivery upon intranasal administration", Critical Reviews in Therapeutic Drug Carrier Systems, Begell House Publishing Inc., vol. 23, No. 4, Jan. 1, 2006, pp. 319-347.
Kisan, et al., "Nasal drug delivery system-factors affecting and applications", Current Drug Therapy, vol. 2, Jan. 2007, pp. 27-38.
Nitta, et al., "Size-selective loosening of the blood-brain barrier in claudin-5 deficient mice", Journal of Cell Biology, vol. 161, 2003, pp. 653-660.
Miller G., "Breaking down barriers", Science, vol. 297, Aug. 16, 2002, pp. 1116-1119.
Kniesel, et al., "Tight junction of the Blood-Brain Barrier", Cellular and Molecular Neurobiology, vol. 20, No. 1, 2000, pp. 57-76.
Fontijn, et al., "Limited contribution of claudin-5-dependent tight junction strands to endothelial barrier function", European Journal of Cell Biology, Wissenschafliche Verlagsgesellschaft, Stuttgart, DE, vol. 85, No. 11, Nov. 3, 2006, pp. 1131-1144.
Koto, et al., "Hypoxia disrupts the barrier function of neural blood vessels through changes in the expression of Claudin-5 in endothelial cells", American Journal of Pathology, vol. 170, No. 4, Apr. 2007, pp. 1389-1397.
Johnson, et al., "Exploiting tight junctions for the delivery of drugs", Genetic Engineering News, Mary Ann Liebert, New York, NY, US, vol. 24, No. 1, Jan. 1, 2004, p. 34.
McCarty J. H., "Cell biology of the neurovascular unit: implications for drug delivery across the blood-brain barrier", Assay and Drug Development Technologies, vol. 3, No. 1, 2005, pp. 89-95.

(Continued)

*Primary Examiner* — Dana Shin
(74) *Attorney, Agent, or Firm* — VLP Law Group LLP; Richard G. A. Bone

(57) ABSTRACT

The present invention is directed to a method and use of RNA interference (RNAi) for the transient, reversible and controlled opening of the tight junctions of the blood brain barrier and/or the blood retinal barrier. This method may be used in the treatment of many diseases and disorders which require the opening of the blood brain barrier and/or blood retinal barrier. Such methods generally involve the use of an RNAi-inducing agent, such as siRNA, miRNA, shRNA or an RNAi-inducing vector whose presence within a cell results in production of an siRNA or shRNA, targeting tight junction proteins to open the blood brain barrier and/or blood retinal barrier.

10 Claims, 42 Drawing Sheets

(56) References Cited

OTHER PUBLICATIONS

Figure 1A:
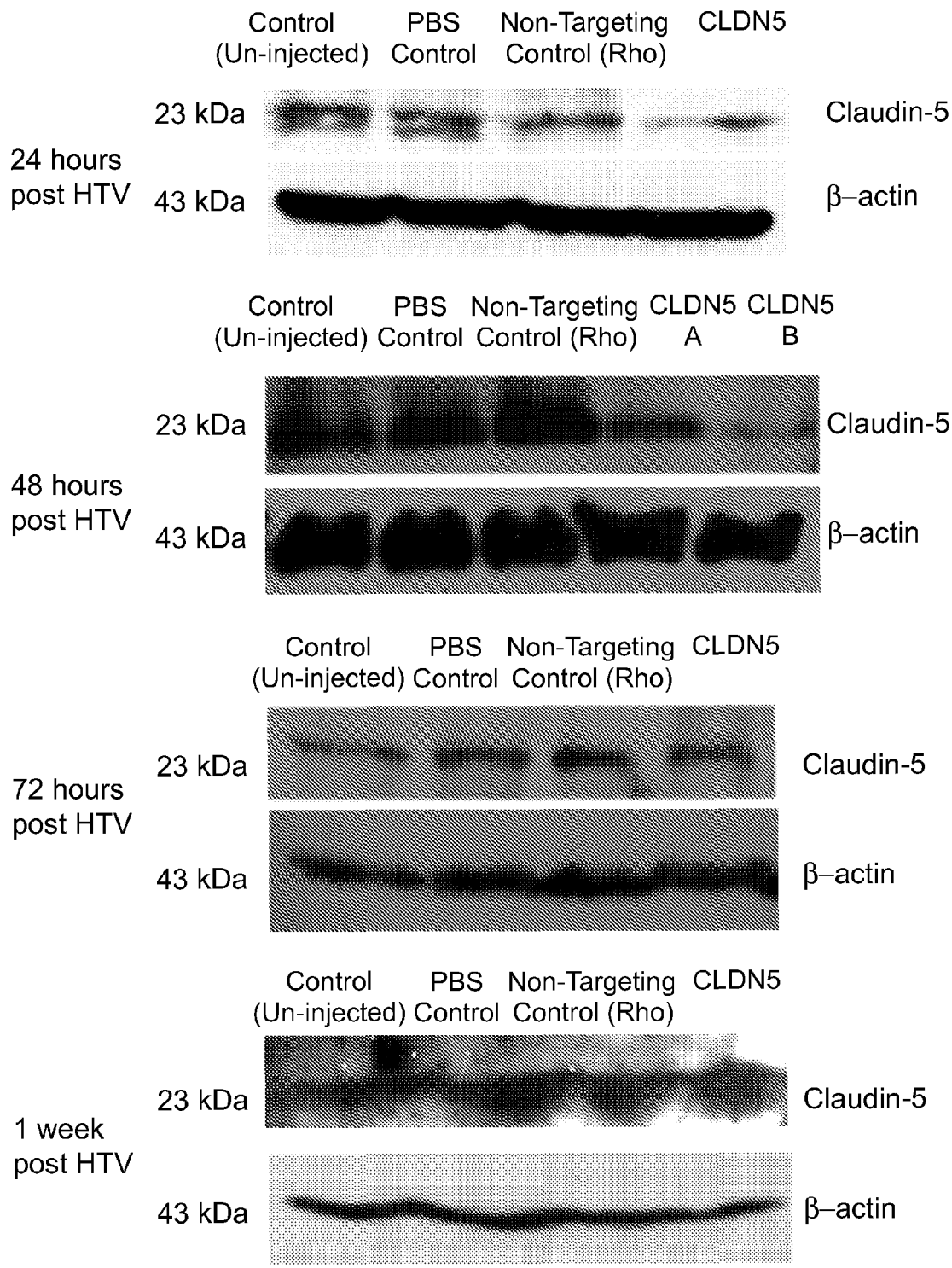

Salama, et al., "Tight junction modulation and its relationship to drug delivery", Advanced Drug Delivery Reviews, vol. 58, 2006, pp. 15-28.
Campbell, et al., "RNAi-mediated reversible opening of the blood-brain barrier", The Journal of Gene Medicine, vol. 10, May 28, 2008, pp. 930-947.
Phillips, et al., "Occludin independently regulates permeability under hydrostatic pressure and cell division in retinal pigment epithelial cells", Investigative Ophthalmology & Visual Science, vol. 49, No. 6, 2008, pp. 2568-2576.
International Search Report received for PCT Patent Application No. PCT/EP2008/063734, mailed on Jul. 22, 2009, 7 pages.
Written Opinion received for PCT Patent Application No. PCT/EP2008/063734, mailed on Jul. 22, 2009, 11 pages.
Anderson, J. M. (2001). "Molecular structure of tight junctions and their role in epithelial transport." News Physiol Sci 16: 126-30.
Bazzoni, G. (2006). "Endothelial tight junctions: permeable barriers of the vessel wall." Thromb Haemost 95(1): 36-42.
Bickel, U., et al. (2001). "Delivery of peptides and proteins through the blood-brain barrier." Adv Drug Deliv Rev 46(1-3): 247-79.
Edwards, R. H. (2001). "Drug delivery via the blood-brain barrier." Nat Neurosci 4(3): 221-2.
Fanning, A. S. and J. M. Anderson (1999). "PDZ domains: fundamental building blocks in the organization of protein complexes at the plasma membrane." J. Clin. Invest. 103(6): 767.
Furuse, M., et al. (1998). "A Single Gene Product, Claudin-1 or -2, Reconstitutes Tight Junction Strands and Recruits Occludin in Fibroblasts." J Cell Biol 143(2): 391-401.
Herweijer, H. and J. A. Wolff (2007). "Gene therapy progress and prospects: hydrodynamic gene delivery." Gene Ther 14(2): 99-107.
Hino, T., et al. (2006). "In vivo delivery of small interfering RNA targeting brain capillary endothelial cells." Biochem. Biophys. Res. Commun. 340(1): 263-7.
Inai, T., et al. (1999). "Claudin-1 contributes to the epithelial barrier function in MDCK cells." Eur J Cell Biol 78(12): 849-55.
Kausalya, P. J., et al. (2001). "Connexin45 directly binds to ZO-1 and localizes to the tight junction region in epithelial MDCK cells." FEBS Lett 505(1): 92-96.
Kiang, A.-S., et al. (2005). "Toward a Gene Therapy for Dominant Disease: Validation of an RNA Interference-based Mutation-independent Approach." Mol Ther 12(3): 555-61.
Koto, T., et al. (2007). "Hypoxia disrupts the barrier function of neural blood vessels through changes in the expression of claudin-5 in endothelial cells." Am J Pathol 170(4): 1389-97.
Lewis, D. L., et al. (2002). "Efficient delivery of siRNA for inhibition of gene expression in postnatal mice." Nat Genet 32(1): 107-8.
Matter, K. and M. S. Balda (2003). "Holey barrier: claudins and the regulation of brain endothelial permeability." J Cell Biol 161(3): 459-60.
McCaffrey, A. R, et al. (2002). "RNA interference in adult mice." Nature 418(6893): 38-9.
Miller, G. (2002). "Drug targeting. Breaking down barriers." Science 297(5584): 1116-8.
Palfi, A., et al. (2006). "RNAi-Based Suppression and Replacement of rds-Peripherin in Retinal Organotypic Culture." Hum Mutat 27(3): 260-8.
Pardridge, W. M. (2005). "Molecular biology of the blood-brain barrier." Mol Biotechnol 30(1): 57-70.
Pardridge, W. M. (2006). "Molecular Trojan horses for blood-brain barrier drug delivery." Curr Opin Pharmacol 6(5): 494-500.
Reese, T. S. and M. J. Karnovsky (1967). "Fine structural localization of a blood-brain barrier to exogenous peroxidase." J Cell Biol 34(1): 207-17.
Reynolds, A., et al. (2004). "Rational siRNA design for RNA interference." Nat Biotechnol 22(3): 326-30.
Schlageter, K. E., et al. (1999). "Microvessel Organization and Structure in Experimental Brain Tumors: Microvessel Populations with Distinctive Structural and Functional Properties." Microvasc Res 58(3): 312-28.
Spencer, B. J. and I. M. Verma (2007). "Targeted delivery of proteins across the blood-brain barrier." Proc Natl Acad Sci U S A 104(18): 7594-9.
Tsukita, S., et al. (2001). "Multifunctional strands in tight junctions." Nat Rev Mol Cell Biol 2(4): 285-93.
Turksen, K. and T. C. Troy (2004). "Barriers built on claudins." J Cell Sci 117(Pt 12): 2435-47.
Wolburg, H. and A. Lippoldt (2002). "Tight junctions of the blood-brain barrier: development, composition and regulation." Vascul Pharmacol 38(6): 323-37.
Zahraoui, A., et al. (2000). "Tight junction, a platform for trafficking and signaling protein complexes." J Cell Biol 151(5): F31-6.
Stachler MD, Bartlett JS. Mosaic vectors comprised of modified AAV1 capsid proteins for efficient vector purification and targeting to vascular endothelial cells. Gene Therapy. Jun. 2006; 13(11):926-31.
Work LM, Büning H, Hunt E, Nicklin SA, Denby L, Britton N, Leike K, Odenthal M, Drebber U, Hallek M, Baker AH. "Vascular bed-targeted in vivo gene delivery using tropism-modified adeno-associated viruses." Molecular Therapy. Apr. 2006; 13(4):683-93. Epub Jan. 4, 2006.
Campbell, et al., "Targeted suppression of claudin-5 decreases cerebral oedema and improves cognitive outcome following traumatic brain injury," Nature Communications, 3:849, May 22, 2012, pp. 1-12.
Baskaya, et al., "The biphasic opening of the blood-brain barrier in the cortex and hippocampus after traumatic brain injury in rats," Neuroscience Letters, 226, Mar. 19, 1997, pp. 33-36.
Hall et al., "Osmotic blood-brain barrier disruption chemotherapy for diffuse pontine gliomas", Journal of Neuro-Oncology (2006) 77: 279-284.
Wise, et al. The value of hypertonic mannitol solution in decreasing brain mass and lowering cerebro-spinal-fluid pressure, J Neurosurg. Dec. 1962;19:1038-43.
Documents from examination of European Patent Application No. 08837274.3: examination report of Jun. 3, 2014; reply to Examination report on Sep. 17, 2014; approved claims for grant, and notice of intent to grant, dated Dec. 17, 2014; and decision to grant, dated May 8, 2015.
Abbott et al., "Astrocyte-endothelial interactions at the blood-brain barrier," Nat. Rev., 2006, vol. 7, pp. 41-53.
Su et al., "Drug Delivery across the blood-brain barrier:why is it difficult? how to measure and improve it?" Expert Opin. Drug Deliv., 2006, vol. 3, No. 3, pp. 419-435.
Peracchi, A., "Prospects for antiviral ribozymes and deoxyribozymes," Rev. Med. Virol., 2004, vol. 14, pp. 47-64.
Examination report dated Sep. 3, 2013 in JP application No. 2010-528430.

\* cited by examiner

Claudin-5 and Claudin-1 immunohistochemistry 48 hours post hydrodynamic tail vein delivery of CLDN5 siRNA Claudin-5 and Claudin-1 immunohistochemistry 1 week post hydrodynamic tail vein delivery of CLDN5 siRNA

Figure 7A:
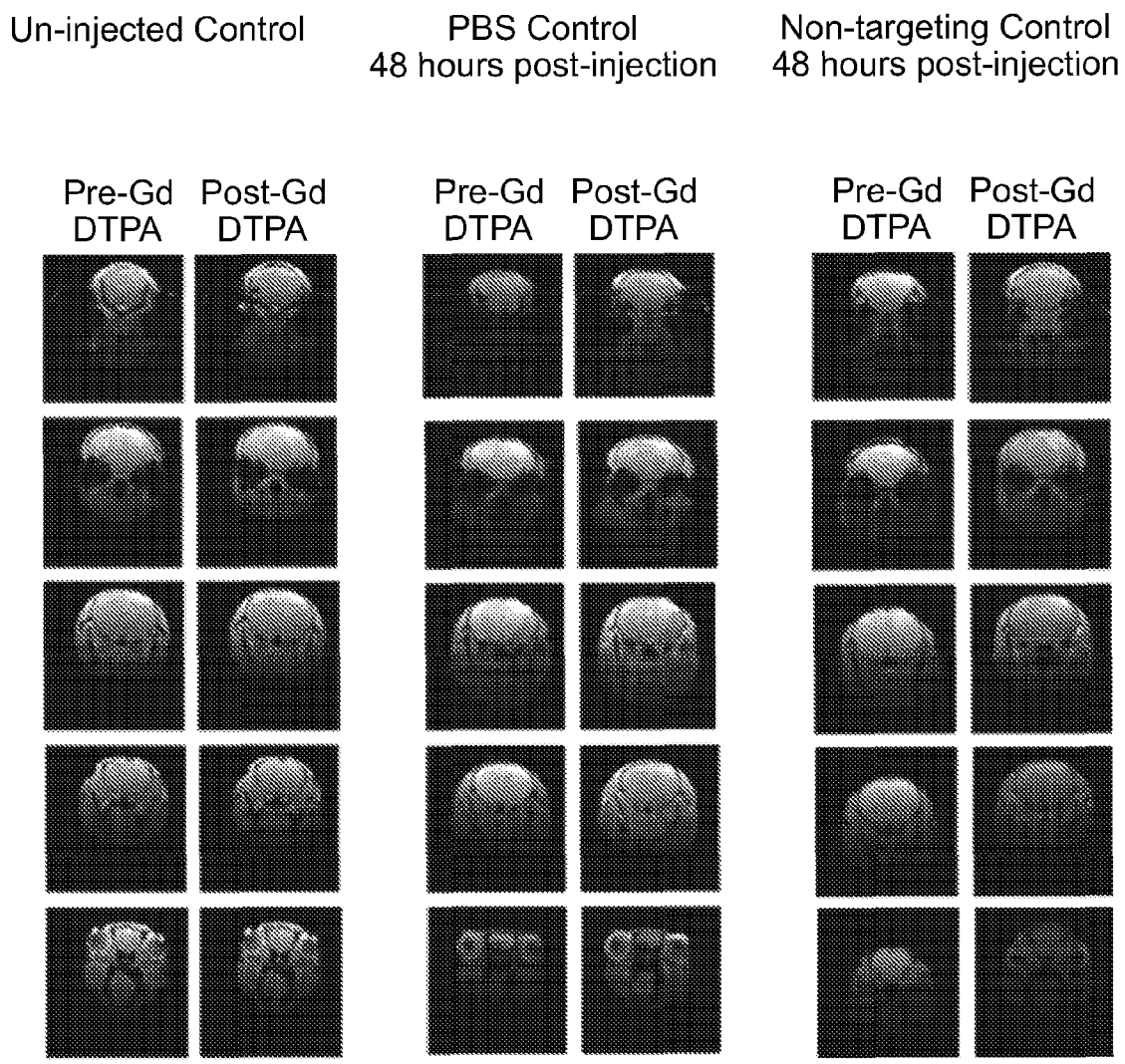

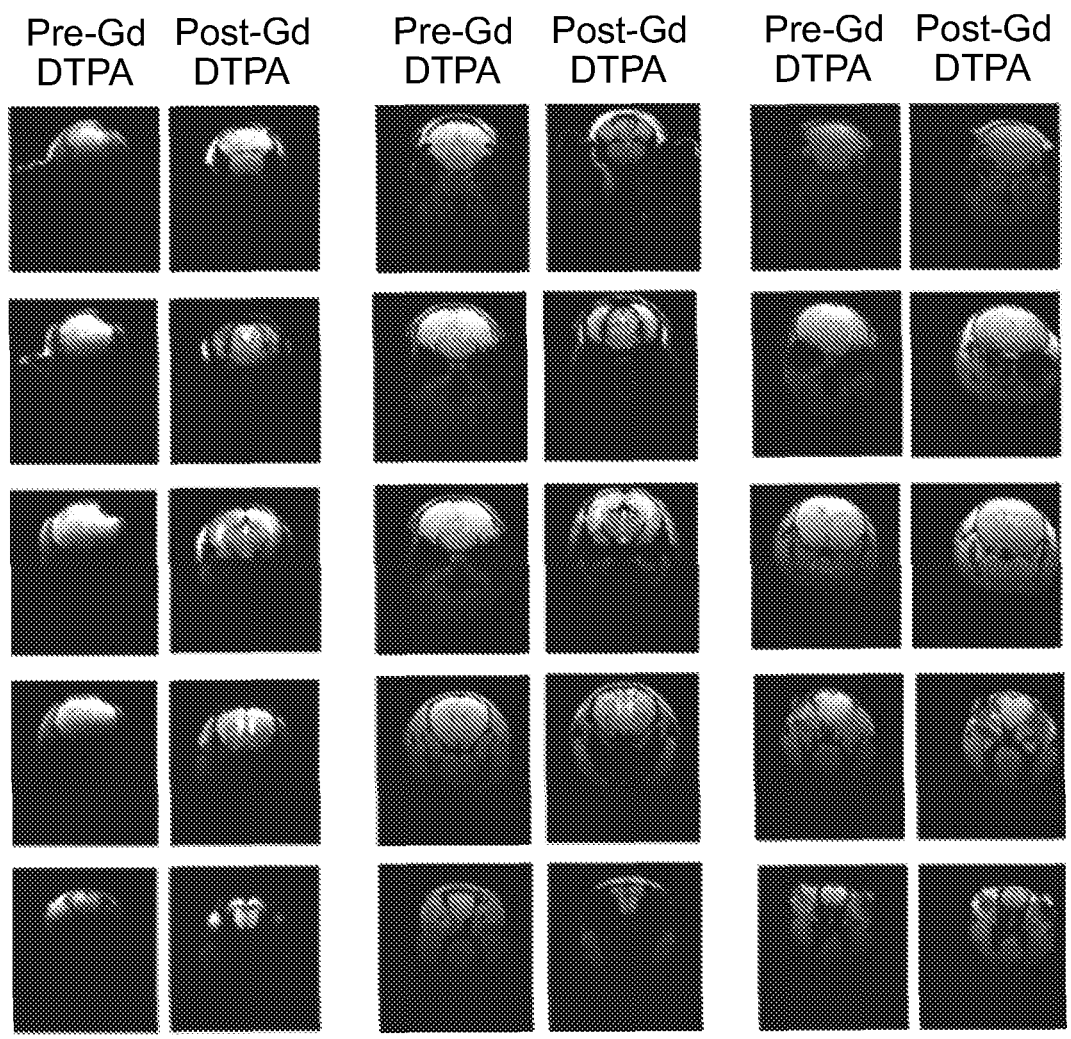
Figure 7A (Contd.)

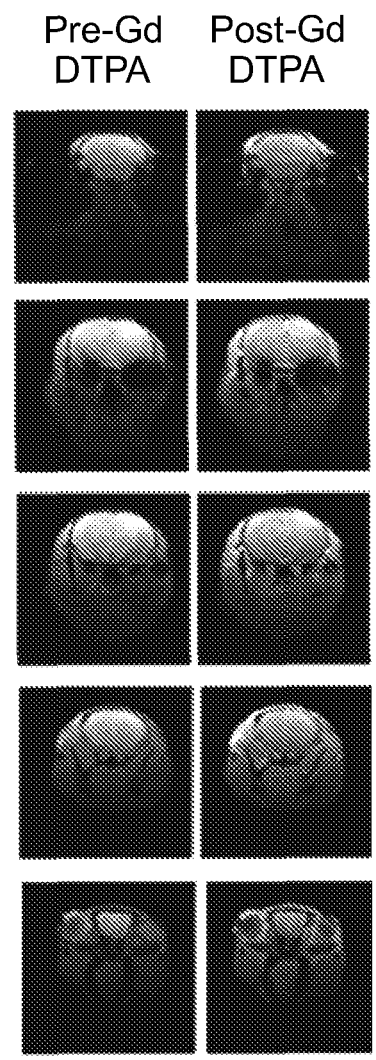
Figure 7A (Contd.)

Immunohistochemical analysis of claudin-5 levels in retinal flatmounts

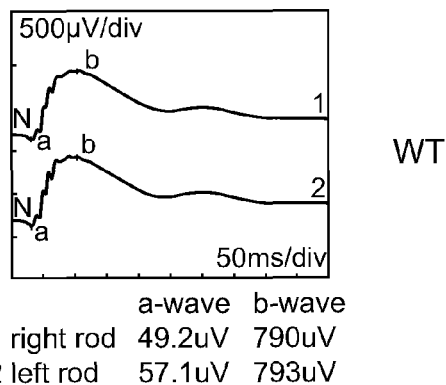
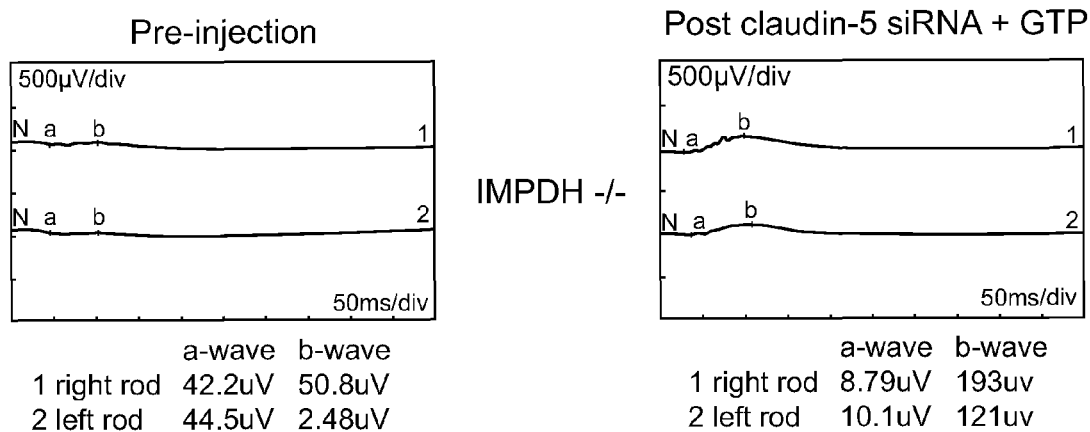
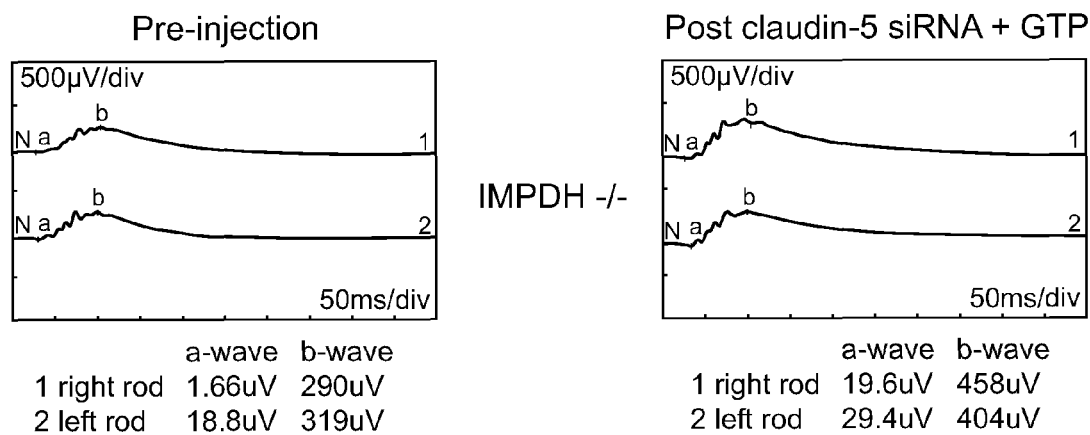
Figure 18

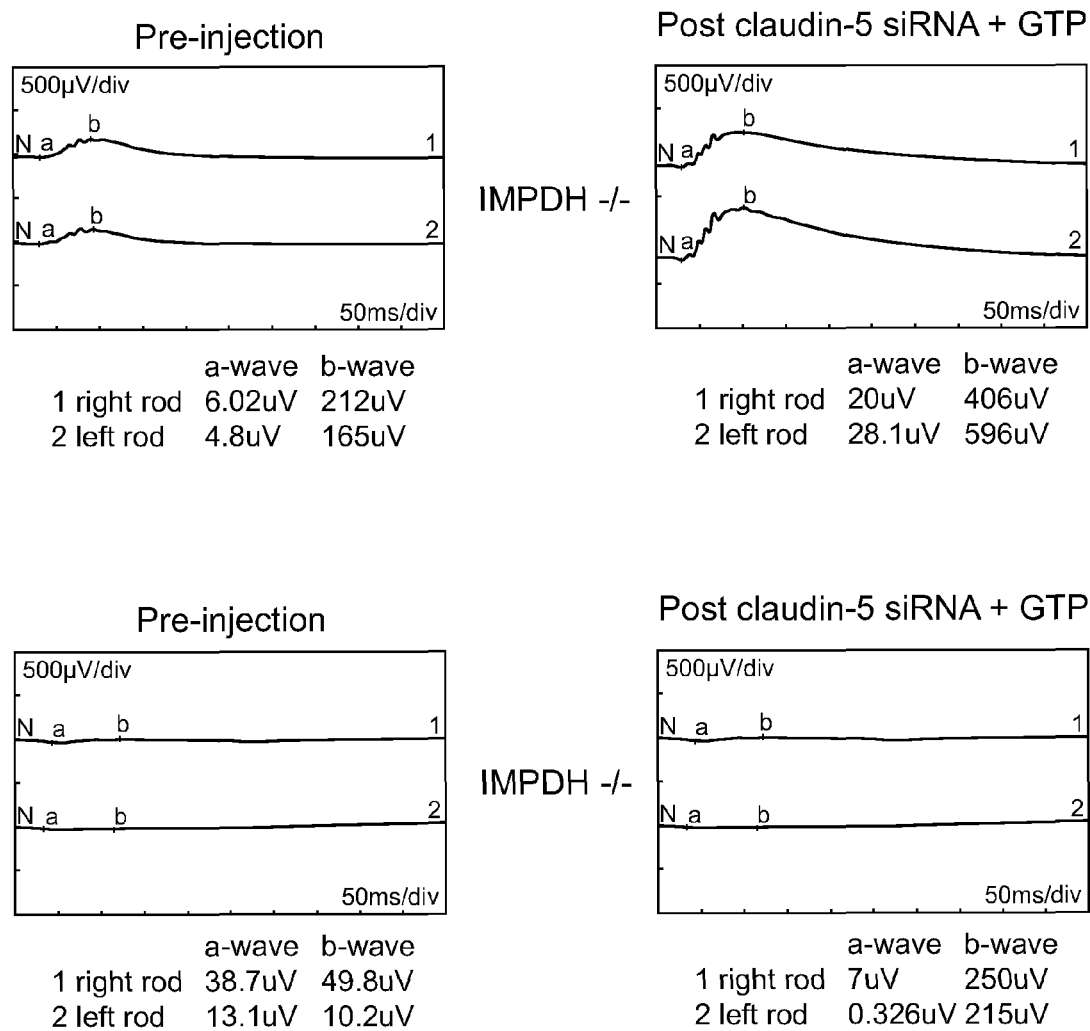
Figure 18 (Contd.)

Albumin IHC following occludin siRNA injection 24 hours post HTV

IgG and Hoechst staining following Occludin siRNA injection 24 hours post HTV

Target sequence in Claudin-5 mRNA (SEQ ID NO: 43)
AACGTTGGAAATTCTGGGTCT siRNA Anti-sense sequence (SEQ ID No.2)
5'-AGACCCAGAAUUUCCAACGUU-3'

Mus musculus claudin 5 mRNA: (SEQ ID NO: 23)

```
AGTTGGTGTAGTTAAAACCTCCTCTTCTGCTCCAGGACTGGAGGCTCCAGAGCAGAGGCACCAGAACCAA
TTCCCAGCTCCCAGCCTAAGCAGCGCAGAGAGCACCCGGAGGCCCCAAGGGCCGTCGGGTGAGCATTCAG
TCTTTAGCCATGGGGTCTGCAGCGTTGGAAATTCTGGGTCTGGTGCTGTGTCTGGTAGGATGGGTGGGCT
TGATCCTGGCGTGTGGCTGCCCATGTGGCAGGTGACTGCCTTCCTGCACCACAACATCGTGACGGCGCA
GACGACTTGGAAGGGGCTGTGGATGTCGTGCGTGGTGCAGAGTACCGGGCACATCCAGTGCAACCTGTAT
GAATCTGTGCTGGCGCTGAGTGCGGAGGTGCAGGCAGCTCGGGCACTCACCGTGGGCGCTGTGCTGCTGG
CGCTGGTGGCACTCTTTGTTACCTTGACCGGCGCTCAGTGCACCACCTGCGTGGCCCCGGGCCCAGTTAA
GGCACGGGTAGCACTCACGGGAGGAGCGCTTTACCGCGTGTGCGGGCTGCTGGCACTCGTGCCGCTCTGC
TGGTTCGCCAACATCGTTGTCCGCGAGTTCTATGATCCGACGCTGCCGGTGTCACAGAAGTACGAGCTGG
GCGCGGCGCTGTACATCGGCTGGGCGGCCTCCGCACTGCTCATGTGCGGTGGCGGCCTCGTGTGTTGCGG
CGCCTGGGTCTCACCGGGCGCCCTGAGTTCAGCTTCCCGGTCAAGTACTCAGCGCCGCGGCGGCCCACGG
CCAATGGCGATTACGACAAGAAGAACTATGTCTAAGGGCGGGAGGCATGGCGGGGCTCTTCCCGCAGCTA
AGCCCGCGATGGGAAAGACCGATGCGGGAAGCCGTGTGTGGATGACGACCACCGCTGGGTTGCGCAGCGC
AAGTCATGCTGGGTTCGGGCCAGACTTGCCCGCTCTCAGAGTCCGTTGACCATCACTAGCCGGGCCCTGC
TCAGAACAGACTACAGGCACTTTTAAGAACTTGACCGACCTTTTCTTCTATGCGCAGTTGGCCACGACGT
GGGTGGAACGCTCAGATTTCATCGGTGAAGTAGGCACCAAACTGCCGCGAACAGTTCCTACTGAGATCCT
GGGGCACTACATGCTGCCTTAATGTCCAGTGGCACCTGCTAACCTGAAAGGGCAGCTGGAGAAACCCCG
GGGCTGCCAGAGGGACGTGTTAAAAAGGGCATTTTCTTTGTTAGTGGAGAAGAACCTACTGAACCAAAGG
ACTTAGCCTGGACCTGGTCTCACTCCAGCACTCCCCAAGGTGGGGCCCTGTAGGTACCAGAGCCTTAG
AGGGGTTGCCTTCCTCCTGGAAGCTTGGGGCTTGGGGGTGGGCCGGGCAAGAATTTGCTCAGTAAATGG
TTTGAACACTTTC
```

Figure 25

Claudin-12 immunohistochemistry 48 hours post hydordynamic injection of siRNA targeting claudin-12

Hoechst and FD-4 perfusion 48 hours post hydrodynamic tail vein injection of siRNA targeting claudin-12

METHOD FOR OPENING TIGHT
> JUNCTIONS

INTRODUCTION

The present invention is directed to a method and use of RNA interference (RNAi), using RNAi inducing agents, such as siRNA, miRNA, shRNA or an RNAi-inducing vector whose presence within a cell results in production of an siRNA or shRNA, targeting tight junction proteins, for the transient, reversible and controlled opening of the tight junctions of the blood brain barrier and/or the blood retinal barrier.

The brain is an energy-demanding organ requiring nutrients and oxygen, while at the same time, needing protection from other potentially harmful agents, for example, viral or bacterial particles, or anaphylatoxins (potentially destructive particles generated as a by-product of the immune system), which may be delivered by the circulation to this sensitive tissue. For this reason, those cells which line the walls of the fine capillaries that supply blood to the brain (the blood-brain barrier (BBB)) have evolved 'tight junctions', which, as the name implies, reduce the space between adjacent endothelial cells lining the fine capillaries of the microvasculature of the brain to virtually zero, forming a tight seal. However, oxygen can still diffuse from these cells, and other essential materials can be delivered to the brain by special transporters located in the membranes of the endothelial cells.

Many attempts have been made either to break the blood brain barrier or to design delivery systems that enable pharmacological agents to traverse the endothelial cells of brain capillaries (Pardridge et al., 2005). However, complete breakdown of the blood-brain barrier would have disastrous consequences for brain function. Previous attempts have been made without a comprehensive understanding of the structure of the tight junctions (TJ's), without technologies capable of ablating transcripts encoding TJ proteins and without a means of systemic delivery of such agents to the endothelial cells of brain or retinal capillaries (Miller, 2002).

Recently, genetically engineered proteins termed "Molecular Trojan horses" have been described and purportedly cross the BBB via endogenous receptor-mediated transport processes (Pardridge et al., 2006). In 2007, using a modified yet similar approach, targeted delivery of proteins across the BBB was reported using a lentivirus vector system, exploiting the binding domain of apolipoprotein B to its receptor "low-density lipoprotein receptor" (LDLR). This report proved feasible for the delivery of proteins via the transcellular pathway, yet these approaches have yet to address peptide cleavage from the engineered binding sites upon delivery to the CNS (Spencer B J and Verma M, 2007). Transcellular, receptor-mediated, delivery of molecules across the BBB remains an exciting avenue for further research, however, there are other routes including the paracellular pathway which may be utilised.

In general, transport of components across endothelial cells of the BBB can occur via three routes: a transcellular route, which may be mediated via special transporters as alluded to above, vesicular transport, or a paracellular route which allows for transport between neighbouring endothelial cells (Reese and Karnovsky, 1967; Edwards, 2001; Wolburg and Lippoldt, 2002). Brain capillaries exhibit very low rates of fluid phase transcytosis, and the paracellular route between individual cells at the BBB is sealed by TJs that are considerably tighter than in any other microvessels in the body. Therefore, TJs represent a key factor in the low permeability properties associated with the BBB (Matter K and Balda M S, 2003).

The TJ's associated with the BBB are composed of a complex of intracellular and transmembrane proteins including occludin, junctional adhesion molecule (JAM), claudins-1, -5, -12 and ZO-1, -2 and -3 (Fanning et al., 1998; Zahraoui et al., 2000).

Claudins play an essential role in BBB function. Approximately 20 members of the claudin family have also been described, claudins 1, -5 and -12 predominating in TJ's of the BBB (Bazzoni, 2006). Claudins, like occludin, span endothelial cell membranes four times and interact with ZO-1 via their C-terminus (Kausalya et al., 2001). Co-expression of occludin and claudin-1 in fibroblasts has been shown to result in co-localization of both proteins at the periphery of the cells in TJ-like strands (Furuse et al., 1998). Claudin-1 over-expression in Madin-Darby canine kidney (MDCK) cells increases Trans-cellular electrical resistance (TER) and has been shown to reduce fluorescein isothiocyanate (FITC)-dextran flux across the monolayer (Inai et al., 1999).

WO 02/014499 (Immunex) is directed to new members of the claudin family, claudin-19, -21 and -22. This application concerns the generation of polypeptide fragments targeting extracellular binding domains of these claudins, while also describing the production of recombinant protein.

Claudin-5 is a four trans-membrane protein, which when knocked out in the mouse causes a size-selective loosening of the BBB to molecules of less than 800 Da. Claudin-5 is considered to be endothelial cell-specific (Turksen K and Troy T C, 2004). Claudin 5−/− mice have been reported and the BBB is compromised in these animals. Through a series of tracer molecule experiments and Magnetic Resonance Imaging (MRI), it was found that while removal of claudin-5 compromises the function of the barrier by allowing it to become permeable to molecules of up to approximately 800 Da, the barrier can form, remaining intact and impervious to larger molecules, showing no evidence of bleeding or oedema (Nitta et al., 2003). However, these knockout mice had very high mortality rates and only survived for a few hours. As such, these knockout mice cannot be used to study the physiology of the BBB and alternative models are needed.

Other systems have been developed to open tight junctions to enhance mucosal paracellular transport. For example, WO 04/003145 (Nastech) and WO 05/058362 (Nastech) both address the need to provide an alternative administration route to injection whilst maintaining the required bioavailability of an active ingredient. WO 04/003145 (Nastech) is directed to the mucosal delivery of biologically active agents, permeabilising agents targeting claudin-5 which can reversibly enhance mucosal paracellular transport. These permeabilising agents are peptides directed against extracellular binding domains of claudin-5 which mediate homotypic interaction of this protein with a similar protein on an adjacent cell. WO 05/058362 (Nastech) is directed to a method for the opening tight junctions in the nose which also comprises the mucosal administration of a wide variety of antagonists to JAM1, Claudin-4 and occludins.

However, despite these advances, many drugs are still ineffective because they are unable to cross the BBB. Thus, much effort has been directed toward understanding the TJs of brain capillary endothelial cells and retinal cells in order to identify molecular mechanisms that could be manipulated to enhance drug delivery across the BBB.

The controlled opening of the BBB, if achieved, would provide an avenue for the experimental delivery of agents to the brain which was not possible previously and could open the door to the treatment of many conditions which involve the blood brain barrier and/or the blood retinal barrier.

Furthermore, the controlled opening of the BBB could enable the establishment of experimental animal models of neurodegenerative and neuropsychiatric disorders and also pave the way for controlled delivery of therapeutic agents in a range of conditions that currently have little or no prospect of effective treatment, for example, agents that modulate neuronal function to the CNS in a range of neurodegenerative conditions.

The present invention is directed to addressing at least some of these problems.

STATEMENT OF THE INVENTION

According to a first general aspect of the invention, there is provided a method for the transient, reversible and size-selective opening of the blood brain barrier wherein the method comprises the use of RNA interference (RNAi) for the transient, reversible and controlled opening of the tight junctions of the blood brain barrier and/or the blood retinal barrier.

The silencing effect of complementary double stranded RNA was first observed in 1990 in petunias by Richard Joergensen and termed co-suppression. RNA silencing was subsequently identified in *C. elegans* by Andrew Fire and colleagues, who coined the term RNA interference (RNAi). This gene silencing phenomenon was later found to be highly conserved in many eukaryotic cells. Thus, RNAi has been shown to be effective in both mammalian cells and animals.

An important feature of RNAi affected by siRNA is the double stranded nature of the RNA and the absence of large overhanging pieces of single stranded RNA, although dsRNA with small overhangs and with intervening loops of RNA has been shown to effect suppression of a target gene. In this specification, it will be understood that in this specification the terms siRNA and RNAi are interchangeable. Furthermore, as is well-known in this field RNAi technology may be effected by siRNA, miRNA or shRNA or other RNAi inducing agents. Although siRNA will be referred to in general in the specification. It will be understood that any other RNA inducing agent may be used, including shRNA, miRNA or an RNAi-inducing vector whose presence within a cell results in production of an siRNA or shRNA targeted to a target transcript.

RNA interference is a multistep process and is generally activated by double-stranded RNA (dsRNA) that is homologous in sequence to the target gene. Introduction of long dsRNA into the cells of organisms leads to the sequence-specific degradation of homologous gene transcripts. The long dsRNA molecules are metabolized to small (e.g., 21-23 nucleotide (nt)) interfering RNAs (siRNAs) by the action of an endogenous ribonuclease known as Dicer. The siRNA molecules bind to a protein complex, termed RNA-induced silencing complex (RISC), which contains a helicase activity and an endonuclease activity. The helicase activity unwinds the two strands of RNA molecules, allowing the antisense strand to bind to the targeted RNA molecule. The endonuclease activity hydrolyzes the target RNA at the site where the antisense strand is bound. Therefore, RNAi is an antisense mechanism of action, as a single stranded (ssRNA) RNA molecule binds to the target RNA molecule and recruits a ribonuclease that degrades the target RNA.

An "RNAi-inducing agent" or "RNAi molecule" is used in the invention and includes for example, siRNA, miRNA or shRNA targeted to a target transcript or an RNAi-inducing vector whose presence within a cell results in production of an siRNA or shRNA targeted to a target transcript. Such siRNA or shRNA comprises a portion of RNA that is complementary to a region of the target transcript. Essentially, the "RNAi-inducing agent" or "RNAi molecule" downregulates expression of the targeted tight junction proteins via RNA interference.

Preferably, siRNA, miRNA or shRNA targeting tight junction proteins are used.

Specifically, the method involves the delivery of an effective amount of siRNA or shRNA targeting tight junction proteins to the subject. It will be understood that an effective amount of the RNAi-inducing agent, such as siRNA, is used to open the BBB to allow the passage of the active agent treating the disorder of interest. Preferably, delivery is via a systemic route.

According to this aspect of the invention, the method results in the reversible and transient RNAi-mediated suppression of the blood brain barrier tight junction protein transcripts in brain capillary endothelial and/or retinal endothelial cells to allow the permeation of molecules, ideally less than 15 kDa, across the blood brain barrier, through the brain capillary endothelial and/or retinal endothelial cells. Opening the blood barrier to this extent will allow siRNAs which typically have a maximum molecular weight of approximately 10-15 kDA, preferably 13 kDa, and/or low molecular weight drugs which generally have a molecular weight less than approximately 2 kDA, preferably approximately 1 kDa or less, to cross the blood brain barrier. It will of course be understood that the blood brain barrier may be opened to allow molecules with a molecular weight greater than 15 kDa to cross the blood brain barrier.

Ideally, the method involves the systemic hydrodynamic delivery of the RNAi inducing agent, such as siRNA, miRNA or shRNA etc, to the subject. Although, non-hydrodynamic systemic delivery methods may be used.

Other delivery methods suitable for the delivery of the RNAi inducing agent (including siRNA, shRNA and miRNA etc) may also be used. For example, some delivery agents for the RNAi-inducing agents are selected from the following non-limiting group of cationic polymers, modified cationic polymers, peptide molecular transporters, lipids, liposomes and/or non-cationic polymers. Viral vector delivery systems may also be used. For example, an alternative delivery route includes the direct delivery of RNAi inducing agents (including siRNA, shRNA and miRNA) and even anti-sense RNA (asRNA) in gene constructs followed by the transformation of cells with the resulting recombinant DNA molecules. This results in the transcription of the gene constructs encoding the RNAi inducing agent, such as siRNA, shRNA and miRNA, or even asRNA and provides for the transient and stable expression of the RNAi inducing agent in cells and organisms. For example, such an alternative delivery route may involve the use of a lentiviral vector comprising a nucleotide sequence encoding a siRNA (or shRNA) which targets the tight junction proteins. Such a lentiviral vector may be comprised within a viral particle. Adeno-associated viruses (AAV) may also be used and the use of these as delivery vehicles is expanded on later.

According to a second aspect of the present invention, the delivery of an RNAi inducing agent, preferably siRNA, miRNA or shRNA etc, according to the invention may be useful in the generation of an experimental model for studying the action of the paracellular pathway, the physiology of the BBB and testing the effect of drugs which cross the BBB and may previously not have been able to cross the BBB.

According to a third aspect of this invention, the present invention is applicable for the treatment of many diseases or disorders where the blood brain barrier or blood retinal barrier is implicated.

According to a fourth aspect of this invention, there is provided a pharmaceutical composition, preferably adapted for systemic delivery, comprising an RNAi inducing agent, preferably siRNA, miRNA or shRNA etc, targeting tight junction proteins to result in the reversible, transient and controlled size selective opening of the paracellular pathway of the blood brain barrier and an active agent for the treatment of a defined disease or disorder. Ideally, the active agent is a biologically active, therapeutic agent.

DETAILED DESCRIPTION

In this specification, the term "blood brain barrier" or BBB has been used to cover both the blood brain barrier (BBB) and the blood retinal barrier (BRB). As expanded on above, the blood-brain barrier (BBB) contains tight junctions (TJ's) which reduce the space between adjacent endothelial cells lining the fine capillaries of the microvasculature of the brain to virtually zero to enable the transport of nutrients and oxygen across the BBB, while at the same time, preventing the transport of other potentially harmful agents across the BBB. The blood-retinal barrier (BRB) is part of the blood-ocular barrier that consists of cells that are joined tightly together in order to prevent certain substances from entering the tissue of the retina. The blood retinal barrier has two components, the retinal vascular endothelium and the retinal pigment epithelium, which also have tight junctions (TJ's). Retinal blood vessels, which are similar to cerebral blood vessels, maintain the inner blood-ocular barrier.

Additionally, the invention disclosed in the present specification relates to the use of RNAi techniques in general. Ideally, an RNAi-inducing agent is used including siRNA, miRNA or shRNA targeted to a target transcript, or an RNAi-inducing vector whose presence within a cell results in production of an siRNA or shRNA targeted to a target transcript. Such siRNA or shRNA comprises a portion that is complementary to a region of the target transcript. Thus, it will be understood that RNAi can be effected using both siRNA and shRNA in particular.

The RNAi inducing agent of the invention interferes or interrupts the translation of mRNA. Such RNAi inducing agents can be single or double stranded. Preferably, one strand of a double-stranded RNAi-inducing agent comprises at least a partial sequence complementary to a target mRNA. The nucleotides of the inhibitory nucleic acid can be chemically modified, natural or artificial. The sequence homology between the RNAi inducing agent and the targeted tight junction target mRNA may be 100% or less, but is ideally greater than about 50% and typically 90% or greater and even more preferably at least 98% and 99%. It will be understood that the percentage of sequence homology between RNAi inducing agent and the target mRNA should be sufficient to result in sequence specific association between the RNAi inducing agent, e.g. siRNA, and the target mRNA, preferably under cytoplasmic conditions.

Such siRNAs comprise two RNA strands having a region of complementarity of approximately 20 or so nucleotides in length and optionally further comprises one or two single-stranded overhangs or loops. In mammalian cells, dsRNA longer than 30 base pairs can cause non-specific gene suppression by an interferon a response. However, cells transfected with 21 nucleotide synthetic double-stranded siRNA bearing two nucleotides protruding at both 3'-ends have been found to escape an interferon response and effectively exert sequence-specific gene silencing function. The silencing effect of the synthetic siRNA, however, is transient. The double stranded siRNA molecule down regulates expression of the tight junctions of the blood brain barrier and/or the blood retinal barrier via RNAi, wherein each strand of said siRNA molecule is independently about 18 to about 28 nucleotides in length and one strand of the siRNA molecule comprises a nucleotide sequence having sufficient complementarity to the RNA of the target tight junction protein or proteins for the siRNA molecule to direct cleavage of the target RNA via RNA interference.

In shRNA, the single RNA strand may form a hairpin structure with a stem and loop and, optionally, one or more unpaired portions at the 5' and/or 3' portion of the RNA.

Another post-transcriptional gene silencing process is mediated by micro RNA or miRNA, an ssRNA species which suppress mRNA translation. Like siRNA, miRNA are derived from RNA precursors that are processed to 21-25 nucleotide sequences by endonuclease Dicer and form a sequence specific gene silencing complex.

Thus, the invention is directed to RNAi technology and can ideally be effected by, for example, siRNA, miRNA and/or shRNA. For ease of reference, siRNA and shRNA will be referred to in the following passages. However, it will be understood that siRNA, miRNA or shRNA or any other RNAi inducing agent may be used in the following methods.

According to a first aspect of the invention, there is provided the use of RNAi targeting tight junction proteins in a method for the reversible, transient and controlled size selective opening of the paracellular pathway of the blood brain barrier by delivery, preferably systemic delivery, of the RNAi inducing agent, preferably siRNA or shRNA, targeting tight junction proteins to the subject.

Advantageously, the delivery of siRNA or shRNA targeting tight junction proteins results in the controlled, reversible and transient opening of the paracellular pathway of the blood brain barrier to allow the permeation of molecules, ideally less than 15 kDa, across the brain capillary endothelial or retinal endothelial cells. Ideally, the delivery of low molecular weight drugs, such as those below approximately 1 kDa, is facilitated.

According to a specific embodiment of this aspect of the invention, there is provided the use of siRNA in a method for the reversible, transient and controlled size selective opening of the paracellular pathway of the blood brain barrier wherein the method comprises the delivery, preferably systemic delivery, of siRNA targeting tight junction proteins and results in the reversible and transient RNAi-mediated suppression of the blood brain barrier tight junction modulating peptide transcripts in brain capillary endothelial or retinal endothelial cells to allow the permeation of molecules, less than 15 kDa, across the blood brain barrier, through brain capillary endothelial or retinal endothelial cells.

The use of RNAi inducing agents, such as siRNA or shRNA, targeting tight junction proteins is the first time that the reversible, transient and size-selective opening of the BBB has been achieved. This opening of the BBB has many different applications including, but not limited to the following:

Use as an experimental model to study the paracellular system by development of a conditional TJ modulating peptide knockout mouse;

Use a conditional TJ modulating peptide knockout mouse as a general experimental platform to test efficacy of a wide range of pharmaceutical products;

Use to increase the permeability of the BBB to active agents which previously would not have permeated the BBB;

Targeting many different TJ proteins to provide for flexibility of molecule size that can cross the BBB; and Use in the treatment of many diseases or disorders which involve the paracellular pathway and blood brain barrier or blood retinal barrier.

The following passages relate to RNAi technology using siRNA, however, as stated above these passages are equally applicable to RNAi technology using miRNA, shRNA or other RNAi inducing agents.

We have found that the opening of the paracellular pathway of the BBB occurs approximately 24 to 48 hours after siRNA delivery. Levels of expression of the tight junction proteins return to normal at approximately 72 hours post siRNA delivery and hence the BBB no longer remains open after this time period. Thus, the opening of the BBB using RNAi is transient and reversible. This is a major advantage of the present invention, ensuring that the BBB integrity is restored fully post-siRNA delivery. It is this feature of temporarily compromising the integrity of the BBB to allow for the passage of small molecules into the brain which provides one of the major advantages of the invention over known techniques which opening the BBB in a potentially deleterious non-controlled and permanent manner In addition, the opening of the BBB is size-selective and controlled allowing the permeation of molecules, ideally less than 15 kDa, across the BBB. Ideally, molecules less that 1 kDa, preferably less than 800 Da, are allowed to permeate across the BBB, through the brain capillary endothelial or retinal endothelial cells. It will be understood that the size-selective opening of the BBB may be different for the different TJ proteins targeted. For example, Occludin allows the permeation of molecules of up to approximately 60 KDa to 80 KDa whereas Claudin 1, 5 and 12 allow the permeation of molecules of approximately 2 KDa or lower.

Ideally, for RNAi to be effective, a large volume of siRNA is administered to the subject to ablate/suppress the blood brain barrier/blood retinal barrier tight junction protein transcripts in brain capillary endothelial or retinal cells. Preferably, the amount of siRNA delivered is approximately 1 ug siRNA per 1 µg body weight of the subject. However, it will be understood that other volumes of siRNA may be contemplated. For example, for small mammals such as rodents including mice, this amount may be as low as from approximately 5 µg to 50 µg. Ideally, an amount of approximately 20 µg is used. For large mammals, such as humans, of typically approximately 70 kg weight, an appropriate amount of siRNA to be injected would be in the region of 0.07-0.15 grams. Again, other amounts of siRNA may be contemplated.

Preferably, delivery is by systemic administration including intra-venous delivery and intra-arterial delivery, such as intra-carotid delivery. Administration may be direct administration or via a catheter. Ideally, the siRNA is administered to the subject by systemic hydrodynamic delivery.

Hydrodynamic delivery is an efficient and inexpensive procedure which can be used to deliver a wide range of nucleic acids to tissues and other organs in-vivo. The successful application of hydrodynamic delivery is dependent on the rapid injection of a large aqueous volume containing the oligonucleotides into the vasculature of the subject.

Essentially, systemic hydrodynamic delivery according to the present invention involves the intravascular administration of siRNA. In rodents such as mice, tail-vein delivery may be contemplated. In humans or other mammals, intra-carotid administration directly to the carotid artery or heart via the jugular vein may be contemplated. Hydrodynamic delivery in humans could also be contemplated by administration via the hepatic portal vein following insertion of a line in the femoral vein. Specifically, delivery of siRNA to brain capillaries in humans could potentially be mediated via intra-carotid administration. Alternatively, the direct injection of high concentrations of siRNA in volumes, for example up to 300-400 ml, to the heart of humans may allow for enhanced delivery to the brain capillaries. Administration could take place by inserting a very narrow catheter into the femoral artery of the subject and advancing it into one of the neck arteries at the base of the brain. The siRNA may then be administered through the catheter.

The efficiency of oligonucleotide (i.e. siRNA) delivery by systemic hydrodynamic delivery is enhanced by increasing the volume and pressure, and hence permeability, of the tissue's blood vessel. Permeability can be increased by the following increasing the intravascular hydrostatic (physical) or osmotic pressure;

delivering the injection fluid rapidly (injecting the injection fluid rapidly);

using a large injection volume; and/or increasing permeability of the tight junction following suppression of TJ protein transcripts.

Advantageously, we have found that hydrodynamic delivery may be used for the delivery of siRNA targeting tight junction proteins to result in the reversible and transient RNAi-mediated suppression of blood brain barrier tight junction protein transcripts in brain capillary endothelial or retinal cells. As explained above, this opens the BBB and allows the permeation of molecules less than 15 kDa to the brain capillary endothelial or retinal cells. Delivery to the BBB has not been achieved before.

Ideally, for systemic hydrodynamic administration, the siRNA is delivered in solution, preferably phosphate buffered saline solution or water.

Ideally, the solution has a volume of between 8-10% of the body weight of the subject. We have found that this high volume delivery of siRNA directed against selected tight junction proteins increases the permeability of the brain microvasculature when compared to non-targeting siRNA.

Ideally, where the subject is a large mammal, the total volume could be in the region of several liters, depending on the body weight of the subject. Such a high volume may be desirable in situations like the treatment of traumatic brain injury or catastrophic stroke where there is no other treatment available and the subject would die without further intervention. Where the subject is a small mammal such as a mouse, the total volume is ideally from 1 to 3 ml. The exact volume to be delivered will depend on the body weight of the subject.

Conveniently, a specific volume is delivered within a specific time period, for example a rate less than 0.05 ml per gram of mammal weight per second. The introduction of a defined volume in a short time period aids this administration route.

According to one embodiment of this aspect of the invention, systemic hydrodynamic delivery to mice involves the injection of siRNA in approximately 1 to 3 ml of liquid into the tail vein of the mouse at a rate of approximately 1 ml/second.

Alternatively, the siRNA may be administered using a non-hydrodynamic approach involving the use of a high concentration of siRNA in a low volume solution. Similar concentrations of siRNA to the systemic hydrodynamic approach are used. Typically, a total volume of 70 to 200 ml for large mammals, such as humans, may be contemplated. Thus, the percentage volume based on body weight used for non-hydrodynamic delivery is much lower than hydrodynamic volumes.

An alternative route involves plasmid DNA expressing siRNA which has been developed utilizing transcription systems including T7 polymerase, and mammalian pol II or pol III promoters. The effectiveness of gene silencing by siRNA-encoding plasmids depends on DNA transfection efficiency and also results in transient siRNA expression. Such alternative routes are expanded on later in the description.

The delivery of siRNA according to the invention results in the transient, reversible and size-selective opening of the BBB. This opening may be controlled by the specific siRNA chosen and the delivery conditions. For example, the choice of the specific TJ protein siRNA may allow the permeation of molecules of different sizes to the brain endothelial or retinal endothelial cells of the BBB.

Furthermore, this invention represents a non-invasive technique for the delivery of small molecules to all areas of the brain or retina where they would otherwise be excluded. Previously, this has not been possible, and known methods for the delivery of agents to the BBB are invasive and carry many risks. For example, temporarily shrinking the BBB cells with a concentrated sugar solution has been used to disrupt the BBB in the treatment of brain tumours. This temporarily allows chemotherapy drugs to pass into the brain and reach the tumour. However, such a treatment carries significant risks and can only be used in certain circumstances. Furthermore, the BBB is disrupted in a non-size selective manner and this method only allows for a small time frame within which to deliver a drug of interest (www.ohsu.edu/bbb/bbbdtherapy.html). Thus, the provision of alternative therapies to open the BBB which can be controlled and do not have such severe side-effect for opening the blood brain barrier is highly desirable.

In addition, known TJ-associated protein knockout mice have major disadvantages in terms of compromised and deleterious BBB functionality and mortality associated with these knockout mice is high. The present invention overcomes these problems by providing for a transient knockout thereby overcoming the mortality associated with known TJ protein knockout mice.

The RNAi technique of the invention, whether siRNA, miRNA or shRNA or other RNAi inducing agent, targets TJ associated proteins from the blood brain barrier and/or blood retinal barrier. For example, the siRNA used to open the BBB is targeted to a TJ protein. Ideally, the tight junction proteins are selected from transmembrane proteins associated with the tight junction of the brain microvasculature. Typically the region of the siRNA sequence with sequence identity to the target mRNA, the tight junction protein transcripts, is from 14 to 30 nucleotides in length, for example from 16 to 24 nucleotides, more preferably from 18 to 22 nucleotides, most preferably from 19 to 21 nucleotides in length. The siRNA is sufficiently complementary to the target mRNA of the tight junction protein that the siRNA agent silences production of a protein encoded by the target mRNA. The siRNA may be blunt ended or may have overhangs at its 3' or 5' termini, preferably at both of its termini. The overhangs are preferably short in length, for example less than 30 nucleotides, preferably less than 20 nucleotides more preferably less than 10 nucleotides, even more preferably less than 5 nucleotides, most preferably less than 3 nucleotides in length. Typically, the overhangs are two nucleotides in length.

Thus, the siRNAs of the invention are typically less than 30 nucleotides in length and can be single or double stranded. Longer siRNAs can comprise cleavage sites that can be enzymatically or chemically cleaved to produce siRNAs having lengths less than 30 nucleotides, typically 21 to 23 nucleotides as above. It will be understood that siRNAs share sequence homology with corresponding target mRNAs. The sequence homology can be 100% or less and should be sufficient to result is sequence specific association between the siRNA and the targeted mRNA. Exemplary siRNAs do not activate the interferon signal transduction pathway. The most preferred embodiment of the invention comprises a siRNA having 100% sequence identity with the target mRNA, the tight junction protein. However, other sequences with less than 100% homology (as described in relation to RNAi inducing agents in general) may be used wherein the siRNA is of sufficient homology to guide the RNA-induced silencing complex (RISC) to the target mRNA for degradation.

Limited mutations in siRNA relative to the target mRNA may also be contemplated. It will be understood that the siRNA of the present invention ideally has nucleotide overhangs. For example, the siRNA may have two nucleotide overhangs (e.g. UU), thus, the siRNA will comprise a 21 nucleotide sense strand and a 21 nucleotide antisense strand paired so as to have a 19 nucleotide duplex region. The number of nucleotides in the overhang can be in the range of about 1 to about 6 homologous nucleotide overhangs at each of the 5' and 3' ends, preferably, about 2 to 4, more preferably, about 3 homologous nucleotide overhangs at each of the 5' and 3' ends.

In addition, the siRNA may be chemically modified, for example, to be more stable upon administration The nucleotides overhang can be modified, for example to increase nuclease resistance. For example, the 3' overhang can comprise 2' deoxynucleotides, e.g., TT, for improved nuclease resistance.

One of these transmembrane proteins includes junctional adhesion molecule (JAM). Alternatively, the tight junction-associated molecules are selected from one or more of the following occludins, claudins and/or zonula-occludens (ZO-1, ZO-2, ZO-3).

Sequences of exemplary siRNAs and the associated target sequence are provided below.

According to one specific embodiment of this invention, the tight junction associated molecule is chosen from one or more of claudin 1 to 19 and/or 21. Preferably, the tight junction associated molecule is claudin 1, 5 and/or 12.

According to a preferred embodiment of the invention the tight junction associated molecule is claudin-5. Ideally, the siRNA is selected from conserved regions of the Claudin-5 gene. Specifically, the claudin-5 siRNAs may have the following sequence (5' to 3'):

| | |
|---|---|
| Sense sequence: | (SEQ ID No. 1)<br>CGUUGGAAAUUCUGGGUCUUU |
| Antisense sequence: | (SEQ ID No. 2)<br>AGACCCAGAAUUUCCAACGUU |
| Sense sequence: | (SEQ ID No. 3)<br>CAAUGGCGAUUACGACAAGUU |
| Antisense sequence: | (SEQ ID No. 4)<br>CUUGUCGUAAUCGCCAUUGUU |
| Sense sequence: | (SEQ ID No. 5)<br>UCACGGGAGGAGCGCUUUAUU |
| Antisense sequence: | (SEQ ID No. 6)<br>UAAAGCGCUCCUCCCGUGAUU |
| Sense sequence: | (SEQ ID No. 7)<br>GCGCAGACGACUUGGAAGGUU |
| Antisense sequence: | (SEQ ID No. 8)<br>CCUUCCAAGUCGUCUGCGCUU |

According to a still preferred embodiment of the invention the tight junction associated molecule is claudin-1. Ideally, the siRNA is selected from conserved regions of the Claudin-1 gene. Specifically, the claudin-1 siRNA has the following sequence (5' to 3'):

| | |
|---|---|
| CLDN1 (1) target sequence: | (SEQ ID NO. 32)<br>GCAAAGCACCGGGCAGAUA: |
| Sense sequence: | (SEQ ID No. 9)<br>AUAGACGGGCCACGAAACGUU |
| Anti-sense strand: | (SEQ ID No. 10)<br>CGUUUCGUGGCCCGUCUAUUU |
| CLDN1 (2) target sequence: | (SEQ ID NO. 33)<br>GAACAGUACUUUGCAGGCA: |
| Sense strand: | (SEQ ID No. 11)<br>ACGGACGUUUCAUGACAAGUU |
| Anti-sense strand: | (SEQ ID No. 12)<br>CUUGUCAUGAAACGUCCGUUU |
| CLDN1 (4) target sequence: | (SEQ ID NO. 34)<br>UUUCAGGUCUGGCGACAUU: |
| Sense sequence: | (SEQ ID No. 13)<br>UUACAGCGGUCUGGACUUUUU |
| Anti-sense strand: | (SEQ ID No. 14)<br>AAAGUCCAGACCGCUGUAAUU |

According to a still preferred embodiment of the invention the tight junction associated molecule is Occludin. Ideally, the siRNA is selected from conserved regions of the Occludin gene. Specifically, the Occludin siRNA has the following sequence (5' to 3'):

| | |
|---|---|
| Occl (1) target sequence: | (SEQ ID NO. 35)<br>GUUAUAAGAUCUGGAAUGU: |
| Sense sequence: | (SEQ ID No. 15)<br>UGUAAGGUCUAGAAUAUUGUU |
| Anti-sense sequence: | (SEQ ID No. 16)<br>CAAUAUUCUAGACCUUACAUU |
| Occl (2) target sequence: | (SEQ ID NO. 36)<br>GAUAUUACUUGAUCGUGAU: |
| Sense sequence: | (SEQ ID No. 17)<br>UAGUGCUAGUUCAUUAUAGUU |
| Anti-sense sequence: | (SEQ ID No. 18)<br>CUAUAAUGAACUAGCACUAUU |
| Occl (3) target sequence: | (SEQ ID NO. 37)<br>CAAAUUAUCGCACAUCAAG: |
| Sense sequence: | (SEQ ID No. 19)<br>GAACUACACGCUAUUAAACUU |
| Anti-sense sequence: | (SEQ ID No. 20)<br>GUUUAAUAGCGUGUAGUUCUU |
| Occl (4) target sequence: | (SEQ ID NO. 38)<br>AGAUGGAUCGGUAUGAUAA: |
| Sense sequence: | (SEQ ID No. 21)<br>AAUAGUAUGGCUAGGUAGAUU |
| Anti-sense sequence: | (SEQ ID No. 22)<br>UCUACCUAGCCAUACUAUUUU |

According to a preferred embodiment of the invention the tight junction associated molecule is claudin-12. Ideally, the siRNA is selected from conserved regions of the Claudin-12 gene. Specifically, the claudin-5 siRNAs may have the following sequence (5' to 3'):

| | |
|---|---|
| CLDN12 SIRNA (1) Target sequence:<br>GAAAUCGACAUUCCAGUAG | (SEQ ID NO. 39) |
| 5'-GAAAUCGACAUUCCAGUAGUU-3' | (SEQ ID No. 24) |
| 5'-CUACUGGAAUGUCGAUUUCUU-3' | (SEQ ID No. 25) |
| CLDN12 SIRNA (2) Target sequence:<br>CGUGGUACCUGUCGGUUGA | (SEQ ID NO. 40) |
| 5'-CGUGGUACCUGUCGGUUGAUU-3' | (SEQ ID No. 26) |
| 5'-UCAACCGACAGGUACCACGUU-3' | (SEQ ID No. 27) |
| CLDN12 SIRNA (3) Target sequence:<br>GUAACACGGCCUUCAAUUC | (SEQ ID NO. 41) |
| 5'-GUAACACGGCCUUCAAUUCUU-3' | (SEQ ID No. 28) |
| 5'-GAAUUGAAGGCCGUGUUACUU-3' | (SEQ ID No. 29) |
| CLDN12 SIRNA (4) Target sequence:<br>GGUCUUUACCUUUGACUAU | (SEQ ID No. 42) |
| 5'-AAUCUUUACCUUUGACUAUUU-3' | (SEQ ID No. 30) |
| 5'-AUAGUCAAAGGUAAAGAUUUU-3' | (SEQ ID No. 31) |

The techniques of designing siRNA are well known to those skilled in the art and will not be expanded on in detail here.

It will be understood that the siRNA used in the present invention may target a single TJ modulating peptide. Alternatively, one or more siRNAs targeting different TJ proteins may be used concurrently. For example, siRNA targeting several different types of Claudin proteins may be contemplated. When using combinations siRNA targeting different TJ proteins, the crucial aspect is that the integrity of the overall tight junction should be preserved.

According to one embodiment of this aspect of the invention, combinations of siRNA could include claudin-1 with claudin-5, claudin-12 with claudin-5, claudin-12 with claudin-1. Alternatively, claudin-1, claudin-5 and claudin-12 may be used together. Occludin may also be combined with one or more Claudin types. It is envisaged that these combinations further increase permeability at the BBB in a controlled and size-selective nature.

shRNA may also be chosen to target these TJ proteins. shRNA targeting TJ proteins will ultimately have the same sense and anti-sense sequence as the siRNA. The only difference is that they contain short hairpins composed of the following nucleotides UAUCAAGAG which form a hairpin structure and allow for them to be cloned into delivery vectors.

Ideally, an inducible vector is used for shRNA delivery to prevent the otherwise continuous expression of the shRNA targeting a TJ protein of interest and resultant continuous suppression of these TJ targeting proteins. For example, AAV-mediated delivery which will be highly localised to specific regions of the brain or retina may be used to deliver shRNA. Preferably, inducible AAV vectors which allow for the induced expression of shRNA targeting TJ proteins when specific drugs are administered are used. Such inducible AAV vectors enable the transient suppression of the tight junction targeting proteins, such as claudin-5.

According to a second aspect of the present invention, the delivery of the RNA inducing agent, such as siRNA, miRNA or shRNA etc, according to the invention may be used in the generation of an experimental animal model used for studying the action of the paracellular pathway and the physiology of the BBB. This type of animal model overcomes high mortality rates associated with the known BBB knockout mouse as it reversibly, transiently and in a controlled size selective manner opens the paracellular pathway of the BBB. Such a conditional tight junction protein knockout mouse which transiently suppresses the BBB tight junction proteins to open the BBB can be used to test the efficacy of a wide range of pharmaceutical products (including such products which previously could not permeate the BBB) and/or study the paracellular system.

As such, this method can be used in an animal model for the testing of various active agents which have previously not been able to penetrate the BBB and the generation of new treatments of diseases and disorders which affect brain and retinal function. Advantageously, this method enables the generation of an ideal experimental platform for the assessment of a wide range of pharmacological agents which would otherwise not traverse the blood-brain barrier. Thus, this method could allow for the establishment of experimental animal models, for neurodegenerative and neuropsychiatric disorders etc.

According to a third aspect of this invention, there is provided the use of an RNAi inducing agent, such as siRNA, miRNA or shRNA etc, targeting tight junction proteins in the manufacture of a medicament for the treatment of disease or disorder of the brain or retina wherein the method comprises the reversible, transient and controlled size selective opening of the paracellular pathway of the blood brain barrier by the delivery, preferably systemic delivery, of the siRNA targeting tight junction proteins to result in the reversible and transient RNAi-mediated suppression of blood brain barrier tight junction protein transcripts in brain capillary endothelial cells and/or retinal endothelial cells and allow the permeation and delivery of an active agent, less than 15 kDa, directed to the treatment of the disease or disorder of the brain or retina.

The RNAi inducing agent, preferably siRNA (miRNA or shRNA etc), targeting the tight junction proteins transiently opens the blood brain barrier to allow delivery of the active agent across the blood brain barrier. Ideally, the method comprises the sequential administration of the active agent after administration of the siRNA or shRNA. This ensures that paracellular pathway is open when the active agent is administered and the active agent can permeate through the brain capillary endothelial cells and/or retinal endothelial cells to reach the brain and/or retina. However, it may also be contemplated that the delivery of the active agent takes place before or concurrently/simultaneously with the RNAi inducing agent.

This aspect of the present invention is applicable for the treatment of many diseases or disorders where the BBB or BRB is implicated. These include but are not limited to neurodegenerative disorders (such as Alzheimer's disease, multiple sclerosis etc), stroke and traumatic brain injury (TBI), and infectious processes and inflammatory pain, retinal disorders including age-related macular degeneration (AMD), glaucoma and diabetic retinopathy. For example, the present invention may be used for the controlled delivery of therapeutic agents to the central nervous system (CNS) in a range of neurodegenerative or other conditions that currently offer little or no prospect of effective treatment.

According to this aspect of the present invention, the treatment of the particular disease generally involves the opening of the BBB with or followed by delivery of an active agent across the BBB. The active agent is ideally delivered after the opening of the BBB, i.e. after 24 or 48 hours post-siRNA delivery. Alternatively, as mentioned before the active agent many be co-administered with or prior to the RNAi inducing agent.

The active agent may be chosen from conventional pharmaceuticals, such as agents that modulate neuronal function, chemotherapeutic agents, anti-tumour agents, agents that modulate retinal function and non-steroidal anti-inflammatories (NSAIDs). As such, the active agent may be any conventional biologically active therapeutic agent.

Alternatively, the active agent may be a hypertonic solution, preferably a hypertonic saline or sugar solution. Such hypertonic solutions may be used in the treatment of traumatic brain injury to allow for water to be driven out of the brain following injury, and may significantly prevent the occurrence of cerebral oedema. Mannitol, a sugar solution, may also be used in the present invention. Mannitol is used in conventional "mannitol osmotherapy" however, mannitol when used conventionally does not cross the BBB. Mannitol acts as an osmotic diuretic agent and a weak renal vasodilator.

It will be understood that the active agent may also be a small molecule, antisense oligonucleotide, ribozyme or protein, polypeptide or peptide.

According to a preferred embodiment, the active agent is a further RNAi inducing agent, including siRNA, miRNA or shRNA etc, which targets the disease or disorder being treated, such that after opening of the BBB, further RNAi inducing agents could be delivered into the brain to treat the particular disease or disorder.

This aspect of the present invention will now be discussed in relation to several specific diseases or conditions and one RNAi inducing agent siRNA, although other RNAi inducing agents such as shRNA or miRNA could also be used.

The stress response in traumatic brain injury (TBI) is manifested by the cessation of water diffusion across the BBB, leading to acute increases in intracranial pressure and cerebral oedema. Conventional therapies for the management of cerebral oedema and raised intracranial pressure following TBI involve hyperosmolar and hypertonic therapy, including saline or sugar therapy. For example, the osmotic diuretic mannitol is commonly used to treat TBI as it establishes an osmotic gradient between plasma and brain cells and draws water across the BBB into the vascular compartment. Alternatively, hypertonic saline produces a reduction in cerebral oedema by moving water out of cells, reducing tissue pressure and cell size. For the acute treatment of TBI, patients are given mannitol and hypertonic saline to try and resolve the osmotic shift in water diffusion in the brain. However, mannitol and hypertonic saline will only be effective for up to 24 hours and if swelling occurs for longer than this period, patients will either die or be left with permanent brain damage. Thus, both mannitol and hypertonic saline have significant disadvantages in terms of side-effects, such as severe intravascular volume depletion, hypotension and hyperkalemia, and there is difficulty in ascertaining the correct dosage needed. Furthermore, temporarily shrinking the BBB cells with a concentrated sugar solution has been used to disrupt the BBB in the treatment of brain tumours as expanded on before can have significant deleterious side effects, is only used as a last resort and is not suitable for all patients. Indeed the use of mannitol to open the BBB does not result in selective controlled opening of the BBB and can result in further damage to the brain. Thus, there is a need to provide an alternative therapy for dealing with TBI or stroke.

According to this aspect of the present invention, there is provided the use of siRNA in the manufacture of a medicament for the treatment of a traumatic brain injury or stroke wherein the method comprises the reversible, transient and controlled size selective opening of the paracellular pathway of the blood brain barrier by the delivery, preferably systemic delivery, of the siRNA targeting tight junction proteins to result in the reversible and transient RNAi-mediated suppression of blood brain barrier tight junction protein transcripts in brain capillary endothelial cells and optionally following the administration of an active agent, such as a hypertonic sugar or saline solution, to allow the permeation and free diffusion of water across the blood brain barrier, reduction of intracranial pressure and/or reduction of cerebral oedema.

This ability to allow the transient, controlled and reversible free permeation and free diffusion of water across the blood brain barrier is very important in conditions such as traumatic brain injury (TBI) or catastrophic stroke. In these conditions, the cessation of water diffusion from the brain to the blood can cause increase intracranial pressure, leading to cerebral oedema and possibly death or severe disability. The present invention provides a new treatment to allow brain-to-blood diffusion of water and reduce the effects of intracranial pressure and/or cerebral oedema. Thus, advantageously and unexpectedly, the use of siRNA targeting tight junction proteins enhances water diffusion across the BBB. This provides an alternative means for intervention in cerebral oedema associated with TBI, acute TBI in particular. The use of an RNAi inducing agent targeting tight junction proteins allows the free diffusion of water from the brain of subjects with TBI in a controlled and reversible manner for a period of up to 72 hours when the BBB is open. An active agent, such as a hypertonic solution (e.g. mannitol or hypertonic saline) may optionally be used together with the siRNA to provide an osmotic gradient to facilitate water diffusion initially until the BBB opens after 24/48 hours.

Thus, it will be understood that the siRNA targeting the tight junction proteins may be used on its own or in combination (either sequentially or simultaneously) with conventional TBI or stroke therapies, such as hyperosmolar and hypertonic saline/sugar therapy or mannitol osmotherapy.

According to a specific embodiment, the method of the invention allows for water flux from the brain to the blood in a highly controlled manner and may be used in combination with mannitol/hypertonic sugar or saline therapy. Advantageously, the siRNA and mannitol/hypertonic saline therapy may be infused at the same time, and as the mannitol/hypertonic saline stops working after approximately 24 hours, the controlled opening of the BBB commences to further allow water flux from the brain through the BBB.

According to another aspect of the present invention, there is provided the use of siRNA in the manufacture of a medicament for the treatment of a neurodegenerative or neuropsychiatric disorder wherein the method comprises the reversible, transient and controlled size selective opening of the paracellular pathway of the blood brain barrier by the delivery, preferably systemic delivery, of siRNA targeting tight junction proteins to result in the reversible and transient RNAi mediated suppression of the blood brain barrier tight junction protein transcripts in brain capillary endothelial cells and allows the permeation and delivery of an active agent less than 15 kDa which modulates neuronal function to the brain capillary endothelial cells.

The agent which modulates neuronal function may be any conventional treatment for conventional neurodegenerative or neuropsychiatric disorders.

Age-related macular degeneration (AMD) affects more than 1.75 million individuals in the United States and is the leading cause of vision impairment and blindness in persons 60 years or older. The greatest known risk factor for developing AMD is advanced age, however, ocular risk factors for exudative AMD include the presence of soft drusen, macular pigment changes, and choroidal neovascularization. Additional risk factors associated with AMD include smoking, obesity, hypertension and positive family history. AMD presents in two basic forms: dry or wet AMD, the latter being associated with vascular permeability and hemorrhages. In the more severe, exudative form, new vessels originating from the choriocapillaris bed develop under the macula of the retina, growing into the sub-retinal space between the retina and the retinal pigmented epithelium (RPE). These newly sprouted vessels leak serous fluid and blood under the neurosensory retina and lead to macular edema and retinal detachment causing symptoms of visual distortion (metamorphosia) and blurring of vision.

Glaucoma is a complex disease, which may involve degeneration of the trabecular meshwork and/or lamina cribrosa of the eye, resulting in aberrant function of drainage channels and/or degeneration of the optic nerve head. As a result, ganglion cells (the output neurons of the retina) die, resulting in narrowing of and/or loss of the visual fields, leading, if untreated, to severe visual handicap in a significant proportion of cases.

The majority of cases of open-angle glaucoma involve increased intraocular pressure although a growing number of so-called normal pressure glaucomas are now being identified. In those cases where a pressure build up is registered, pressure-reducing eye drops are often of substantial value in slowing down the progression of the disease. However, surgical intervention is sometimes required to alleviate intraocular pressure and some forms of open angle glaucoma become refractory to treatment.

Open angle glaucoma affects up to 1 million persons within the British Isles at the present time. While most forms of the disease are multigenic or multifactorial, some forms of the diseases are inherited according to apparent mendelian ratios, i.e., they are transmitted in an autosomal dominant sense. In some such forms of disease, mutations within the so-called myocilin gene have been identified (Stone et al, Science, 275, 1997, 668-670). Moreover, in up to 4% of multifactorial forms of disease, similar mutations have been encountered. Thus, 40,000 persons, or more, within the British Isles, have a form of glaucoma caused my mutations within the myocilin gene.

Diabetic retinopathy, eye damage that frequently occurs as a result of diabetes, is related to the breakdown of the blood-retinal barrier. The barrier becomes more leaky in patients with diabetic retinopathy.

According to this aspect of the present invention, there is provided the use of RNAi in the manufacture of a medicament for the treatment of a disease of the retina wherein the method comprises the reversible, transient and controlled size selective opening of the paracellular pathway of the blood brain or blood retinal barrier wherein the method comprises the delivery, preferably systemic delivery, of siRNA targeting tight junction proteins which results in the reversible and transient RNAi mediated suppression of the blood brain or blood retinal barrier tight junction protein transcripts in brain capillary endothelial cells and/or retinal endothelial cells and allow the permeation and delivery of active agent which modulates retinal function, less than 15 kDa, across the brain capillary endothelial cells and/or retinal capillary endothelial cells.

This aspect of the invention, involves the treatment of a disease of the retina by opening the BBB or BRB to allow the permeation and delivery of active agent which modulates retinal function across the retinal capillary endothelial cells.

The agent which modulates retinal function may be any conventional treatment for the above conditions. Additionally, for example, vascular endothelial growth factor receptor (VEGF) dysregulation is a key mediator of age-related macular degeneration (AMD), thus, increased delivery of these inhibitors to the retina may significantly retard the progression of AMD. Until now, these small molecule inhibitors of the VEGF receptor were not able to cross the blood retinal barrier. This is a major advantage of the present invention.

According to yet another embodiment of the present invention, there is provided the use of siRNA in the manufacture of a medicament for the treatment of a brain tumor wherein the method comprises the reversible, transient and controlled size selective opening of the paracellular pathway of the blood brain barrier by the delivery, preferably systemic delivery, of siRNA targeting tight junction proteins which results in the reversible and transient RNAi-mediated suppression of the blood brain barrier tight junction protein transcripts in brain capillary endothelial cells and allows the permeation and delivery of an anti-tumor or chemotherapeutic agent less than 15 kDa to the brain capillary endothelial cells.

Thus, this aspect of the present invention provides for the transient opening of the BBB/BRB which can be used for the enhanced delivery of conventional chemotherapeutic or anti-tumour drugs which would normally be redundant for the treatment of conditions such as brain tumours as until now they have been unable to cross the BBB.

In a typical embodiment of all aspects of the invention, the subject is a mammal such as a cow, horse, mouse, rat, dog, pig, goat, or a primate (Macaque). In a much preferred embodiment, the subject is a human, e.g. a normal human or human diagnosed with or predicted to have a disease or disorder that is currently un-treatable due to the non-availability of drugs that cross the BBB.

According to a fourth aspect of the invention, there is provided a pharmaceutical composition comprising a pharmaceutically acceptable solution of siRNA targeting tight junction proteins to result in the reversible, transient and controlled size selective opening of the paracellular pathway of the blood brain barrier suitable for delivery and an active agent for the treatment of a defined disease or disorder.

The active agent may be chosen from conventional pharmaceuticals, such as active agents that modulate neuronal function, chemotherapeutic agents, anti-tumour agents, agents that modulate retinal function and non-steroidal anti-inflammatories (NSAIDs) or hypertonic solution as defined previously. Specific examples are given in the above passages.

Alternatively or additionally, the active agent may also be a small molecule, antisense oligonucleotide, ribozyme or protein, polypeptide or peptide. Ideally, the active agent is a further siRNA which targets the disease or disorder being treated, such that after opening of the BBB, further siRNA molecules could be delivered into the brain to treat the particular disease or disorder.

Ideally, the pharmaceutical composition is adapted for systemic hydrodynamic delivery and is present in a pharmaceutically acceptable carrier.

It will be understood that the siRNA and active agent may be suitable for simultaneous or sequential administration. Thus, the siRNA may be administered alone or in combination with an active agent. Although, the sequential administration after the BBB has opened is the preferred delivery method for some active agents.

According to yet another aspect of the present invention, there is provided a method for the reversible, transient and controlled RNAi mediated size selective opening of the paracellular pathway of the blood brain barrier comprising the steps of the delivery, preferably systemic delivery, of an effective amount of siRNA targeting tight junction proteins to result in the transient and reversible RNAi mediated suppression of blood brain barrier tight junction protein transcripts in brain capillary endothelial or retinal cells and to allow the permeation of molecules less than 15 kDa to brain capillary endothelial or retinal cells.

According to a further aspect of the present invention, there is provided a method for the treatment of a disease or disorder comprising the reversible, transient and controlled RNAi-mediated size selective opening of the paracellular pathway of the blood brain barrier wherein the method comprises identifying a subject at risk for developing the disease or disorder;

administering an effective amount of an RNAi inducing agent, preferably siRNA, miRNA or shRNA etc, targeting tight junction proteins by delivery, preferably systemic delivery, of the RNAi inducing agent to result in the transient and reversible RNAi-mediated suppression of blood brain barrier tight junction protein transcripts in brain capillary endothelial or retinal endothelial cells and allow the permeation of active agents used in the treatment of the disease or disorder less than 15 kDa to the brain capillary endothelial and/or retinal cells; and administering an active agent suitable for the treatment of the disease or disorder.

Advantageously, this method increases the permeability of the BBB to drugs or other active agents.

We have previously covered both hydrodynamic and non-hydrodynamic delivery of siRNA to the region of interest, i.e. the BBB.

Other delivery methods could be contemplated, such as transcellular, receptor-mediated, delivery of molecules across the BBB. For example, siRNA may be delivered using electroporation or lipid mediated transfection. Additional delivery methods include the use of cationic polymers, modified cationic polymers, peptide molecular transporters, lipids, liposomes, non-cationic polymers and/or viral vectors for delivery of the RNAi inducing agent.

Further delivery methods include encapsulating or conjugating the siRNA so that delivery to the BBB is affected. As previously described above, genetically engineered proteins termed "Molecular Trojan horses" could be used to affect delivery to the BBB. There are now numerous methods whereby siRNAs can be chemically modified with, for example, cholesterol moieties in order to allow for their diffusion across the plasma membrane of cells. In principle, these cholesterol conjugated siRNAs targeting claudin-5 or other tight junction proteins could be administered without the need for a hydrodynamic injection.

Other viral mediated delivery systems may be contemplated. For example, targeted delivery of proteins across the BBB could be affected by a lentivirus vector system.

Alternatively, mosaic vector particles have previously been described, and show significant promise for targeted delivery of adeno-associated virus (AAV) particles specifically to the vasculature (Stachler M D et al., 2006). Moreover, Work L M et al (2006) have shown that generating distinct capsid modifications on AAV particles will allow for targeting of viral vectors to specific viral beds including those associated with the brain. This technique is required when shRNA is used where the short hairpin is used for cloning into the delivery vectors. As discussed above such an inducible vector system provides for the controlled and transient suppression of the blood brain barrier.

Thus, according to this aspect of the invention, endothelial cell specific AAV could be generated containing antibiotic/drug-inducible shRNA (short hairpin RNA) sequences specific for the suppression of claudin-5 to provide a method for the inducible opening of the BBB or BRB following infection of brain microvascular endothelial cells with MV containing shRNA against claudin-5. Other viral vectors may also be contemplated.

Furthermore, recently Szymanski et al., (2007) reported the development of an inducible plasmid pBRES which is controlled by the FDA-approved drug mifepristone (MFP) and, in principle, is small enough to be packaged into and subsequently delivered by AAV viral particles. pBRES is modular in design, consisting of a transactivator-inducer protein, TA, driven by a promoter of choice which interacts with the drug MFP to allow expression of the transgene of interest, i.e. shRNA, (from a regulated promoter (e.g. 6×Gal4/TAT). As this minimal promoter has been designed using standard Pol II elements it is unlikely to drive conventional shRNA genes which require Pol III promoters, the shRNA sequences should be cloned with micro RNA (miRNA) backbones (shRNAmirs) into pcDNA 6.2-GW/EmGFP-miR (BLOCK-iT Pol II miRNAi Expression Vector Kit; Invitrogen cat. no. K4935-00). The resulting EmGFP-tagged shRNAmir can then be excised and inserted into pBRES after the regulated promoter. In addition, in order to add a further safeguard against inappropriate expression of shRNA, the TA protein (which in turn will lead to shRNA expression induction) is driven using the promoter for transferrin, claudin-12, Tie-2 or p-glycoprotein which drive high expression in brain endothelium when compared to other tissues. Putative promoters from these genes derived following bioinformatic analyses can then be tested for efficiency and tissue specificity at driving expression of EGFP in HUVEC (ATCC no. CRL-1730) and bend.3 (ATCC no. CRL-2299) endothelial cell lines and the most efficient promoter will be incorporated into the inducible system to drive the TA protein. Finally, the resulting MFP-inducible, endothelial-specific shRNA-expressing pBRES plasmid can be linearised and cloned into the AAV shuttle vector pAAV2 CMV and packaged into the capsid modified AAV1 for delivery to the vascular endothelium.

To date, a major limitation however in the use of AAV-1 has been the lack of an efficient small-scale purification strategy. Recently however, it has been disclosed that two AAV-1 capsid protein modifications can enhance vascular gene transfer significantly while also allowing easy purification of vector particles. Using mosaic vector particles comprised of capsid proteins containing the well-characterized RGD4C modification to target integrins present on the luminal surface of endothelial cells lining the vasculature, and capsid proteins containing a modification that allows for metabolic biotinylation and efficient purification of mosaic particles by avidin affinity chromatography, it is now possible to generate modified AAV-1 particles which will specifically transduce endothelial cells with a high efficiency (Stachler & Bartlett, 2006). Thus, the use of AAV-1 for delivery of shRNA in particular to the BBB and/or BRB is now feasible in practice.

In the specification, the terms "comprise, comprises, comprised and comprising" and any variation thereof and the terms "include, includes, included and including" and any variation thereof are considered to be totally interchangeable and they should all be afforded the widest interpretation.

The invention is not limited to the embodiments described above but may be varied within the scope of the claims.

REFERENCES

Anderson, J. M. (2001). "Molecular structure of tight junctions and their role in epithelial transport." *News Physiol Sci* 16: 126-30.

Bazzoni, G. (2006). "Endothelial tight junctions: permeable barriers of the vessel wall." *Thromb Haemost* 95 (1): 36-42.

Bickel, U., T. Yoshikawa, et al. (2001). "Delivery of peptides and proteins through the blood-brain barrier." *Adv Drug Deliv Rev* 46 (1-3): 247-79.

Edwards, R. H. (2001). "Drug delivery via the blood-brain barrier." *Nat Neurosci* 4 (3): 221-2.

Fanning, A. S. and J. M. Anderson (1998). "PDZ domains and the formation of protein networks at the plasma membrane." *Curr Top Microbiol Immunol* 228: 209-33.

Furuse, M., H. Sasaki, et al. (1998). "A single gene product, claudin-1 or -2, reconstitutes tight junction strands and recruits occludin in fibroblasts." *J Cell Biol* 143 (2): 391-401.

Herweijer, H. and J. A. Wolff (2007). "Gene therapy progress and prospects: hydrodynamic gene delivery." *Gene Ther* 14 (2): 99-107.

Hino, T., T. Yokota, et al. (2006). "In vivo delivery of small interfering RNA targeting brain capillary endothelial cells." *Biochem Biophys Res Commun* 340 (1): 263-7.

Inai, T., J. Kobayashi, et al. (1999). "Claudin-1 contributes to the epithelial barrier function in MDCK cells." *Eur J Cell Biol* 78 (12): 849-55.

Kausalya, P. J., M. Reichert, et al. (2001). "Connexin45 directly binds to ZO-1 and localizes to the tight junction region in epithelial MDCK cells." *FEBS Lett* 505 (1): 92-6.

Kiang, A. S., A. Palfi, et al. (2005). "Toward a gene therapy for dominant disease: validation of an RNA interference-based mutation-independent approach." *Mol Ther* 12 (3): 555-61.

Koto, T., K. Takubo, et al. (2007). "Hypoxia disrupts the barrier function of neural blood vessels through changes in the expression of claudin-5 in endothelial cells." *Am J Pathol* 170 (4): 1389-97.

Lewis, D. L., J. E. Hagstrom, et al. (2002). "Efficient delivery of siRNA for inhibition of gene expression in postnatal mice." *Nat Genet.* 32 (1): 107-8.

Matter, K. and M. S. Balda (2003). "Holey barrier: claudins and the regulation of brain endothelial permeability." *J Cell Biol* 161 (3): 459-60.

McCaffrey, A. P., L. Meuse, et al. (2002). "RNA interference in adult mice." *Nature* 418 (6893): 38-9.

Miller, G. (2002). "Drug targeting. Breaking down barriers." *Science* 297 (5584): 1116-8.

Nitta, T., M. Hata, et al. (2003). "Size-selective loosening of the blood-brain barrier in claudin-5-deficient mice." *J Cell Biol* 161 (3): 653-60.

Palfi, A., M. Ader, et al. (2006). "RNAi-based suppression and replacement of rds-peripherin in retinal organotypic culture." *Hum Mutat* 27 (3): 260-8.

Pardridge, W. M. (2005). "Molecular biology of the blood-brain barrier." *Mol Biotechnol* 30 (1): 57-70.

Pardridge, W. M. (2006). "Molecular Trojan horses for blood-brain barrier drug delivery." *Curr Opin Pharmacol* 6 (5): 494-500.

Reese, T. S. and M. J. Karnovsky (1967). "Fine structural localization of a blood-brain barrier to exogenous peroxidase." *J Cell Biol* 34 (1): 207-17.

Reynolds, A., D. Leake, et al. (2004). "Rational siRNA design for RNA interference." *Nat Biotechnol* 22 (3): 326-30.

Schlageter, K. E., P. Molnar, et al. (1999). "Microvessel organization and structure in experimental brain tumors: microvessel populations with distinctive structural and functional properties." *Microvasc Res* 58 (3): 312-28.

Spencer, B. J. and I. M. Verma (2007). "Targeted delivery of proteins across the blood-brain barrier." *Proc Natl Acad Sci USA* 104 (18): 7594-9.

Tsukita, S., M. Furuse, et al. (2001). "Multifunctional strands in tight junctions." *Nat Rev Mol Cell Biol* 2 (4): 285-93.

Turksen, K. and T. C. Troy (2004). "Barriers built on claudins." *J Cell Sci* 117 (Pt 12): 2435-47.

Wolburg, H. and A. Lippoldt (2002). "Tight junctions of the blood-brain barrier: development, composition and regulation." *Vascul Pharmacol* 38 (6): 323-37.

Zahraoui, A., D. Louvard, et al. (2000). "Tight junction, a platform for trafficking and signaling protein complexes." *J Cell Biol* 151 (5): F31-6.

Stachler M D, Bartlett J S. Mosaic vectors comprised of modified AAV1 capsid proteins for efficient vector purification and targeting to vascular endothelial cells. *Gene Therapy.* 2006 June; 13 (11):926-31

Work L M, Büning H, Hunt E, Nicklin S A, Denby L, Britton N, Leike K, Odenthal M, Drebber U, Hallek M, Baker A H. Vascular bed-targeted in vivo gene delivery using tropism-modified adeno-associated viruses. *Molecular Therapy.* 2006 April; 13 (4):683-93. Epub 2006 Jan. 4

The present invention will now be described with reference to the following non-limiting figures and examples.

FIG. 1 shows the results of the quantification of claudin-5 protein and mRNA levels.

FIG. 1A is a western blot analysis of claudin-5 expression 24, 48 and 72 hours post hydrodynamic tail vein delivery of siRNA. Controls used included an un-injected control, PBS injected control and non-targeting (Rhodopsin) siRNA injected control mice. Western blot analysis of claudin-5 expression 24 hours post delivery of siRNA, showed a decrease in expression when compared to un-injected, PBS injected and non-targeting siRNA injected mice. This suppression was also evident 48 post injection (CLDN5 A+B; lysates from 2 different mice). Levels of claudin-5 were similar to the control groups 72 hours and 1 week post delivery of claudin-5 siRNA when compared to the corresponding levels of β-actin in the same lane (FIG. 1A).

Figure 1B:
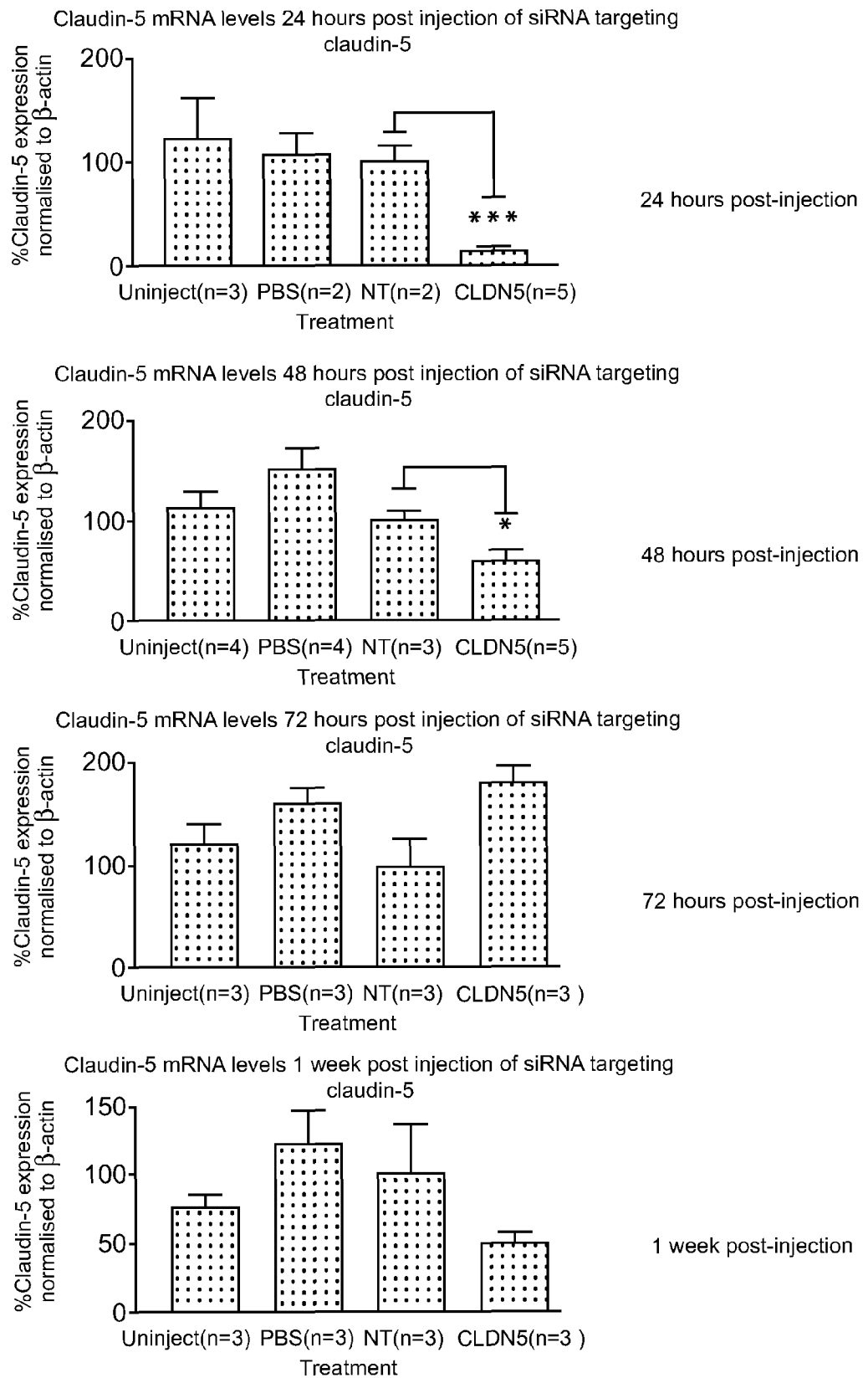

FIG. 1B shows RT-PCR analysis of claudin-5 mRNA post-injection of siRNA compared to the control groups—un-injected control, PBS injected control and non-targeting (Rhodopsin) siRNA injected control mice. RT-PCR analysis showed levels of claudin-5 mRNA to be significantly decreased 24 hours post-injection of siRNA compared to the control groups with $P=0.0427$ (*) following ANOVA with a Tukey-Kramer post-test, while also showing suppression at 48 hours post-injection of claudin-5 siRNA with $P=0.0478$ (*). Levels of claudin-5 mRNA, 72 hours ($P=0.0627$) and 1 week ($P=0.2264$) post injection were not significantly changed compared to the non-targeting control group, showing P values greater than 0.05, representing insignificance (FIG. 1B).

Figure 2:
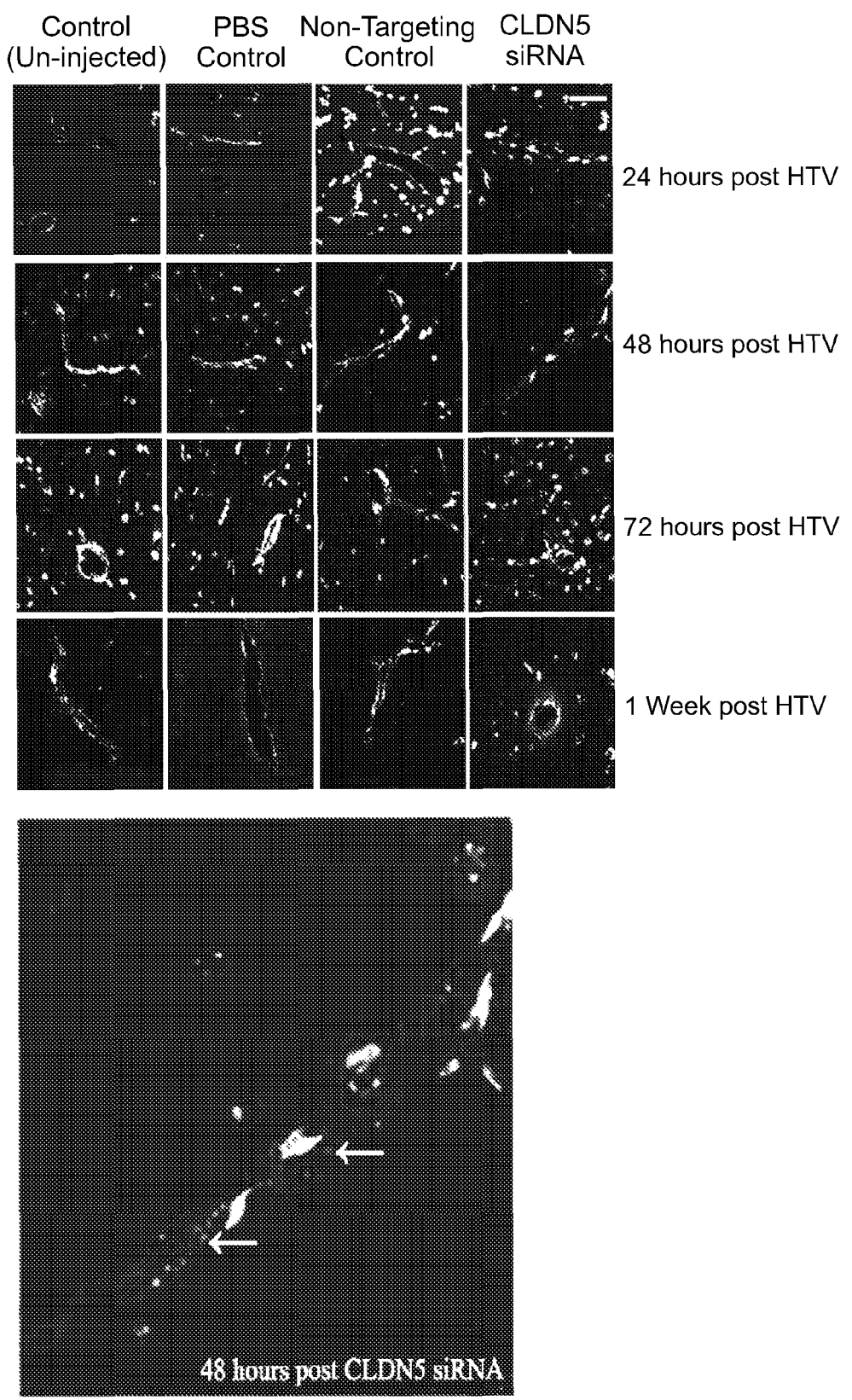

FIG. 2 shows the results of immunohistochemical analysis of claudin-5 expression and localisation in the microvessels of the brain revealed a continuous and distinct pattern of staining in the microvasculature of the brain in the un-injected, PBS injected and non-targeting control mice at all time points (Red=Claudin-5; Blue-DAPI=nuclei). This pattern of staining appeared decreased and non-continuous 24 hours post delivery of claudin-5 siRNA, with a striking decrease in expression 48 hours after injection. The appearance of claudin-5 staining 72 hours post-injection of claudin-5 siRNA was evident, yet non-continuous, however, 1 week post-injection, claudin-5 expression appeared similar to that of the control groups. Scale bar approx. 20 µm. These results are representative of at least 5 separate experiments.

Figure 3A:
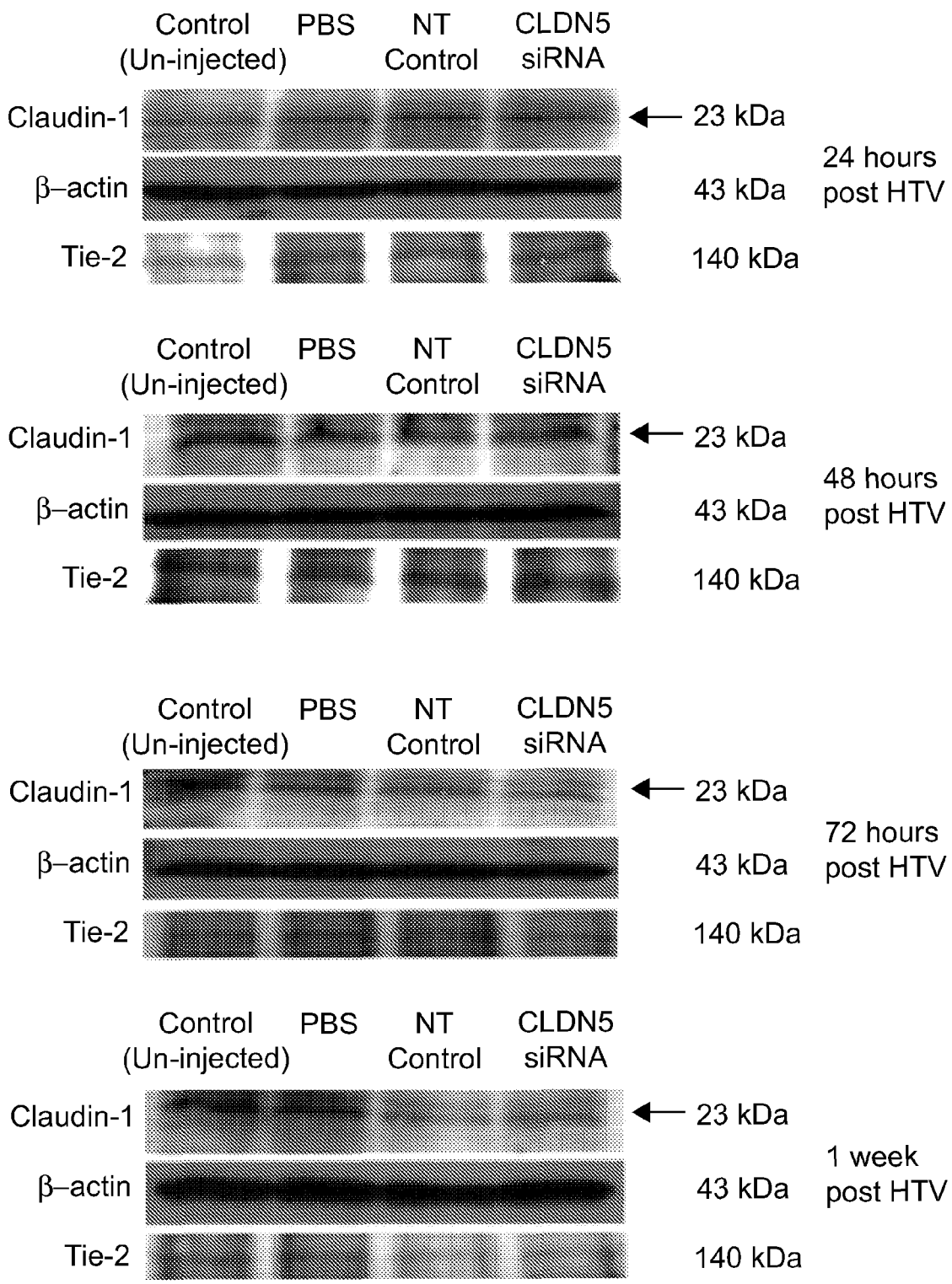
Figure 3B:
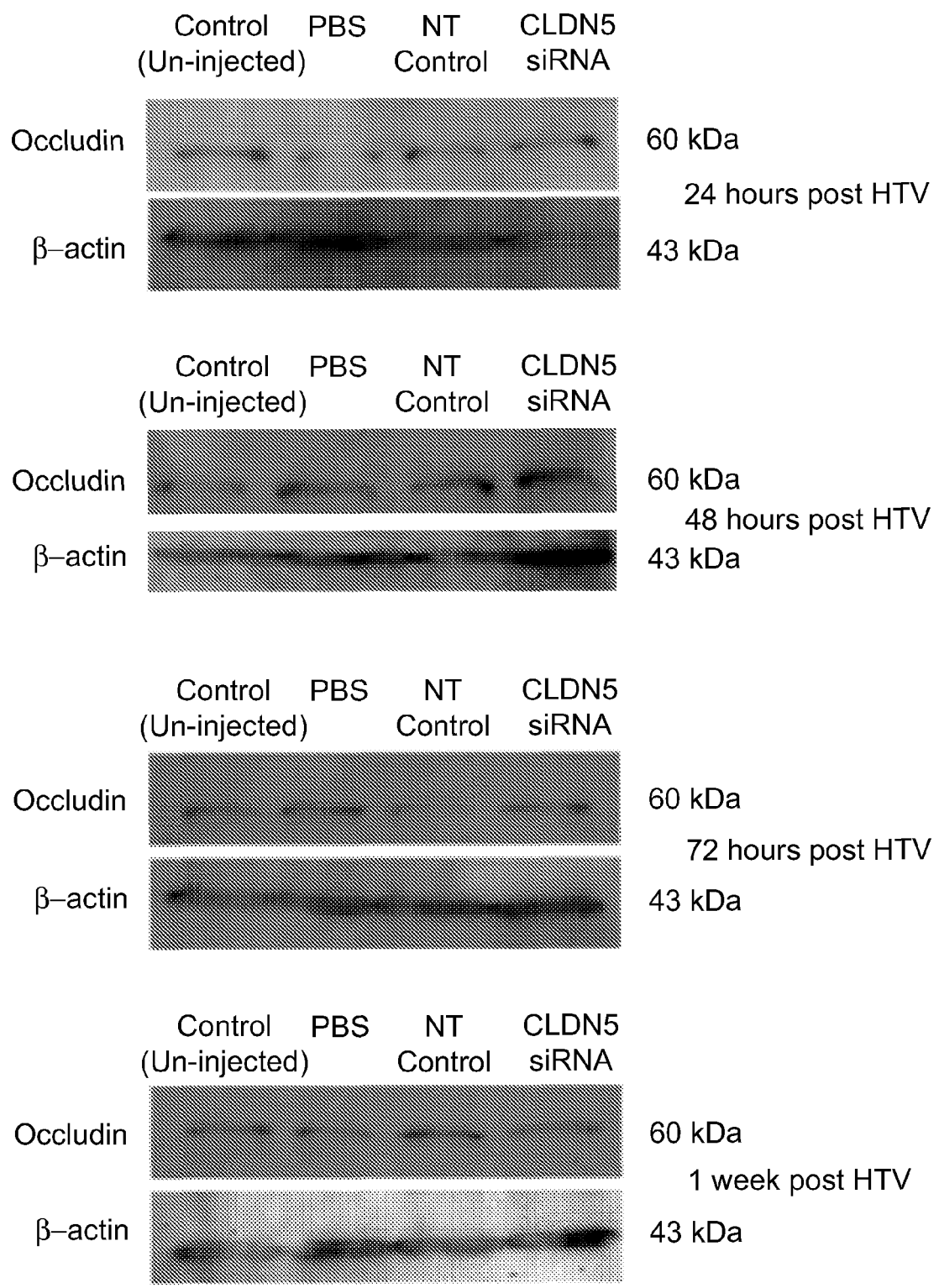
Figure 4A:
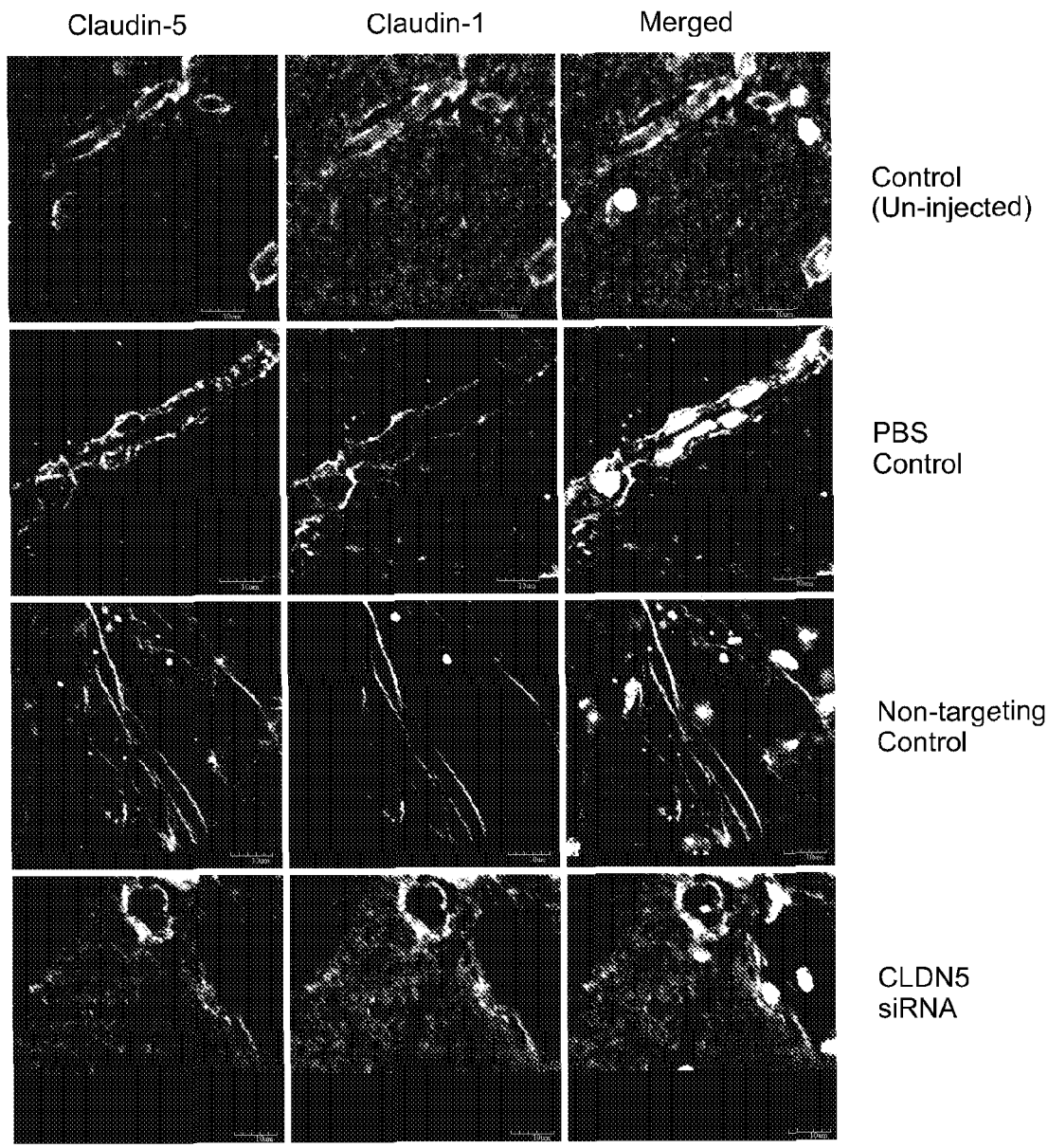
Figure 4B:
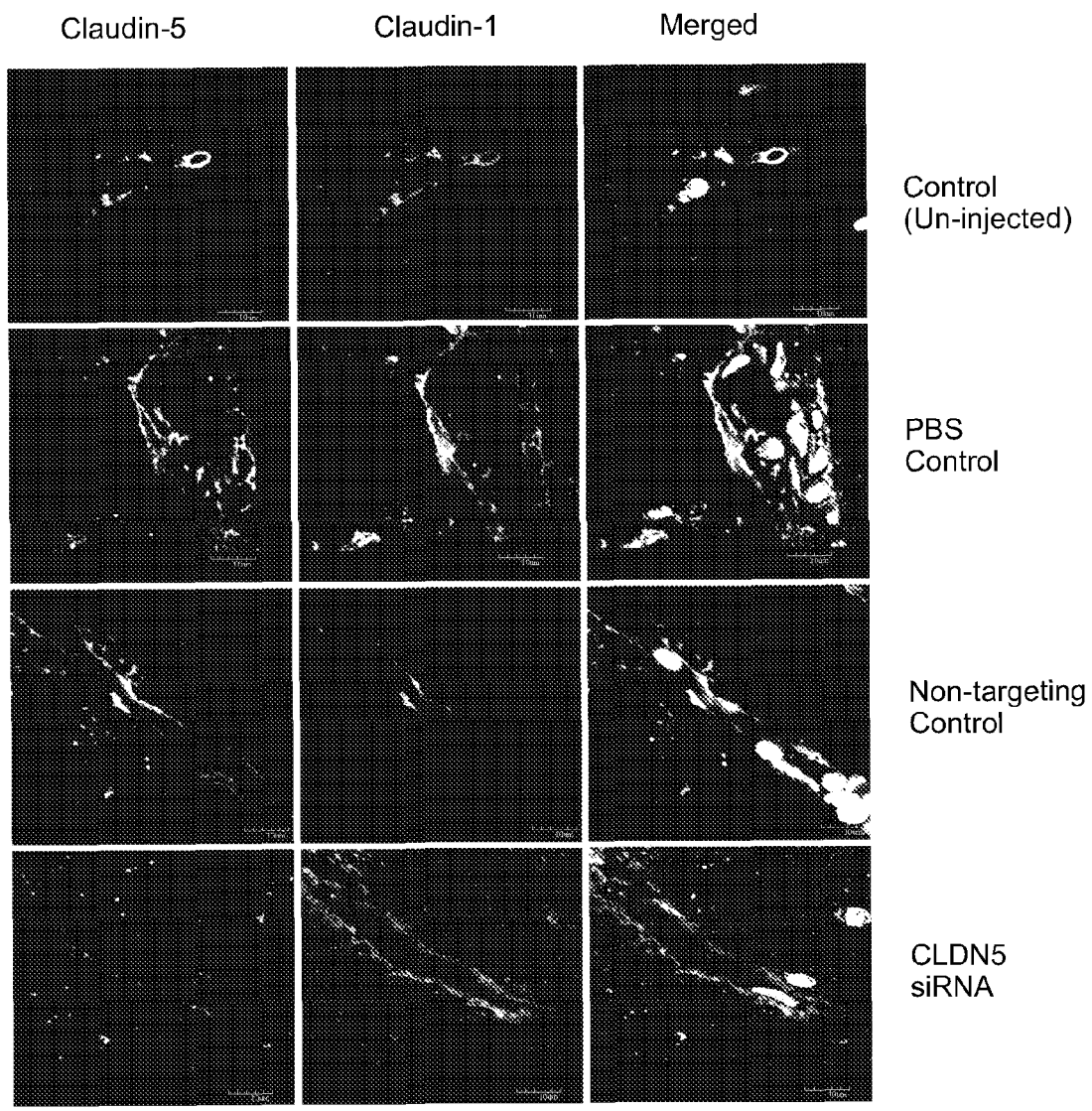
Figure 4C:
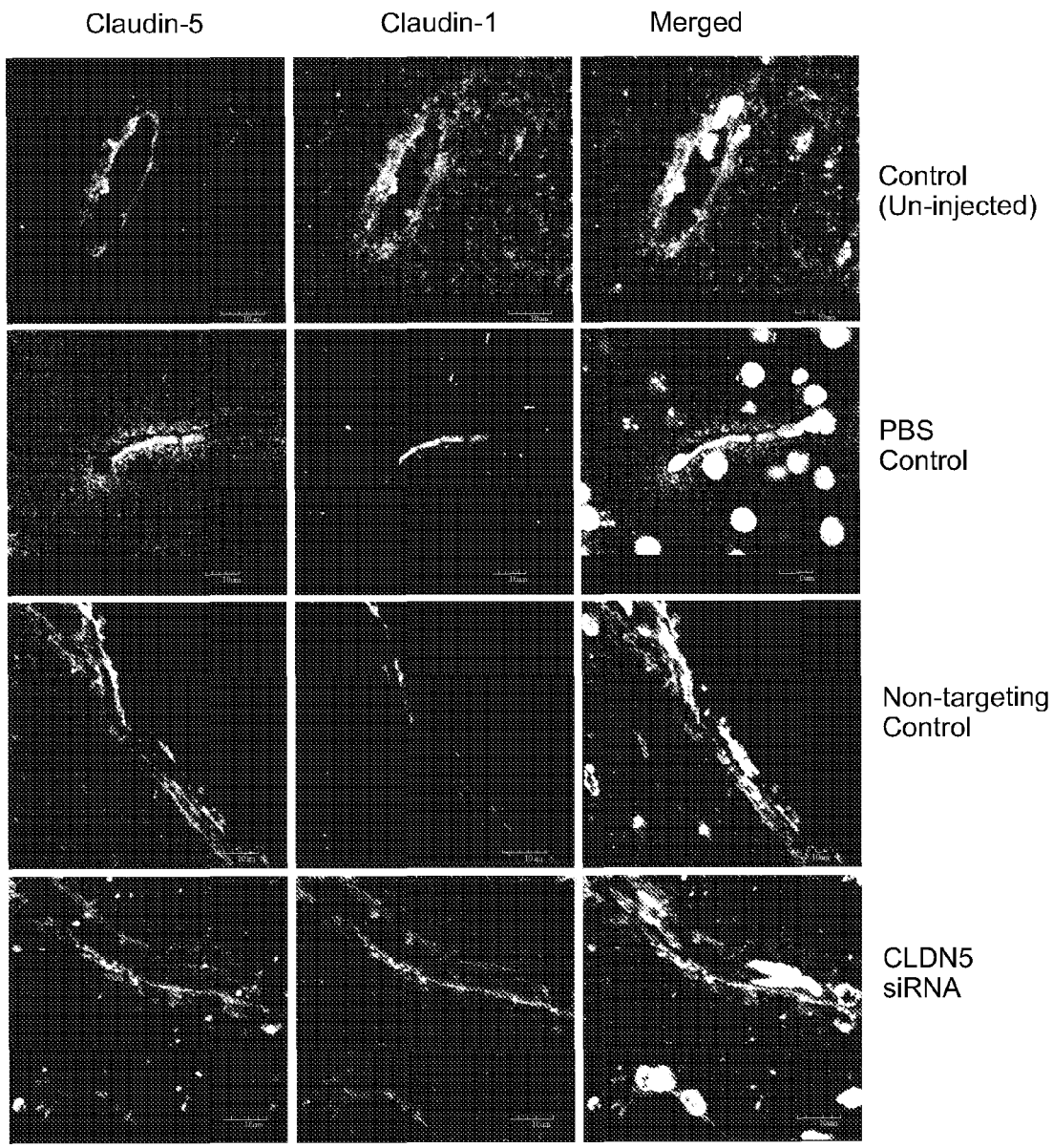
Figure 4D:
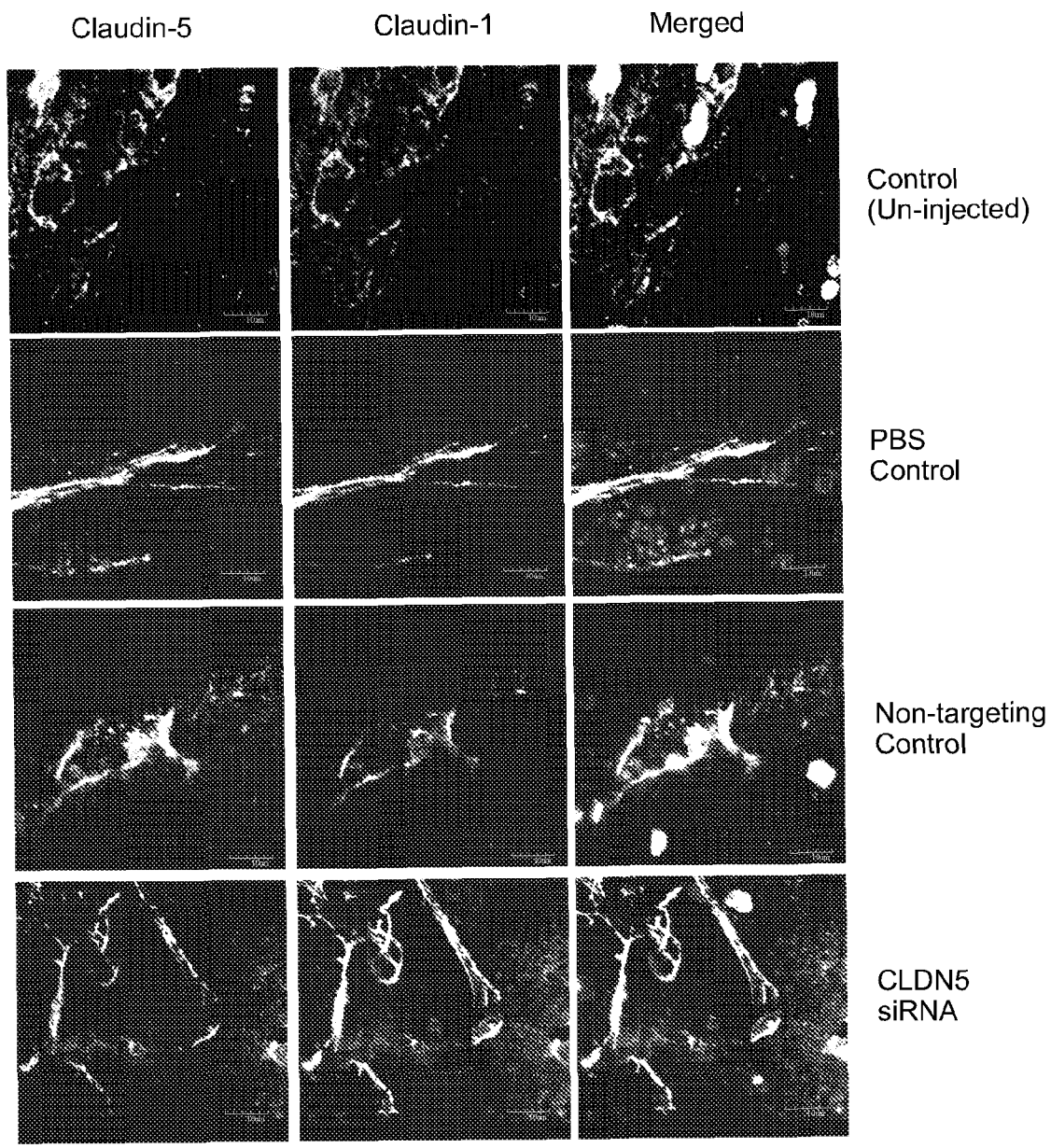

FIG. 3 shows the results of Claudin-1, Tie-2 and Occludin expression following suppression of claudin-5. Western blot analysis of claudin-1 (23 kDa) expression 24, 48, 72 hours and 1 week post delivery of claudin-5 siRNA, showed no changes at any time points. When blots were probed with an anti-Tie-2 (140 kDa) antibody, no distinct changes in the levels of expression of this endothelial cell specific tyrosine kinase receptor were observable at any time point or with any treatment (FIG. 3A). Levels of expression of the tight junction protein occludin (approximately 60 kDA) were also shown to remain un-changed at all time points post-delivery of siRNA (FIG. 3B).

FIG. 4 shows the results of Claudin-1 and Claudin-5 double immunostaining in brain cryosections. Following injection of siRNA targeting claudin-5, and using the appropriate controls, brain cryosections were stained with a rat anti-claudin-1 antibody and a rabbit anti-claudin-5 antibody. Secondary antibodies used were rat IgG (Cy3;Red) and rabbit IgG (Cy2;Green). Similar to findings in FIG. 2, the pattern of claudin-5 staining appeared highly fragmented and discontinuous 48 hours (FIG. 4B) after injection of siRNA. The appearance of claudin-5 staining 72 hours post-injection of claudin-5 siRNA was evident, yet not as intense as the control groups (FIG. 4C). At each time point post-injection, levels of expression of claudin-1 appeared to remain similar to those observed in the control groups.

Figure 5:
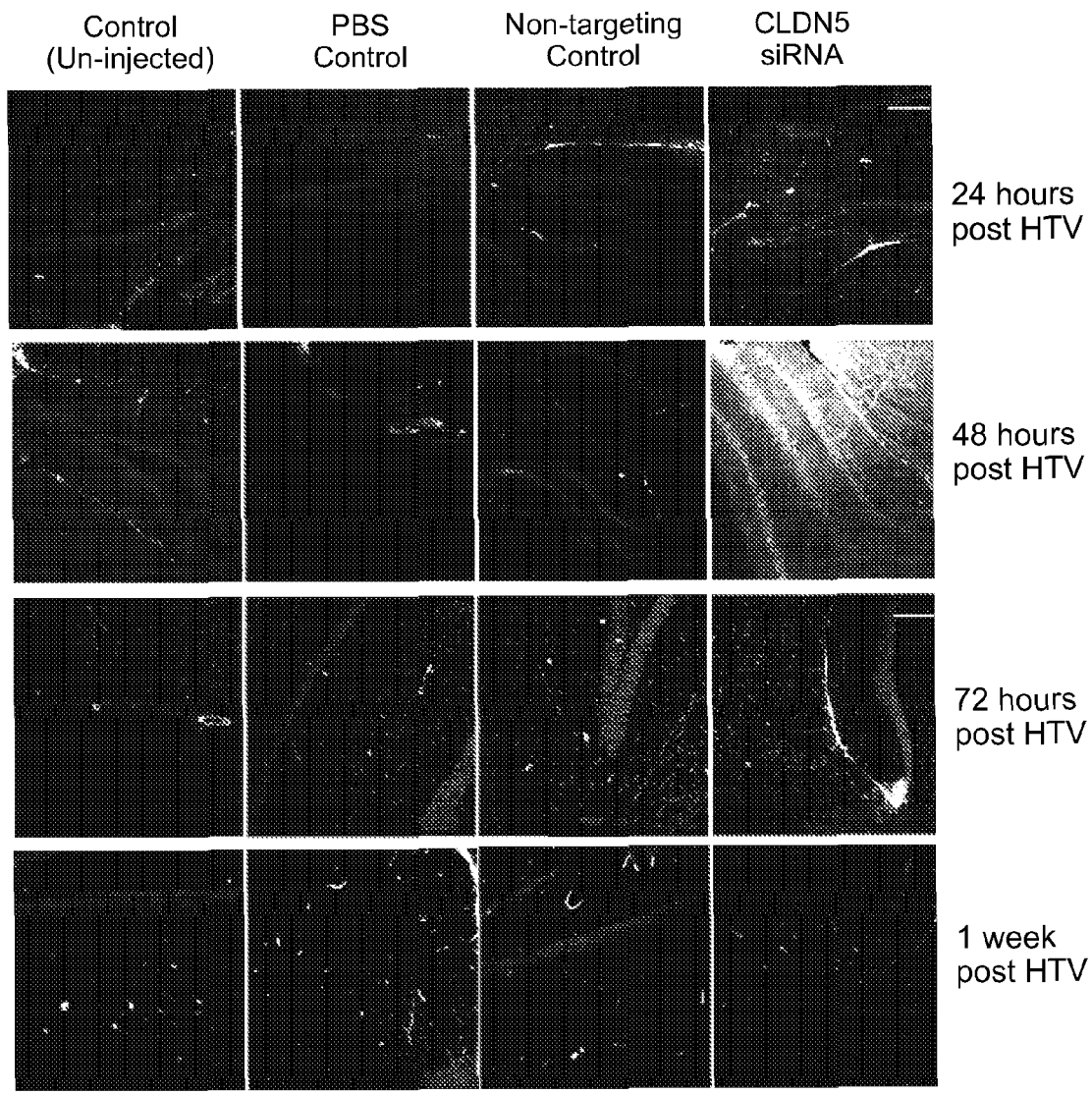

FIG. 5 shows the results of an assessment of BBB integrity to a molecule of 443 Daltons. BBB integrity was observed as green fluorescence within the microvessels in all control groups. However, 24 hours post-injection of siRNA targeting claudin-5, fluorescence detected was diffuse and outside of the microvessels in contrast to the control groups at the same time point. At 48 hours post-injection of claudin-5 siRNA, the distribution of the biotinylated molecule was abundant in the brain parenchyma, while this permeability was still evident 72 hours post-delivery of siRNA when compared to the control groups. In mice 1 week post-injection of siRNA targeting claudin-5, it was observed that the biotinylated reagent did not deposit in the parenchyma following perfusion for 5 minutes. The EZ-Link™ Sulfo-NHS-Biotin was observed within the microvessels of the brain. Scale bar for 24 and 48 hour time points approx 200 μm. Scale bar for 72 hour and 1 week time points approx 100 μm. All tracer experiments were repeated in mice at least 5 times.

Figure 6A:
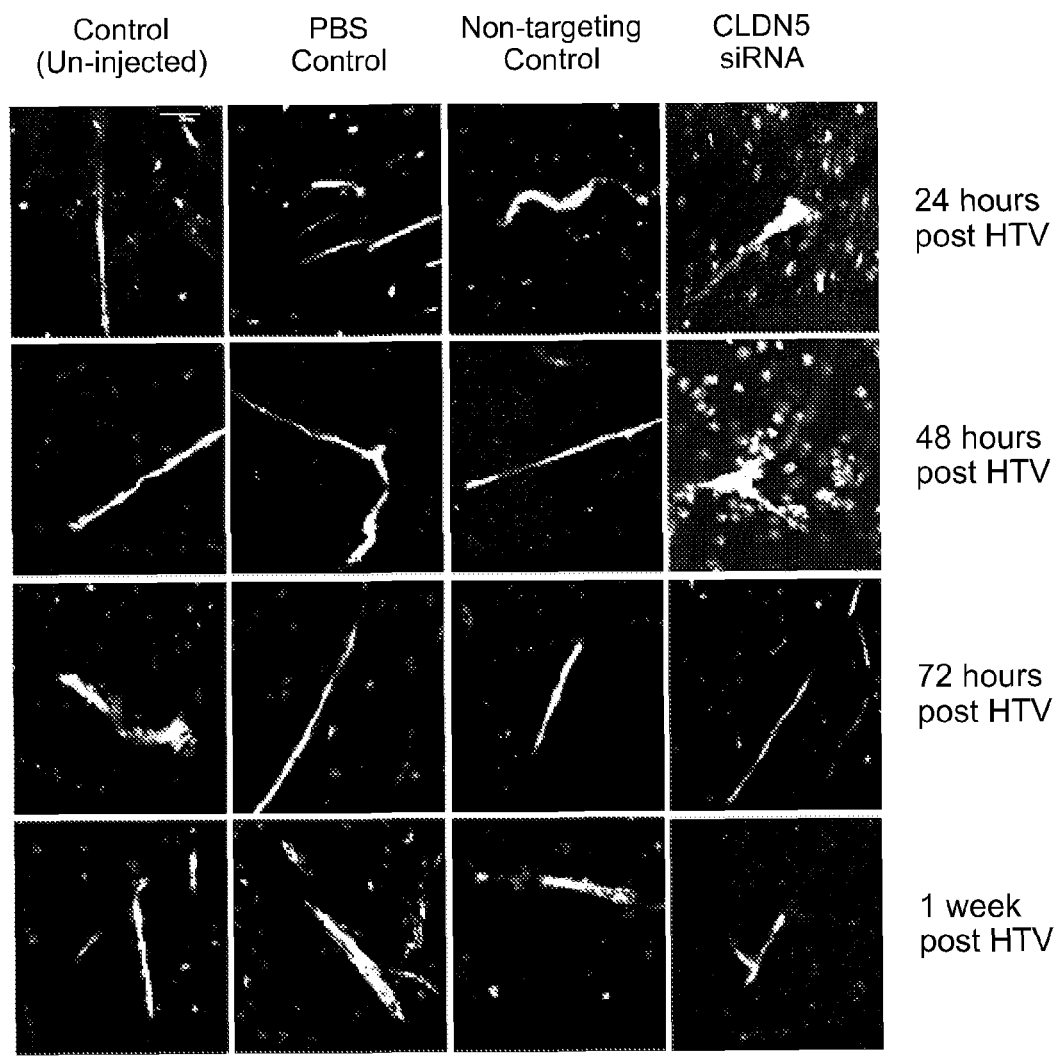

FIG. 6 show the results of extravasation of Hoechst H33342 dye from brain and retinal microvessels, by showing Hoechst 33342 and FD-4 co-perfusion 24, 48, 72 and 1 week post-hydrodynamic tail delivery of Claudin-5 siRNA. Extravasation of Hoechst H33342 from the brain microvessels was manifested by distinct staining of nuclei in surrounding neural and glial cells 24 hours and 48 hours post delivery of claudin-5 siRNA when compared to control groups. This extravasation was not evident in sections 72 hours or 1 week post-injection of siRNA targeting claudin-5. No extravasation of FD-4 was observed in the brain parenchymal tissue at any time point following siRNA injection, or in the control groups. This highlights the size-selective nature of RNAi-mediated targeting of claudin-5. Scale bar approx. 20 μm (FIG. 6A).

Figure 6B:
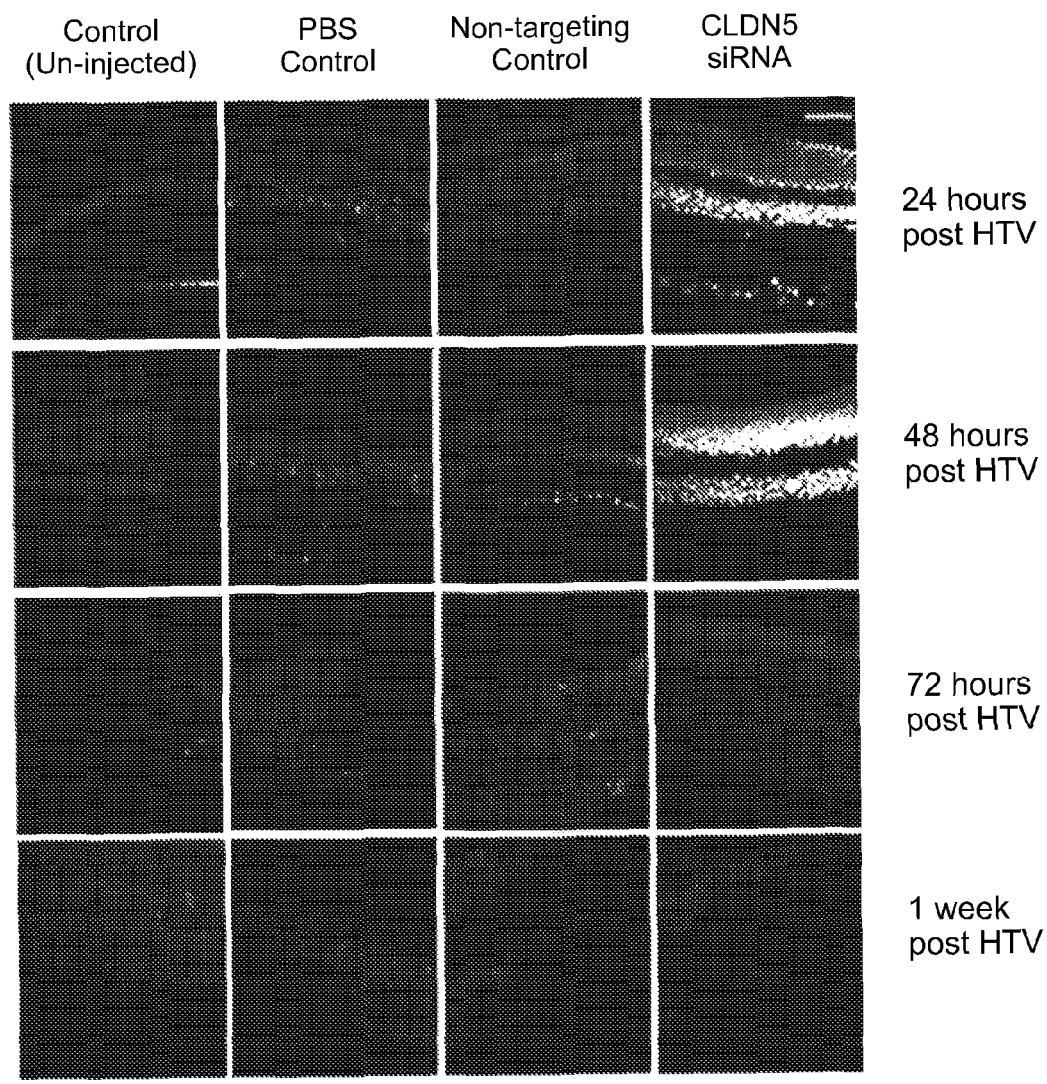

Extravasation of Hoechst was also evident in 12 μm retinal cryosections, with the Inner Nuclear Layer (INL) appearing stained at 24 hours and distinct Outer Nuclear Layer (ONL) staining at 48 hours post delivery of CLDN5 siRNA. In all control groups, Hoechst staining was manifested solely in the nuclei of retinal blood vessels which diffuse within the retina as far as the Outer Plexiform Layer (OPL). Scale bar approx. 20 μm. (IPL) Inner Plexiform Layer; (GCL) Ganglion Cell Layer (FIG. 6B).

FIG. 7A shows the results of an MRI Scan post injection to assess the blood brain barrier integrity in vivo. The magnetic resonance imaging (MRI) contrasting agent Gd-DTPA was used to ascertain BBB integrity in mice following ablation of claudin-5 transcripts compared to the control groups—un-injected control, PBS injected control and non-targeting (Rhodopsin) siRNA injected control mice. The image to the left of the figure is the contrasting of the mouse brain before injection of Gd-DTPA, while the image to the right is the contrasting of the mouse brain following injection of Gd-DTPA. The images are taken coronally moving from the ventral aspect of the brain to the dorsal aspect (Lower images), with intervening images showing contrasting within the hippocampal and cortex regions. At 24 & 48 hours post-injection of claudin-5 siRNA, it was observed that Gd-DTPA crossed the BBB and was deposited within the brain. Strong contrasting was also observed in the eye when compared to the control groups of animals at the 48 hour time point but not at the other time points. The most significant infiltration and deposition of Gd-DTPA (742 Da) into the parenchyma occurred at 24 and 48 hours post-injection of siRNA targeting claudin-5 (All MRI scans were repeated a minimum of twice). This infiltration of the contrasting agent was not present in the control groups of mice, nor was it present in mice 72 hours or 1 week post-injection of siRNA targeting claudin-5.

Figure 7B:
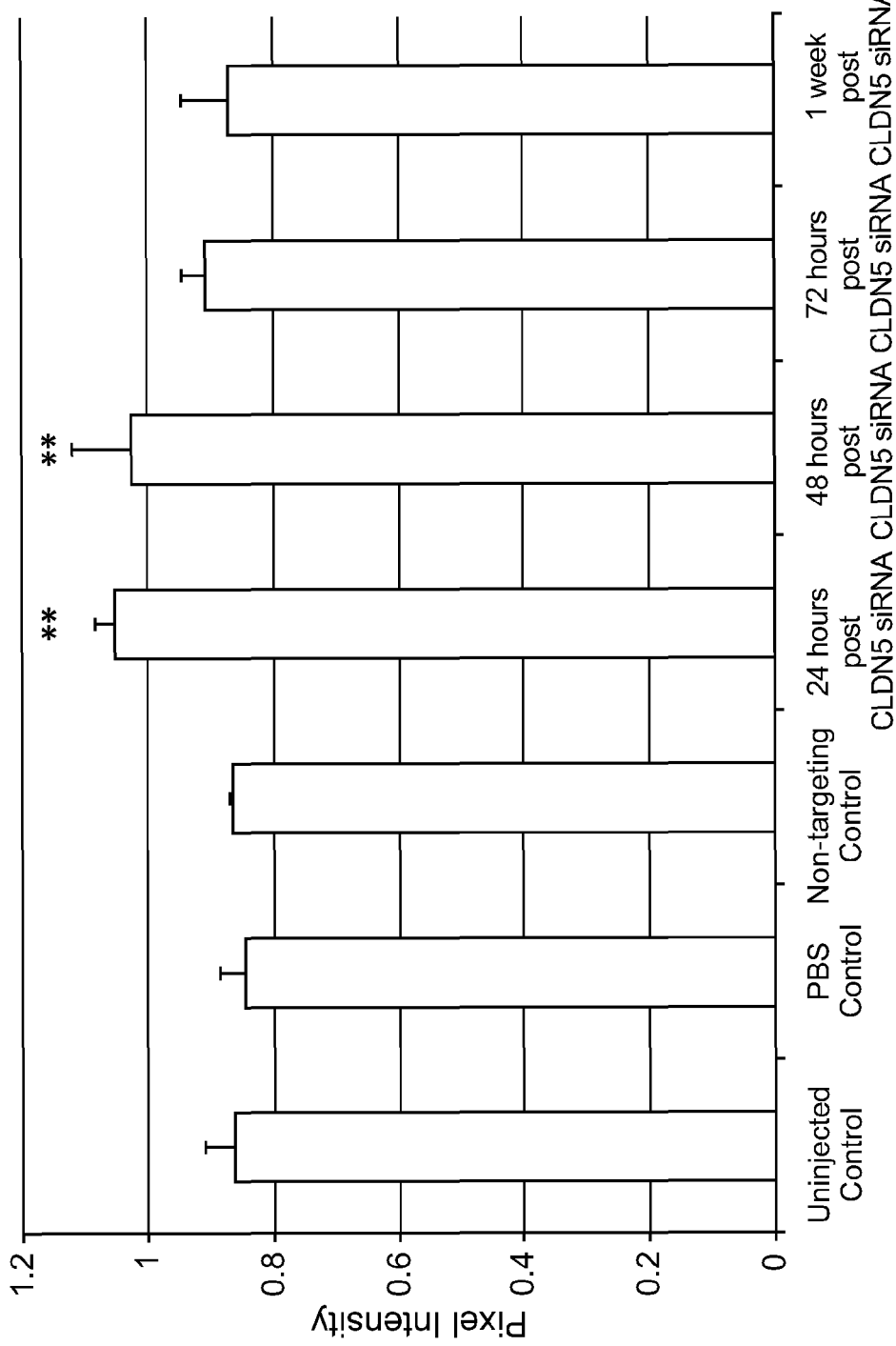

FIG. 7B shows the results of densitometric analysis of MRI imaging in mouse brain following systemic administration of siRNA targeting claudin-5. Densitometric analyses of MRI scans in selected regions of the Cerebellum, Hippocampus and Cortex for each time point and with each treatment were combined and are represented as a bar chart in FIG. 7B. There was a significant increase in contrasting within these regions at 24 hours ($P<0.05$) and 48 hours ($P<0.05$) post injection of claudin-5 siRNA when compared to the control groups.

Figure 7C:
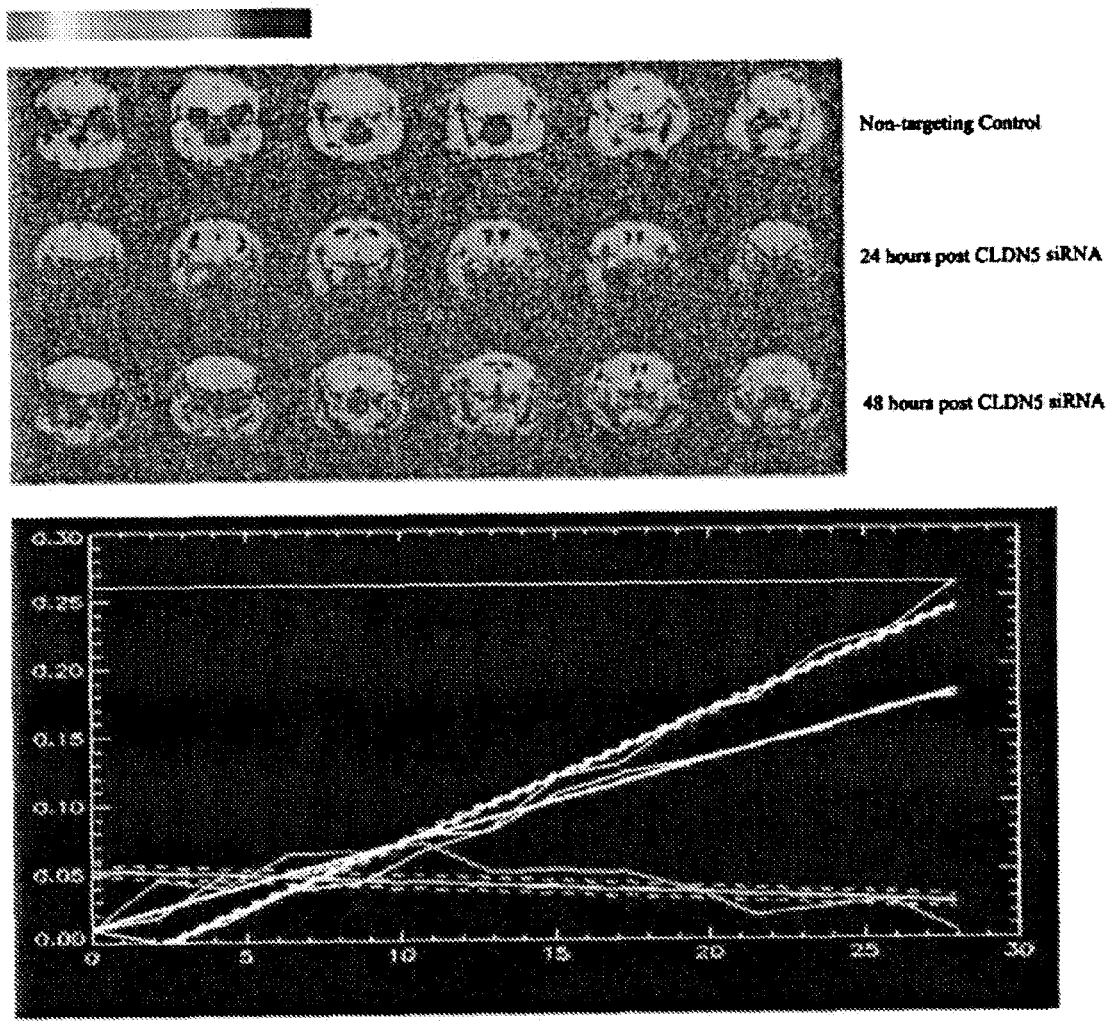

FIG. 7C shows the results of quantitative MRI imaging. The image in FIG. 7C is represented as follows; the red end denotes very little change in the slope of the linear fit, determined for every pixel in the MRI scans of mice. The green areas show some change and blue areas denote a large change in the rate of Gd-DTPA deposition. The graph below the quantitative image in FIG. 7C shows the change in intensities in left ventricle over a 28-minute timecourse after Gd-DTPA injection. The data in the graph is plotted as the natural logarithm (ln) of the signal intensity (y-axis) against time in minutes on the x-axis (each unit on the x-axis is 128 seconds long). The red line represents the non-targeting control siRNA injected mouse; the yellow line represents the 24 hours time point post-injection of siRNA targeting claudin-5; while the green line represents the 48 hour time point post-injection of claudin-5 siRNA. Thin lines=raw data of intensities at the 14 time points; Thick lines=mathematically calculated linear fit for the time points; Dotted lines=the standard error for the linear fit using chi-squared evaluation.

Figure 8:
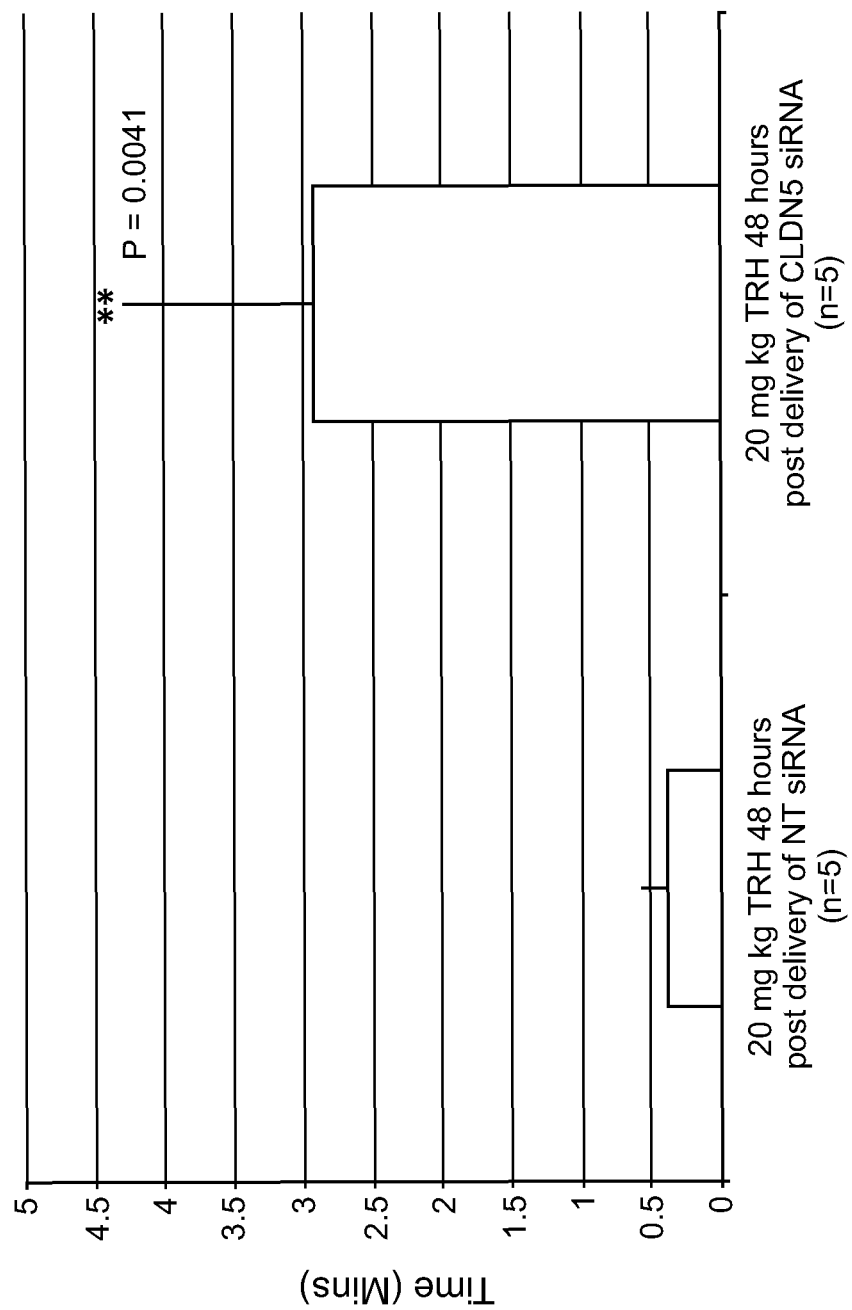

FIG. 8 shows the results of the administration of 20 mg/kg of TRH to mice following ablation of claudin-5 protein. This graph outlines the distinct changes in mobility observed upon administration of 20 mg/kg TRH in mice 48 hours after tail vein injection of a non-targeting siRNA and 48 hours post-injection of siRNA targeting claudin-5. When the BBB was compromised, the behavioural output following TRH injection 48 hours post delivery of siRNA targeting claudin-5 was manifested by a significant cessation of mobility that remains for up 5 times longer than that observed in the non-targeting control mice (**$P=0.0041$).

Figure 9:
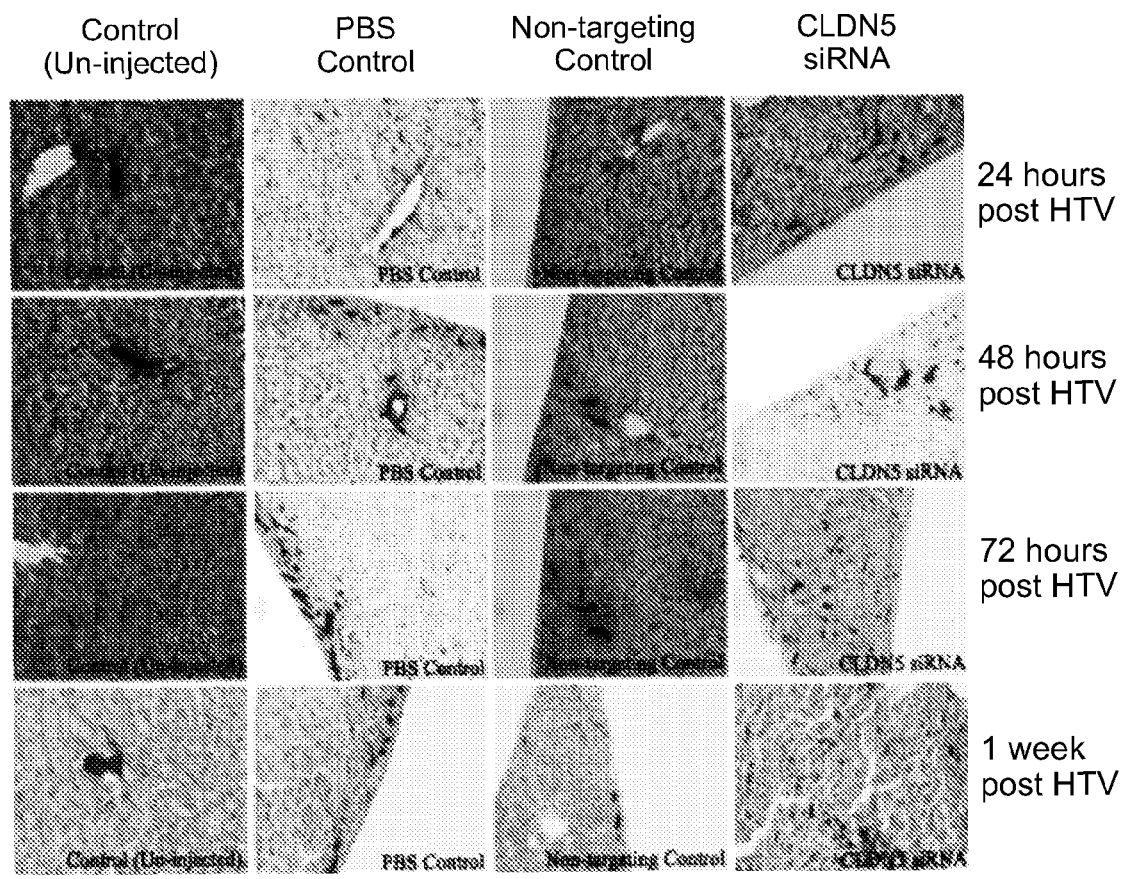

FIG. 9 shows endothelial cell morphology in liver cryosections. 12 μm cryosections of mouse liver were prepared following injection of siRNA targeting claudin-5 and using the appropriate control groups. The brown/red-rose chromogenic staining in the sections represents the *Griffonia simplicifolia*-isolectin B4 binding in liver microvasculature and specifically the endothelial cells lining this microvasculature. In all sections and all treatments, the microvasculature of the liver appears similar and un-disrupted. Sections were counterstained with Hematoxylin.

Figure 10:
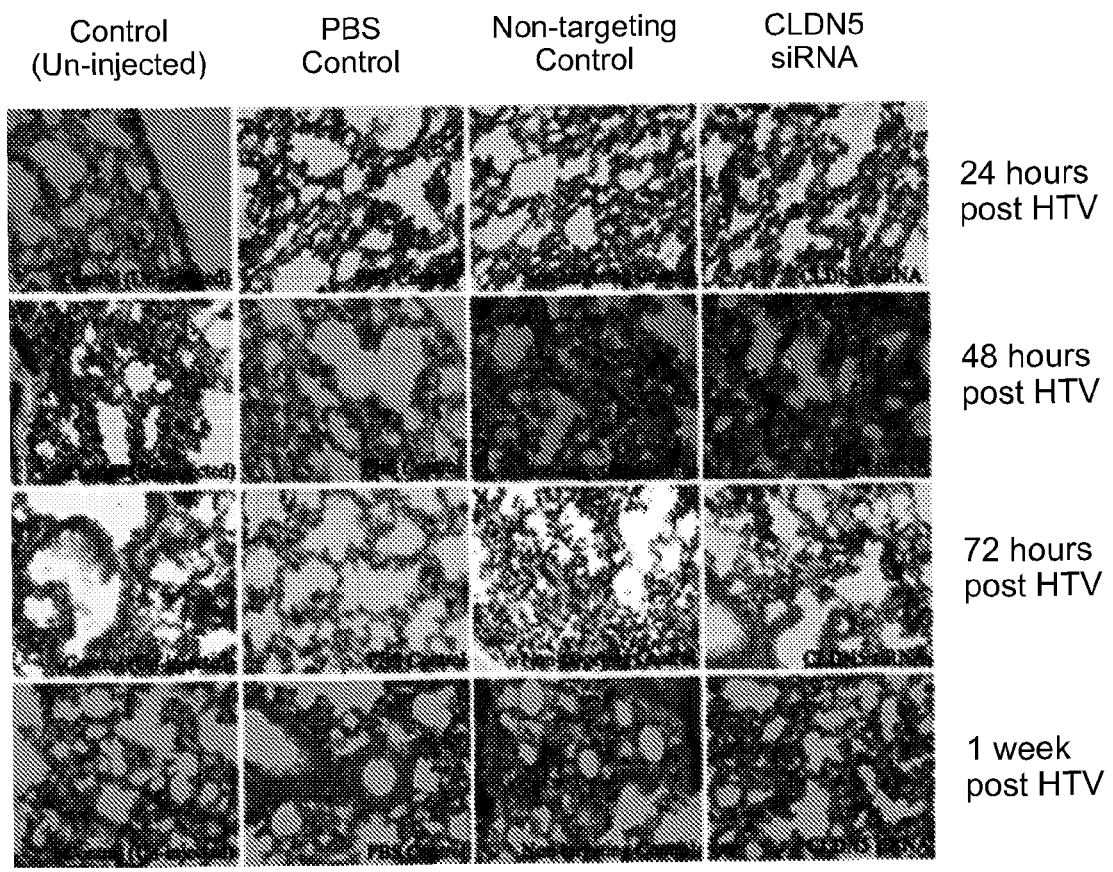

FIG. 10 shows endothelial cell morphology in lung cryosections. Cryosections of mouse lung were stained with HRP-conjugated *Griffonia simplicifolia*-isolectin B4. It is clear that the lung tissue is highly perfused with microvessels; however the morphology of these vessels remains un-changed in all experimental groups and at all time points post-injection. Sections were counterstained with Hematoxylin.

Figure 11:
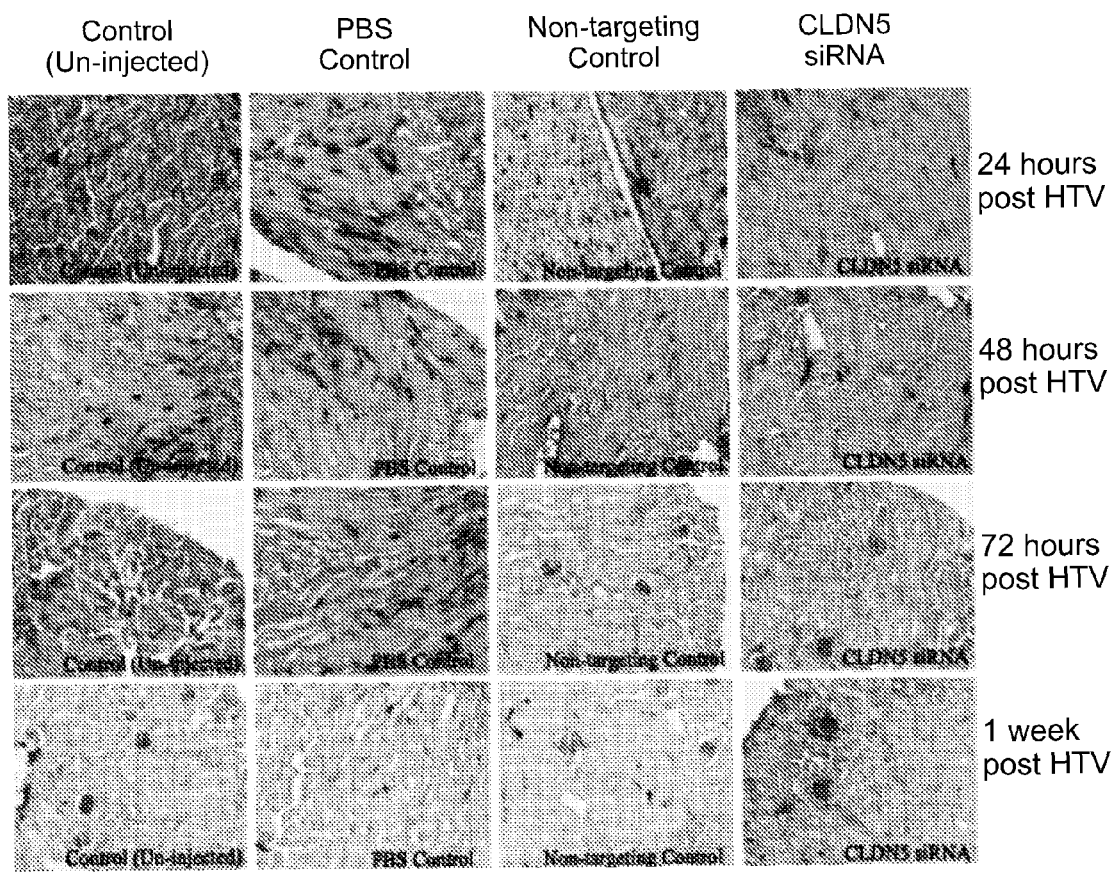

FIG. 11 shows endothelial cell morphology in kidney cryosections. Mouse kidney cryosections were prepared following injection of siRNA and employing the appropriate control groups and subsequently stained with HRP-conjugated *Griffonia simplicifolia*-isolectin B4. Brown/red-rose staining showed intact kidney microvessels in all treatments and at all time points post siRNA injection. Sections were counterstained with Hematoxylin.

Figure 12:
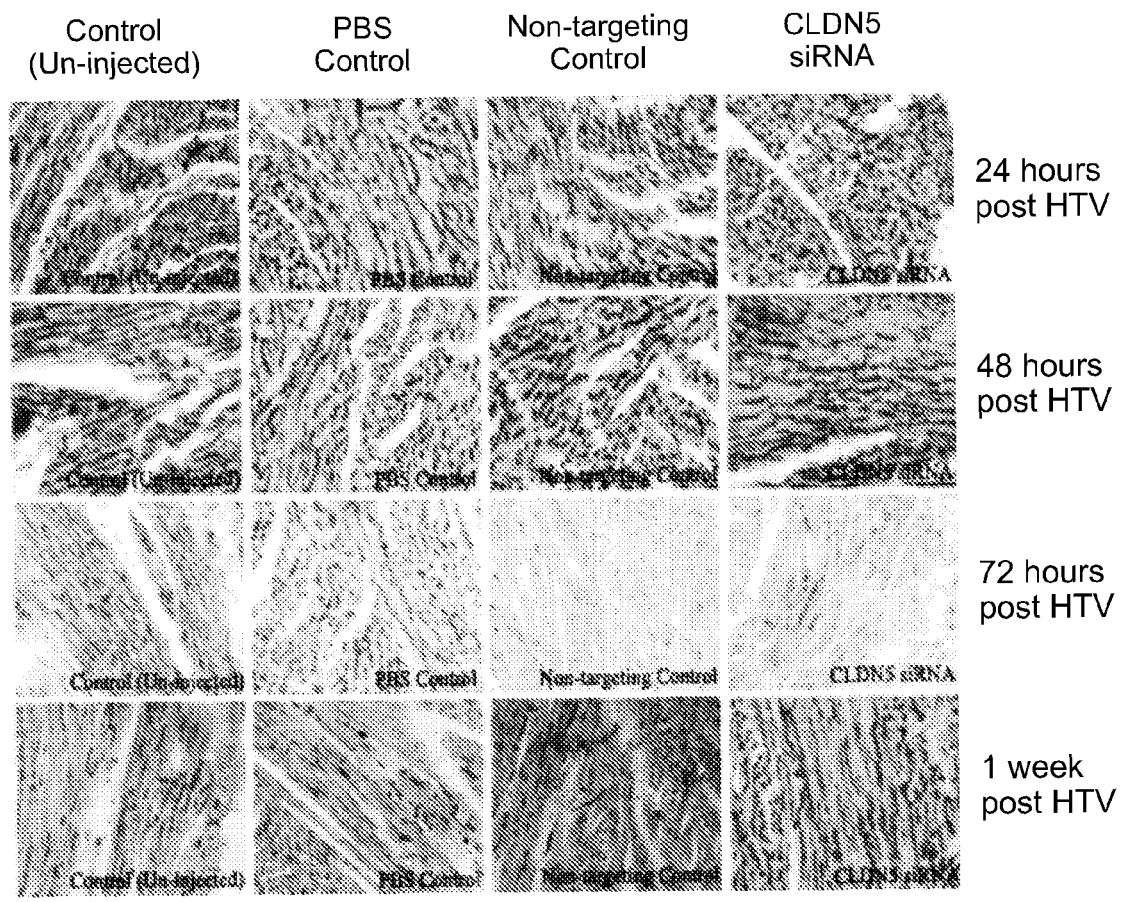

FIG. 12 shows endothelial cell morphology in heart cryosection. Mouse hearts were dissected following delivery of siRNA at 24, 48, 72 hours and 1 week, and using appropriate controls. 12 μm sections were prepared and following staining with *Griffonia simplicifolia*-isolectin B4, heart associated microvessels showed similar morphology at all time points and with all siRNA treatments. Sections were counterstained with Hematoxylin.

Figure 13:
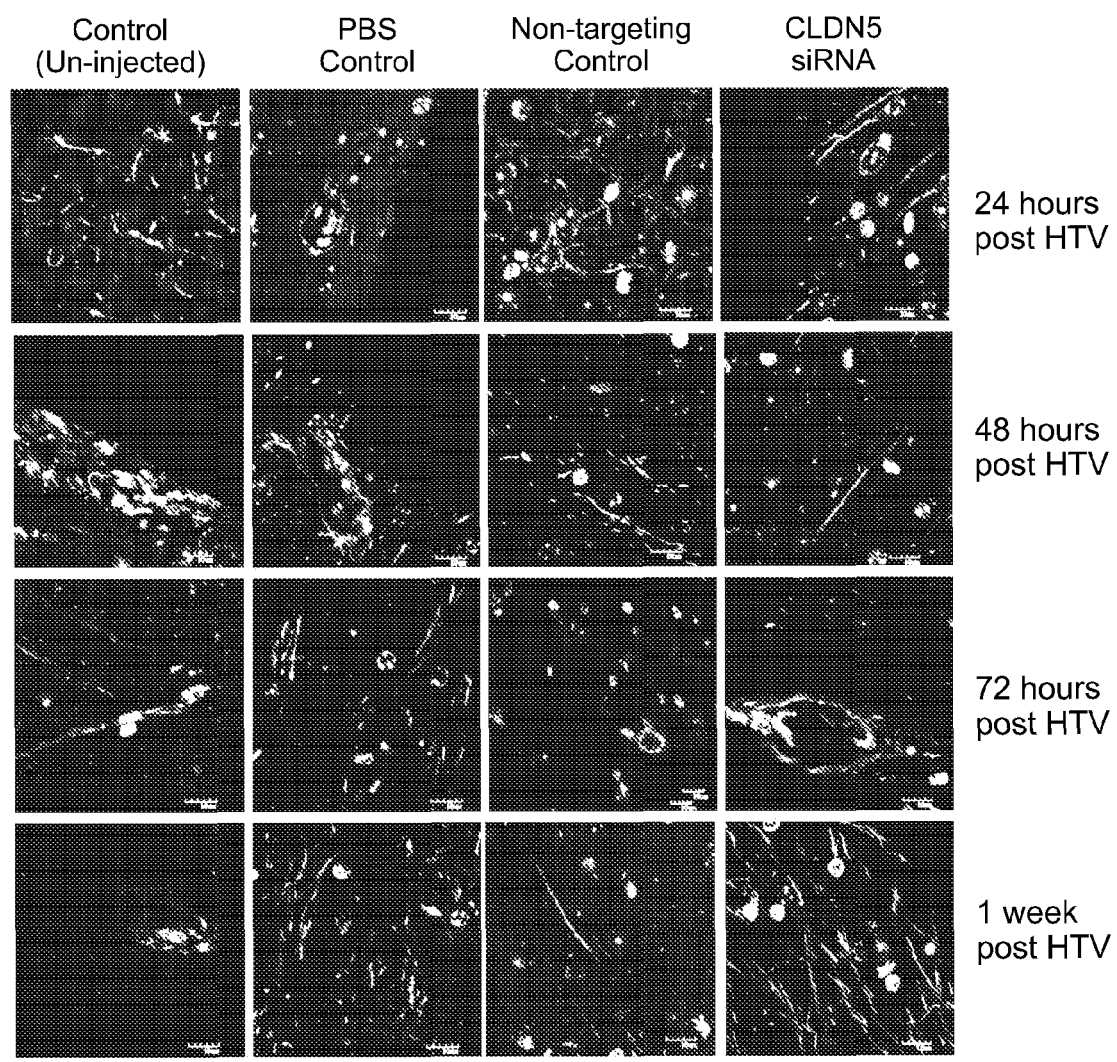

FIG. 13 shows immunohistochemical analysis of occludin expression in brain cryosections. Immunohistochemical analysis of occludin expression and localisation in the microvessels of the brain revealed a continuous and distinct pattern of staining in the microvasculature of all mice and at all time points (Red; Alexa 568=Occludin; Blue-DAPI=nuclei).

Figure 14:
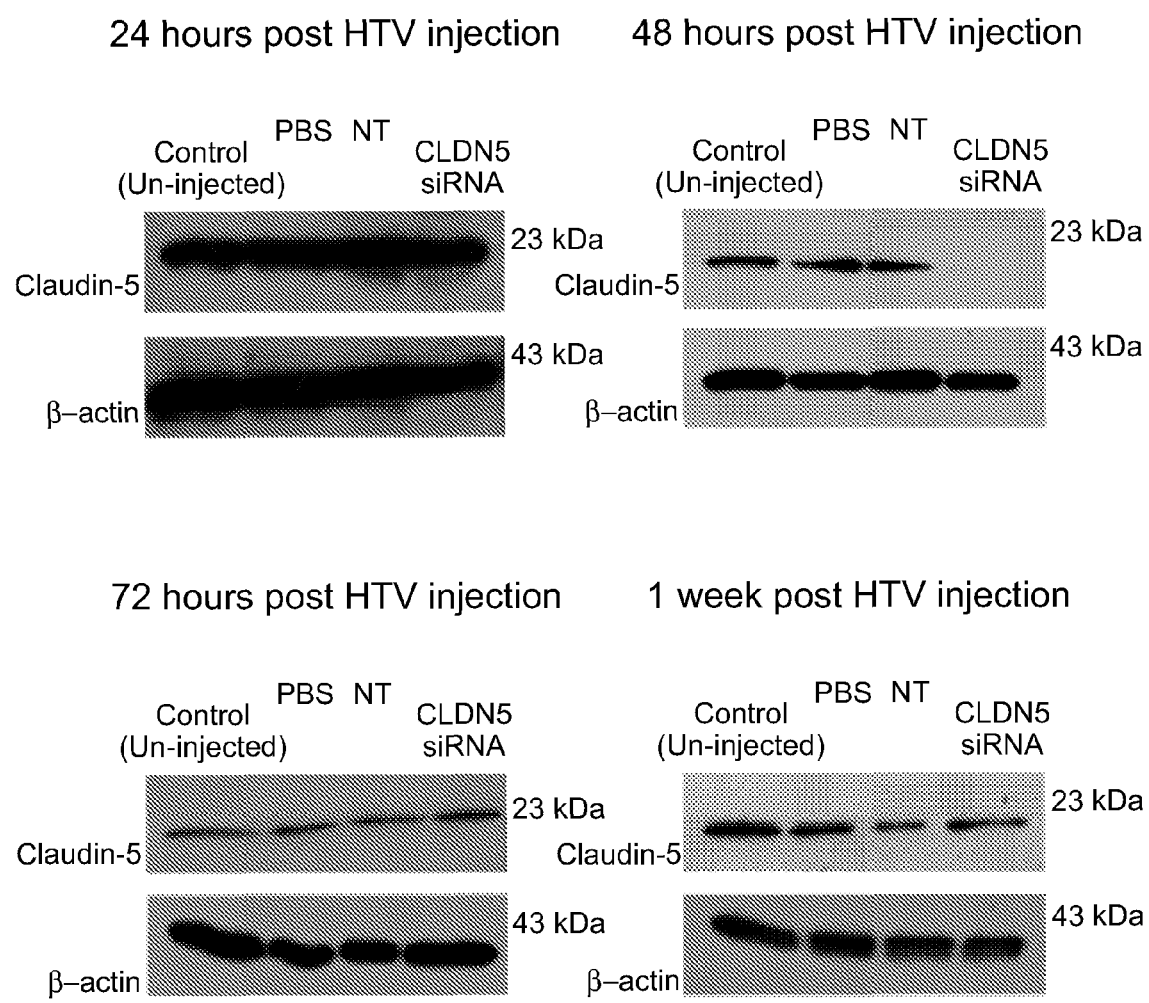

FIG. 14 shows the results of Claudin-5 suppression in the retina following siRNA injection. Western blot analysis of claudin-5 expression in retinal protein lysates showed decreased expression 48 hours post hydrodynamic tail vein injection of siRNA directed against claudin-5. Levels of expression were observed to return to levels similar to un-injected, PBS-injected and non-targeting siRNA injected mice.

Figure 15:
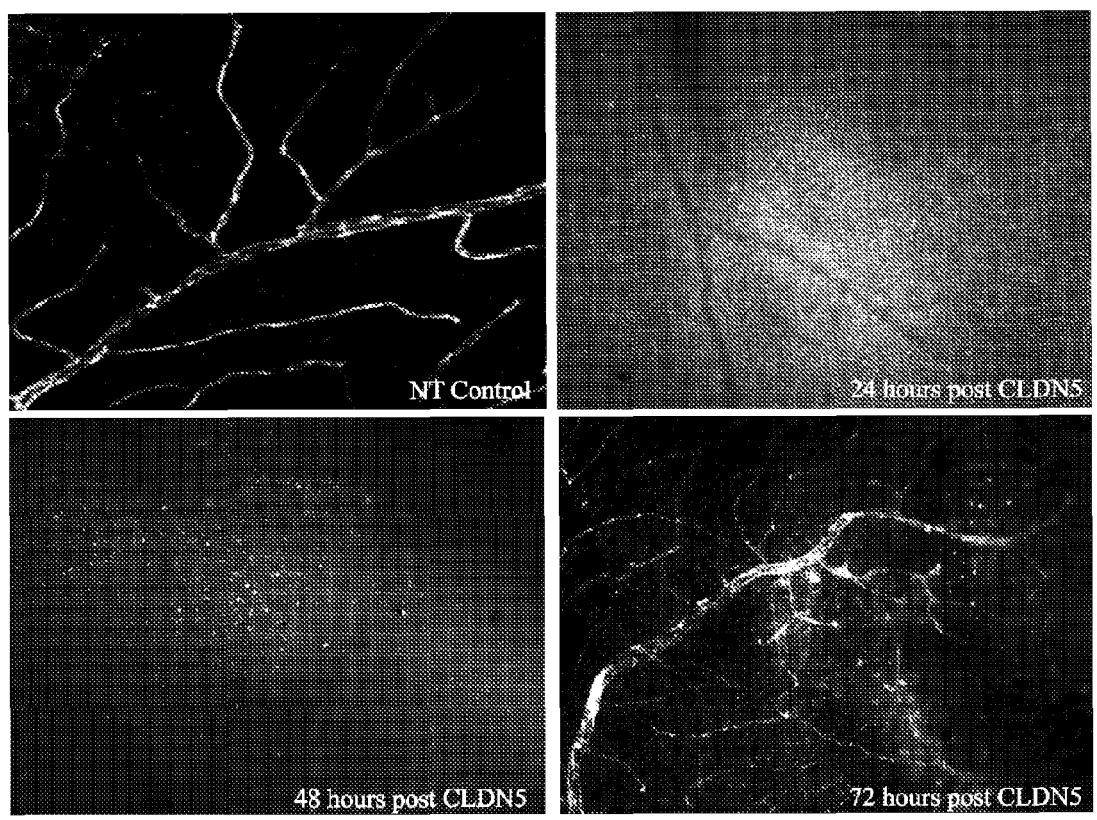

FIG. 15 shows the results of Claudin-5 expression in retinal flatmounts. Immunohistochemical analysis of claudin-5 expression in retinal flatmounts from mice receiving a non-targeting siRNA, and mice 24, 48 and 72 hours post claudin-5 siRNA injection showed a decreased localisation of claudin-5 at the periphery of endothelial cells lining the retinal microvessels. This decreased expression of claudin-5 was concomitant with increased retinal microvessel permeability.

Figure 16:
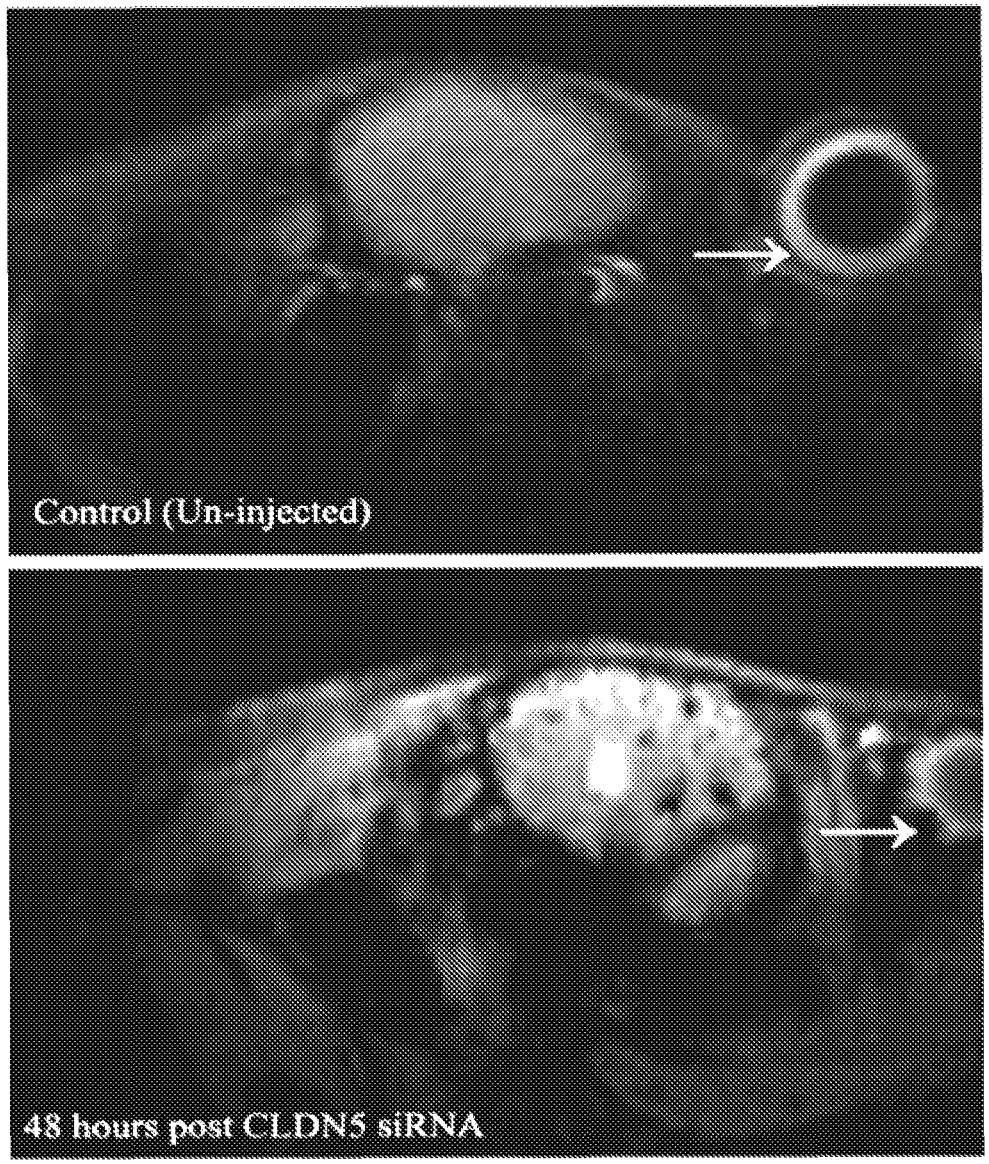

FIG. 16 shows the results of MRI analysis of Gd-DTPA diffusion across the iBRB. Following contrast enhanced MRI-analysis; it was evident that the iBRB was compromised in mice 48 hours post-injection of siRNA targeting claudin-5. This manifested as increased contrasting within the vitreous of the eye as Gd-DTPA passed from the vasculature to the extravascular spaces.

Figure 17:
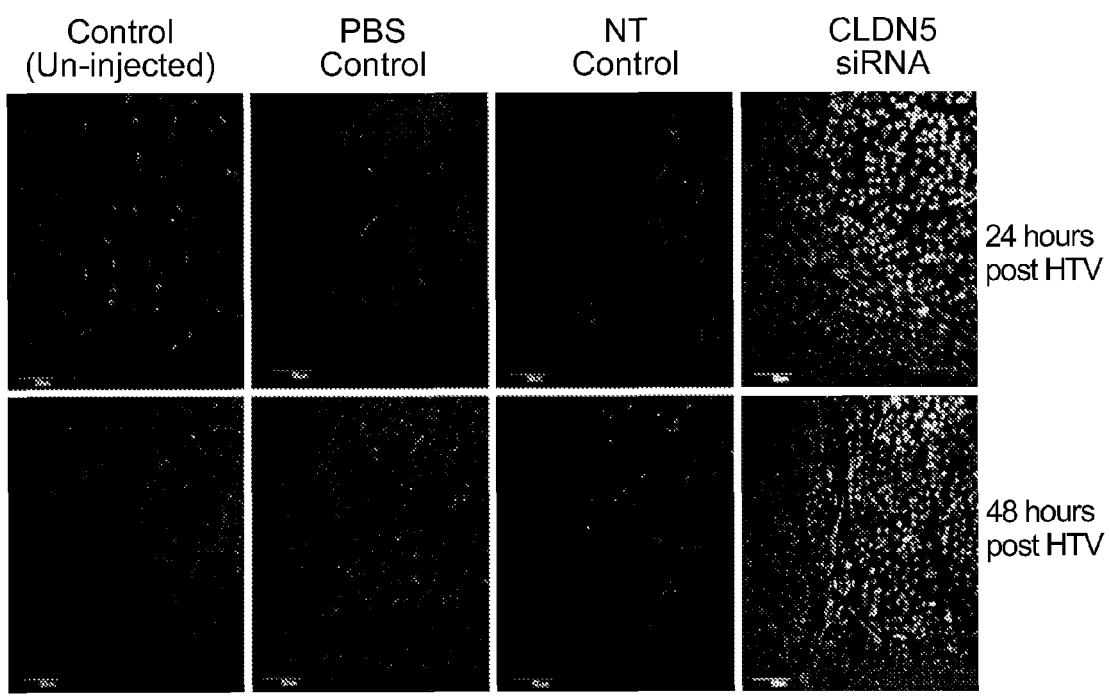

FIG. 17 shows the results of retinal flatmounts following perfusion of mice with Hoechst 33352 (562 Da). Following perfusion of mice with Hoechst 33352, retinas were dissected out and flatmounted. Hoechst 33352 was shown to stain extravascular nuclei in the retinas of mice 24 and 48 hours post hydrodynamic tail vein injection of siRNA targeting claudin-5 when compared to un-injected mice, mice receiving PBS alone or mice receiving a hydrodynamic tail vein injection of a non-targeting siRNA.

FIG. 18 shows ERG results after GTP injections in IMPDH-/- mice. Rod responses in a wild-type C-57 mouse were observed to be approximately 793 uV in both the left eye and the right eye. In an 11 month old IMPDH-/- however, the rod responses were observed to be 50.8 uV and 2.48 uV in the right eye and left eye respectively. Following suppression of claudin-5 however, and injection of GTP at the point of doing a subsequent ERG, the rod tracings were shown to increase significantly, giving b-waves of 193 uV and 121 uV respectively for the right and left eyes. This increase in rod response were observed in a further 3 IMPDH-/- mice post-suppression of claudin-5 and injection of GTP.

Figure 19:
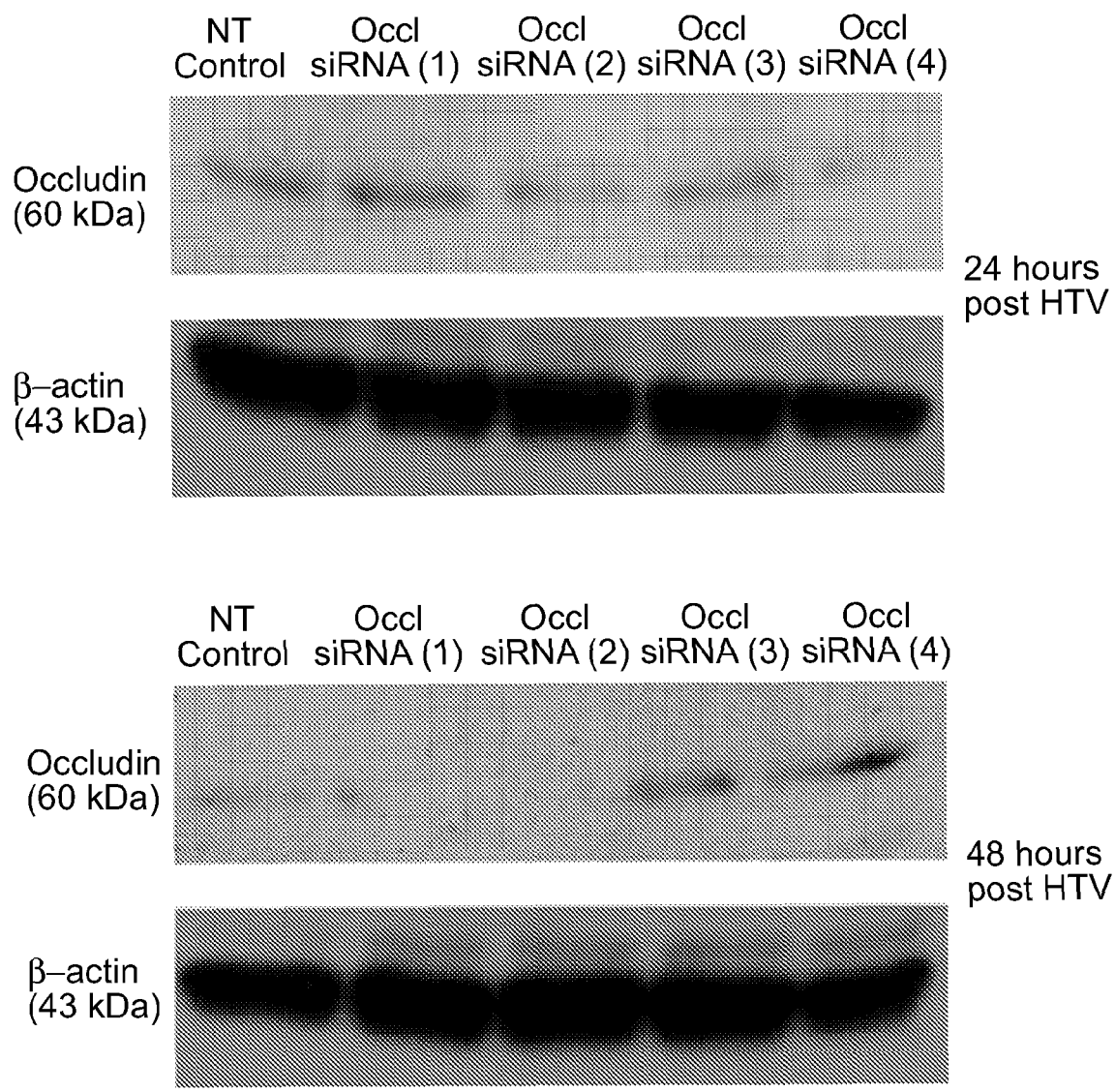

FIG. 19 shows the results of Western blot analysis of occludin expression following hydrodynamic tail vein delivery of occludin siRNA. Levels of expression of occludin were shown to decrease 24 hours post injection of occludin siRNA (4) and to a lesser extent with occludin siRNA (2). However, 48 hours post injection of occludin siRNA (1) and occludin siRNA (2), levels of occludin expression were significantly decreased compared to mice receiving an injection of a non-targeting siRNA.

Figure 20:
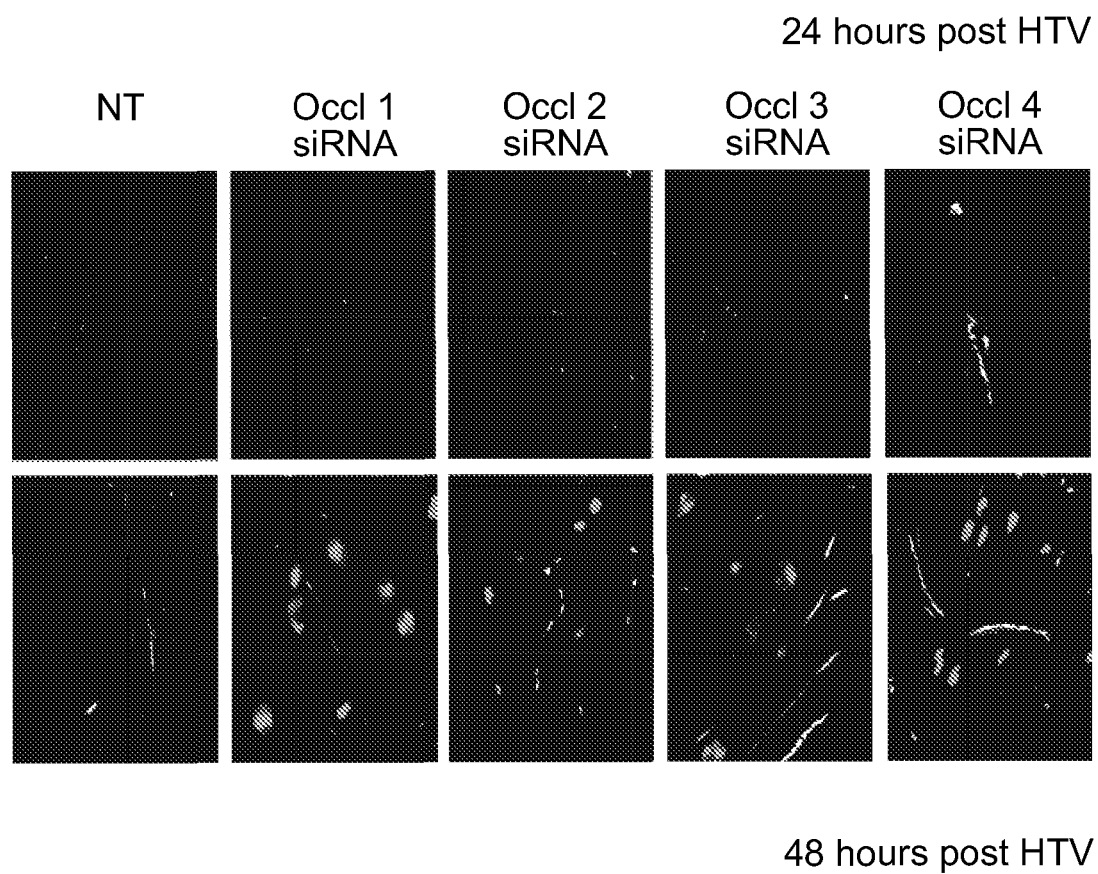

FIG. 20 shows the results of Occludin immunohistochemistry following hydrodynamic delivery of occludin siRNA. The continuous pattern of staining of occludin in the brain microvasculature was observed to be disrupted 24 hours post-injection of occludin siRNAs. This discontinuous pattern of staining was also evident at the 48 hour time-point for occludin siRNAs (1) and (2). However the pattern of staining 48 hours post-injection of occludin siRNAs (3) and (4) had returned to levels similar to those observed in the non-targeting controls.

Figure 21:
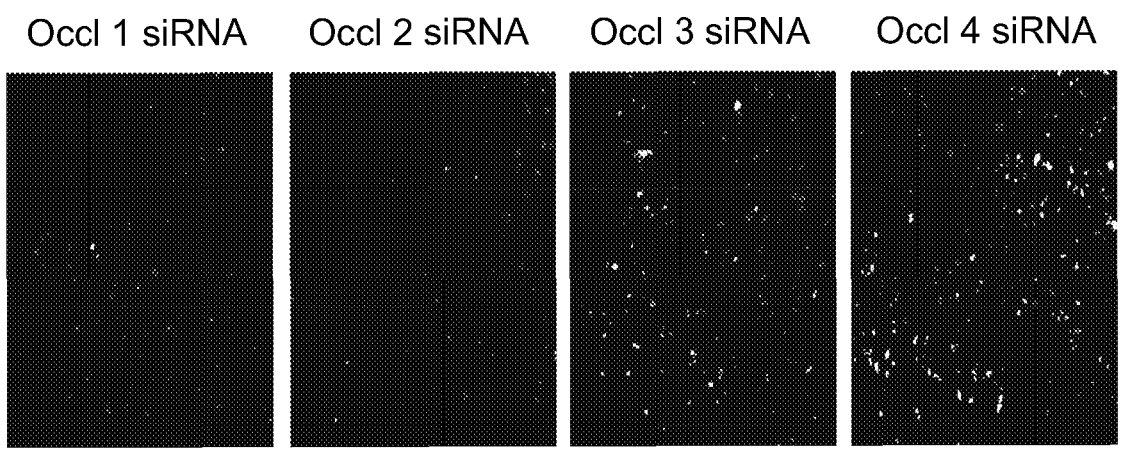

FIG. 21 shows the results of Albumin immunohistochemistry following suppression of occluding. Immunohistochemical analysis of albumin in brain vibratome sections revealed extravascular albumin 24 hours post-injection of siRNAs numbered (3) and (4). This suggests that 24 hours post siRNA injection, the paracellular pathway has been compromised enough to allow for the passage of molecules up to 70 kDa cross the BBB. Blue staining with Hoechst perfusion gives evidence for BBB compromise to a molecule of 562 Da.

Figure 22:
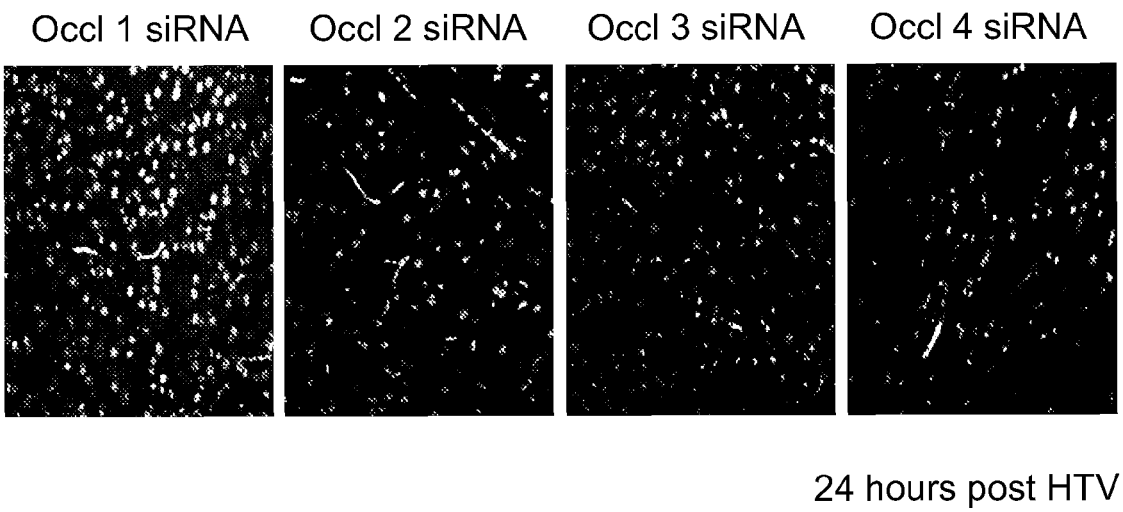

FIG. 22 shows the results of immunoglobulin staining in brain vibratome sections following suppression of occluding. Staining of mouse brain sections for mouse immunoglobulins following suppression of occludin revealed no passage of IgG's into the brain. Mouse IgGs have a molecular weight of approximately 150000 Da and it is clear that they are still excluded from the brain when occludin is suppressed.

Figure 23:
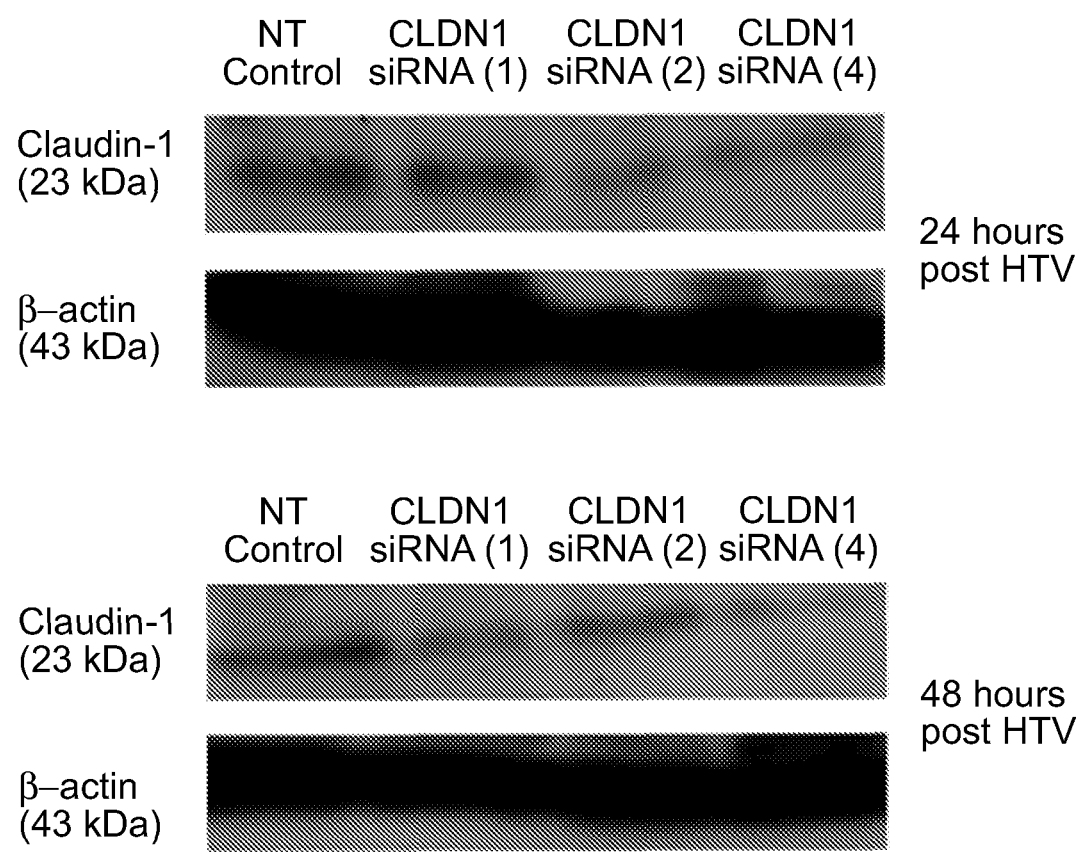

FIG. 23 shows the results of Western blot analysis of claudin-1 expression following hydrodynamic tail vein delivery of claudin-1 siRNA. Following hydrodynamic tail vein delivery of siRNA targeting claudin-1, it was observed that 24 hours post-injection, levels of claudin-1 were decreased when using siRNAs (2) and (4). This suppression was only evident in claudin-1 siRNA (4) at the 48 hour time point post-injection and although not evident at the 24 hour time-point for claudin-1 siRNA (1), this particular siRNA did significantly decrease claudin-1 expression 48 hours post injection.

Figure 24:
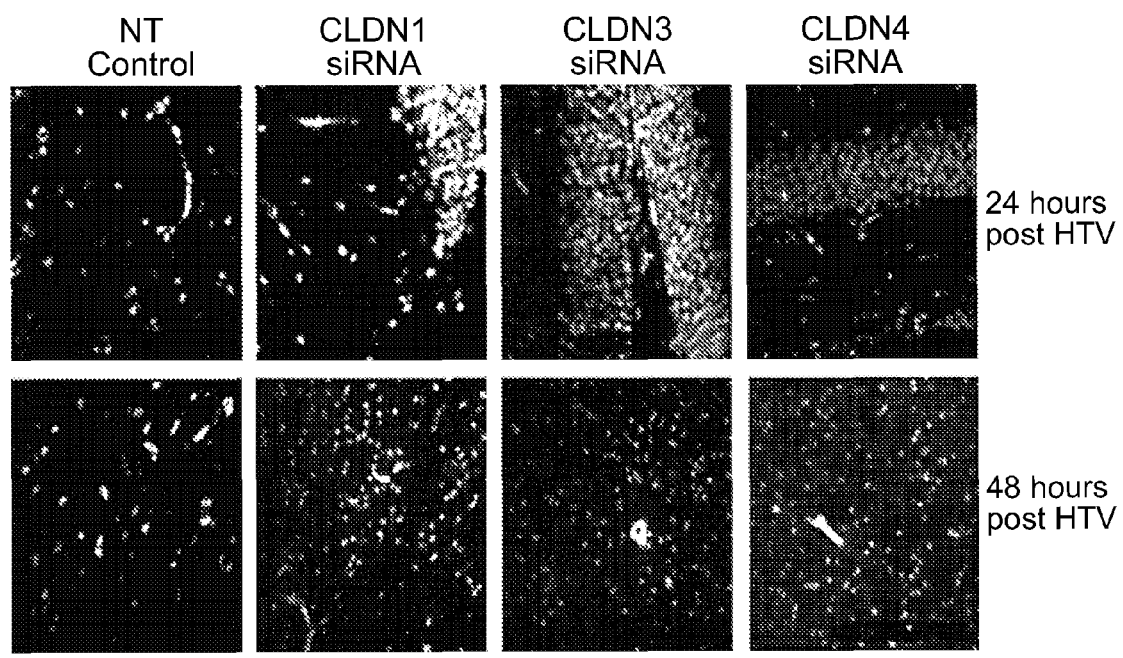

FIG. 24 shows the results of Hoechst (562 Da) and FD-4 (4,400 Da) perfusion 24 and 48 hours post hydrodynamic tail vein delivery of claudin-1 siRNA. Following delivery of a range of siRNAs targeting claudin-1, a mixture of Hoechst and FD-4 were perfused in mice and vibratome sections of the brains were prepared. It was evident that in all claudin-1 siRNAs used, there was evidence of diffusion of Hoechst from the microvessels of the brain as the surrounding neuronal cells were clearly fluorescing blue when compared to the non-targeting control mice at the same time points. In all cases, FD-4 was observed to remain within the vessels.

FIG. 25 shows the position of one of the Claudin-5 siRNA used in the experiments (siRNA anti-sense sequence -5'-GACCCAGAAUUUCCAACGUU-3' corresponding to SEQ ID No. 2), in the *Mus musculus* Claudin-5 mRNA. The target sequence for this siRNA in the *Mus musculus* Claudin-5 mRNA differs from 5'-AACGTTGGAAAT-TCTGGGTCT-3' (SEQ ID NO: 43) in that the AA on the 5' end is replaced by AG in the *mus musculus* Claudin-5 mRNA.

Figure 26:
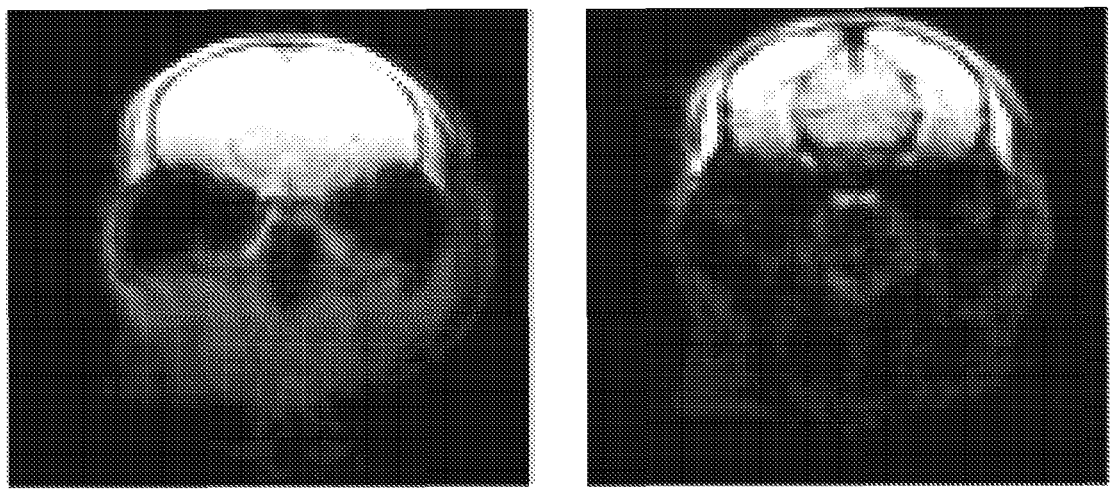

FIG. 26 shows T1-weighted MRI images of the Hippocampal region of the mouse brain 48 hours post-delivery of siRNA targeting claudin-5 clearly shows enhanced contrasting within the brain as Gd-DTPA extravasates from brain microvessels. Gd-DTPA has a molecular weight of 742 Daltons, and its permeation into the brain was only observed at 24 and 48 hours post delivery of siRNA.

Figure 27:
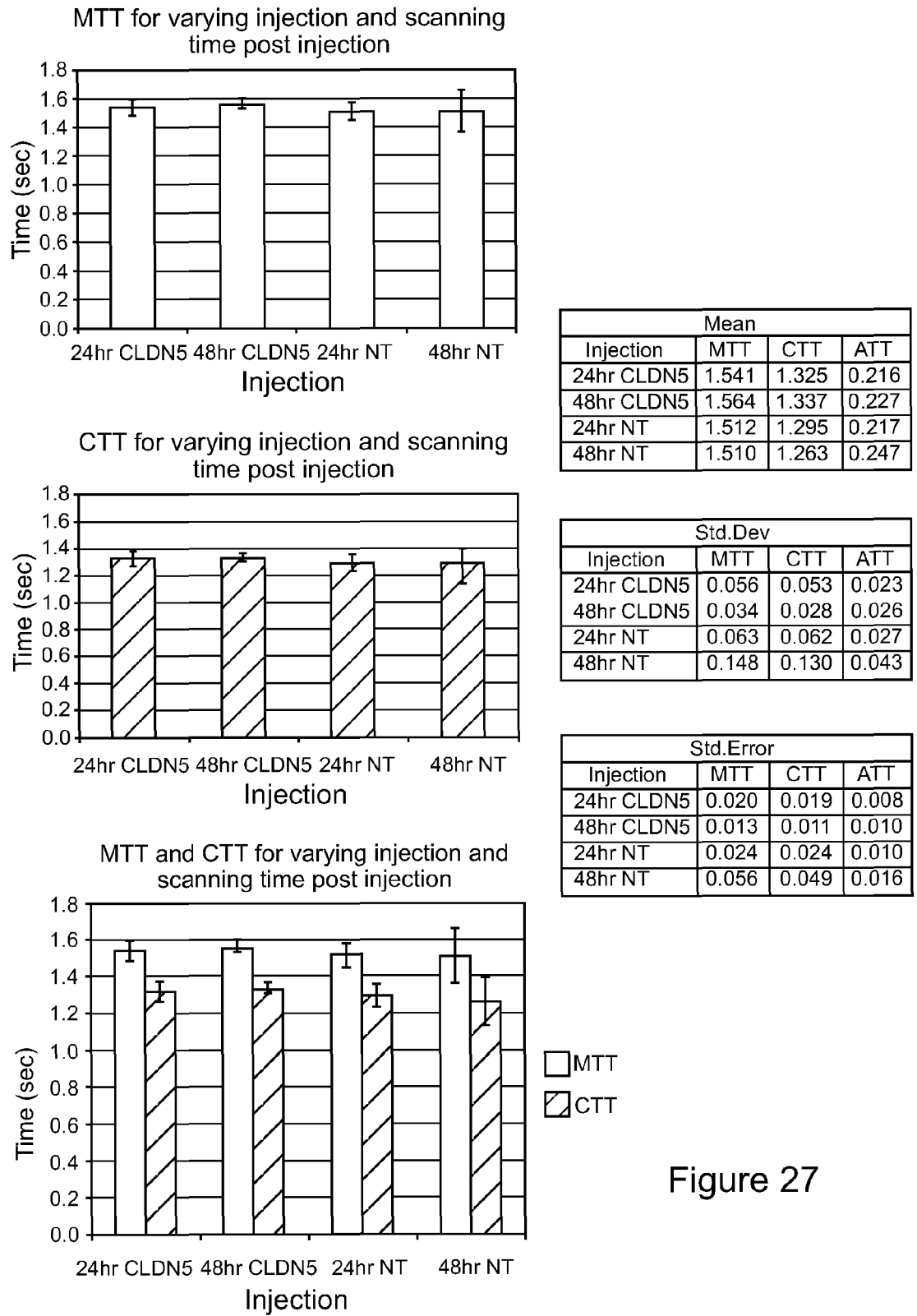

FIG. 27 shows MRI information related to blood flow/volume changes within the brains of mice 24 and 48 hours post-high volume tail vein injection of siRNA targeting claudin-5. This data gives information on two things, the mean transit time (MTT) and capillary transit time (CTT). The MTV represents the time taken for the labelled spins to travel from the labelling plane (carotid artery ~1 cm from imaging slice) to the imaging slice.

Figure 28:
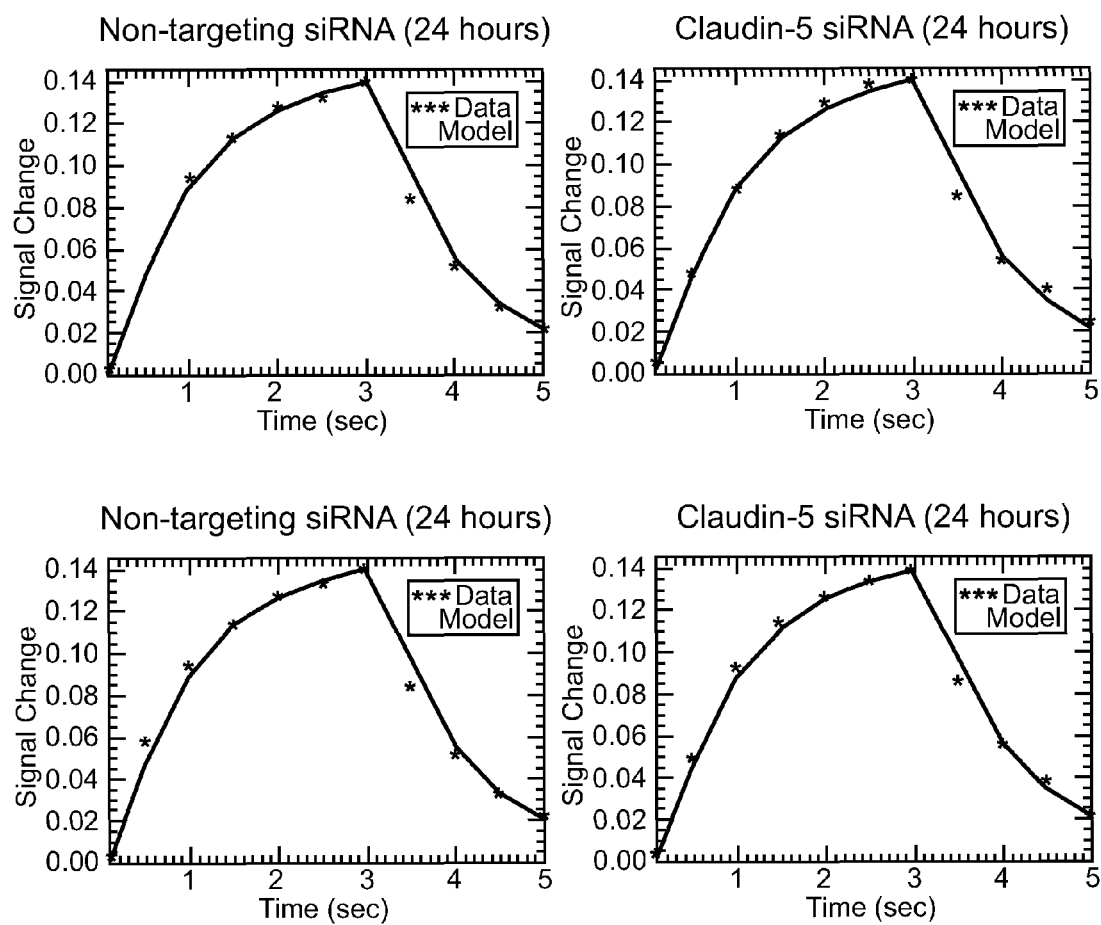

FIG. 28 shows the theoretical model for cerebral blood flow and cerebral blood volume fitted to the experimental data for each experimental group tested group. These are almost exactly the same for each group which agrees with the findings of the histograms presented in FIG. 27.

Figure 29:
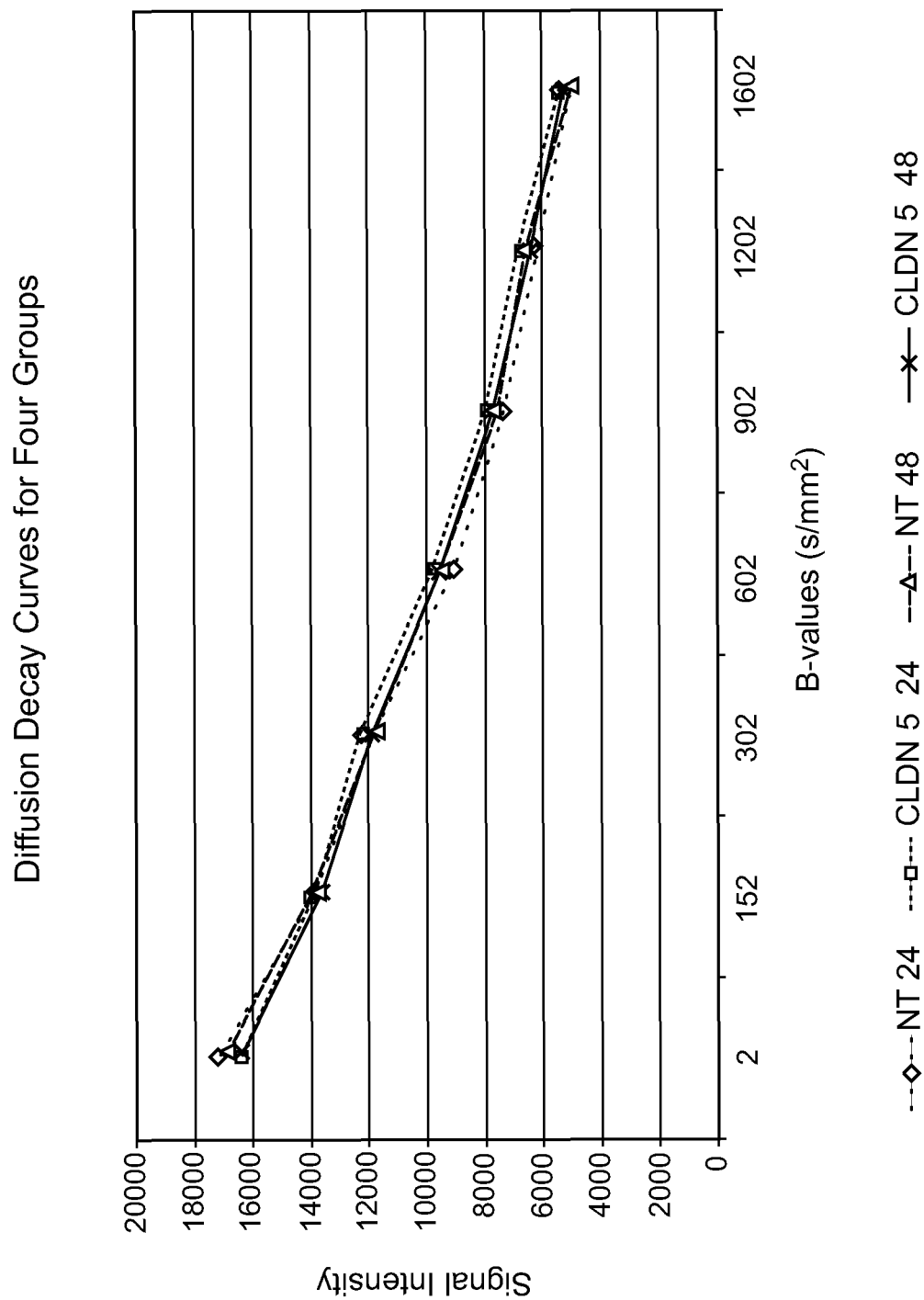

FIG. 29 shows the B-values (x-axis) plotted above with MRI signal intensity (y-axis) show no change in the rate of water diffusion in the brains of mice at 24 and 48 hours post injection of a non-targeting siRNA or siRNA targeting claudin-5. This constant rate of water diffusion from the brain to the blood suggests that the transient BBB opening in itself does not have any profound impact on water diffusion in the brains of mice.

Figure 30:
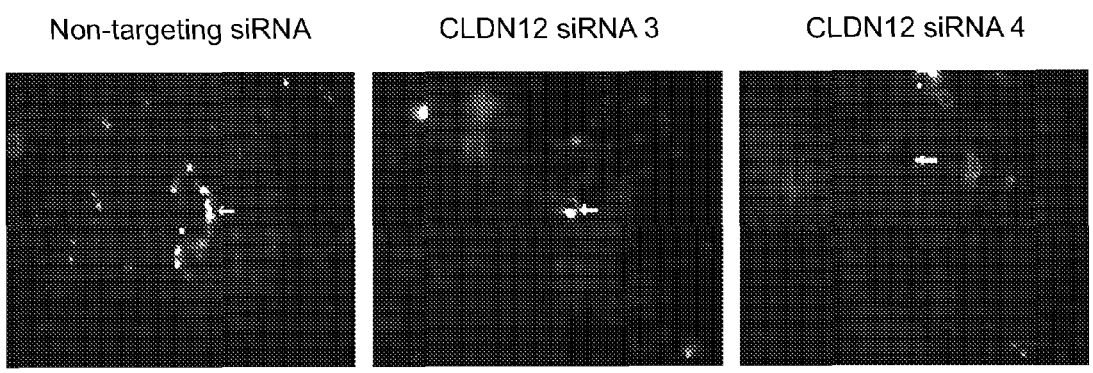

FIG. 30 shows the results after hydrodynamic tail vein injection of siRNA targeting claudin-12. The pattern of claudin-12 staining was observed to be associated with the brain microvasculature 48 hours post-injection of a non-targeting control siRNA. However, 48 hours post-injection of siRNA targeting claudin-12, levels of expression at the microvessels of the brain were shown to be decreased in both siRNAs tested (i.e., CLDN12 siRNA (3) and CLDN12 siRNA (4)).

Figure 31:
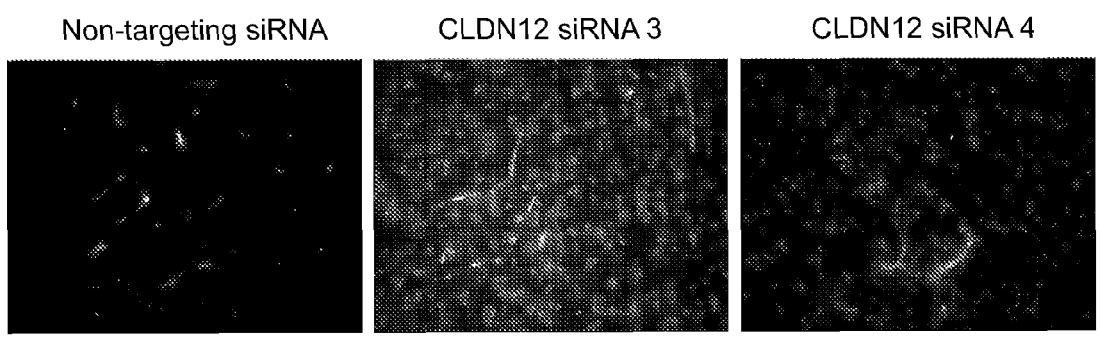

FIG. 31 shows the results following hydrodynamic tail vein injection of a non-targeting siRNA or siRNA targeting claudin-12. Mice were perfused through the left ventricle with a solution containing FITC-dextran-4 and Hoechst 33342 (562 Da). It was observed that following injection of siRNA targeting claudin-12, there was extravasation of Hoechst from the microvasculature as evidenced by staining of the extravascular nuclei. FD-4 was observed in the microvessels and in both the non-targeting siRNA and following injection of siRNA targeting claudin-12.

EXAMPLES

Example 1

In Vivo Suppression of Claudin-5 Expression at the Blood Brain Barrier of C57/Bl-6 Mice Using Systemic Hydrodynamic Tail Vein Delivery of siRNA Targeting Claudin-5

Materials
Web-Based siRNA Design Protocols Targeting Claudin-5 siRNAs were selected targeting conserved regions of the published cDNA sequences. To do this, cDNA sequences from mouse were aligned for the Claudin-5 gene and regions of perfect homology subjected to updated web-based protocols (Dharmacon, Ambion, Genescript) originally derived from criteria as outlined by Reynolds et al., (2004). Sequences of the claudin-5 siRNA used in this study were as follows:

```
                                           (SEQ ID NO: 1)
    Sense sequence:      CGUUGGAAAUUCUGGGUCUUU (SEQ ID NO: 2)
    Antisense sequence:  AGACCCAGAAUUUCCAACGUU
```

Non-targeting control siRNA targeting human rhodopsin was used as a non-targeting control since rhodopsin is only expressed in photoreceptor cells in the retina and at low levels in the pineal gland of the brain (O'Reilly, M et al., 2007):

```
                                          (SEQ ID NO: 44)
    Sense sequence:      CGCUCAAGCCGGAGGUCAA (SEQ ID NO: 45)
    Antisense sequence:  UUGACCUCCGGCUUGAGCG
```

Protocol
In Vivo Delivery of siRNA to Murine BBB by Large Volume Hydrodynamic Injection and Subsequent RNA and Protein Analyses Rapid high pressure, high volume tail vein injections were carried out (Kiang et al., 2005). Wild type C57/Bl6 mice of weight 20-30 g were individually restrained inside a 60-ml volume plastic tube. The protruding tail was warmed for 5 minutes prior to injection under a 60-W lamp and the tail vein clearly visualized by illumination from below. 20 micrograms of targeting siRNA, or non-targeting siRNA made up with PBS to a volume in mls of 10% of the body weight in grams or PBS alone, was injected into the tail vein at a rate of 1 ml/sec using a 26-gauge (26 G 3/8) needle. After 24, 48, 72 hours and 1 week, protein was isolated from total brain tissue by crushing brains to a fine powder in liquid $N_2$ and subsequently using lysis buffer containing 62.5 mM Tris, 2% SDS, 10 mM Dithiothreitol, 10 μl protease inhibitor cocktail/100 ml (Sigma Aldrich, Ireland). The homogenate was centrifuged at 10,000 g for 20 mins @4° C., and the supernatant was removed for claudin-5 analysis.

Briefly, protein samples were separated on 12% SDS-PAGE gels and transferred to nitrocellulose membrane overnight using a wet electroblot apparatus. Efficiency of protein transfer was determined using Ponceau-S solution (Sigma Aldrich, Ireland). Non-specific binding sites were blocked by incubating the membrane at room temperature with 5% non-fat dry skimmed milk in Tris-buffered saline (TBS) (0.05 M Tris, 150 mM NaCl, pH 7.5) for 2 hours. Membranes were briefly washed with TBS, and incubated with polyclonal rabbit anti-claudin-5 (Zymed Laboratories, San Francisco, Calif.) (1:500) or polyclonal rabbit anti-β-actin (Abcam, Cambridge, UK) (1:1000). Antibodies were incubated with membranes overnight at 4° C. Membranes were washed with TBS, and incubated with a secondary anti-rabbit (IgG) antibody with Horse-Radish-Peroxidase (HRP) conjugates (1:2500), for 3 hours at room temperature. Immune complexes were detected using enhanced chemiluminescence (ECL).

At the same time points post-delivery of siRNA total RNA was isolated from brains using Trizol (Invitrogen). RNA was then treated with RNase-free DNase (Promega, Madison, Wis., USA) and then chloroform extracted, isopropanol precipitated, washed with 75% RNA grade ethanol and resuspended in 100 µl RNase-free water.

Real-Time RT-PCR Analysis

RNA was analyzed by real-time RT-PCR using a Quantitect Sybr Green Kit as outlined by the manufacturer (Qiagen-Xeragon) on a LightCycler (Roche Diagnostics, Lewes, UK) under the following conditions: 50° C. for 20 min; 95° C. for 15 min; 38 cycles of 94° C. for 15 s, 57° C. for 20 s, 72° C. for 10 s.

Primers (Sigma-Genosys, Cambridge, UK) for the sequences amplified were as follows

```
CLDN5
                                          (SEQ ID NO: 46)
Forward 5'-TTTCTTCTATGCGCAGTTGG-3'

(SEQ ID NO: 47)
Reverse 5'-GCAGTTTGGTGCCTACTTCA-3'

β-actin
                                          (SEQ ID NO: 48)
Forward 5'-TCACCCACACTGTGCCCATCTA-3'

(SEQ ID NO: 49)
Reverse 5'-CAGCGGAACCGCTCATTGCCA-3'
``` cDNA fragments were amplified from claudin-5 and β-actin for each RNA sample a minimum of four times. Results were expressed as a percentage of those from the similarly standardized appropriate control experiment. The reciprocal values compared to the non-targeting control siRNA gave percentage suppression of claudin-5 expression. Mean values, standard deviations, and pooled t tests were calculated using GraphPad Prism©. Differences were deemed statistically significant at $P<0.05$.

Indirect Immunostaining for Claudin-5 Using Confocal Laser Scanning Microscopy (CLSM) for Analysis Brain cryosections were blocked with 5% Normal Goat Serum (NGS) in PBS for 20 mins at room temperature. Primary antibody (Rabbit anti-Claudin-5, Zymed, California) was incubated on sections overnight at 4° C. Following this incubation, sections were washed 3 times in PBS and subsequently blocked again with 5% NGS for 20 mins at room temperature. A secondary rabbit IgG-Cy3 antibody was incubated with the sections at 37° C. for 2 hours followed by 3 washes with PBS. All sections were counterstained with DAPI for 30 seconds at a dilution of 1:5000 of a stock 1 mg/ml solution. Analysis of stained sections was performed with an Olympus FluoView™ FV1000 Confocal microscope.

Assessment of BBB Integrity by Perfusion of a Biotinylated Tracer Molecule

Following RNAi-mediated ablation of transcripts encoding claudin-5, a tracer molecule was used to determine the extent to which the TJ's of the BBB had been affected. The biotinylated reagent EZ-Link™ Sulfo-NHS-Biotin (Pierce) (1 ml/g body weight of 2 mg/ml EZ-Link™ Sulfo-NHS-Biotin, 443 Da) was perfused for 5 minutes through the left ventricle of mice 24, 48, 72 hours and 1 week post-hydrodynamic delivery of claudin-5 siRNA. Following perfusion with the tracer molecule, the whole brain was dissected and placed in 4% PFA pH 7.4 overnight at 4° C. and subsequently washed 4×15 mins with PBS. Following cryoprotection with sucrose, frozen sections were cut on a cryostat at −20° C. and incubated with streptavidin conjugated to the fluorescent probe FITC. This allowed for the assessment of leakage of the biotinylated reagent of molecular weight 443 Da from the microvessels of the brain. All sections were counterstained with 4',6-diamidine-2-phenylindole-dihydrochloride (DAPI; Sigma Aldrich, Ireland) for 30 seconds at a dilution of 1:5000 of a stock 1 mg/ml solution, and sections were visualized using an Olympus FluoView™ FV1000 Confocal microscope.

Assessment of BBB/BRB Permeability to Molecules of 562 Daltons and 4,400 Daltons In order to determine the permeability of brain and retinal microvessels to a molecule of 562 Daltons, mice were perfused through the left ventricle with 500 µl/g body weight of PBS containing 100 µg/ml Hoechst stain H33342 (Sigma Aldrich, Ireland) and 1 mg/ml FITC-Dextran-4 (FD-4) 24, 48, 72 hours and 1 week post-hydrodynamic delivery of claudin-5 siRNA. Following perfusion, the whole brain was dissected and placed in 4% PFA pH 7.4 overnight at 4° C. and subsequently washed 4×15 mins with PBS. Brains were then embedded in 4% agarose and 50 µm sections were cut using a Vibratome®. Whole eyes were removed and fixed with 4% PFA, and following washing with PBS and cryoprotection using a sucrose gradient, 12 µm cryosections were cut using a cryostat. Following analysis of retinal cryosections with an Olympus FluoView™ FV1000 Confocal microscope, images were oriented correctly using Adobe® Photoshop®.

Magnetic Resonance Imaging

Following injection of siRNA and using appropriate controls, BBB integrity was assessed in vivo via MRI, using a dedicated small rodent Bruker BioSpec 70/30 (i.e. 7 T, 30 cm bore) with an actively shielded USR Magnet. Mice were anaesthetised with isofluorane, and physiologically monitored (ECG, respiration and temperature) and placed on an MRI-compatible support cradle, which has a built-in system for maintaining the animal's body temperature at 37° C. The cradle was then positioned within the MRI scanner. Accurate positioning is ensured by acquiring an initial rapid pilot image, which is then used to ensure the correct geometry is scanned in all subsequent MRI experiments. Upon insertion into the MRI scanner, high resolution anatomical images of the brain were acquired (100 µm in-plane and 500 µm through-plane spatial resolution). BBB integrity was then visualised in high resolution $T_1$ weighted MR images before and after injection of a 0.1 mM/L/kg bolus of Gd-DTPA (Gadolinium diethylene-triamine pentaacetic acid), administered via the tail vein.

Electroretinographic Analysis of IMPDH−/− Mice and GTP Injection

IMPDH−/− mice that had received a hydrodynamic injection of siRNA targeting claudin-5 were dark-adapted overnight and prepared for electroretinography under dim red light. Pupillary dilation was carried out by installation of 1% cyclopentalate and 2.5% phenylephrine. Animals were anesthetized by intraperitoneal injection of ketamine (2.08 mg per 15 g body weight) and xylazine (0.21 mg per 15 g body weight). Once the animal was anaesthetized, GTP was injected intraperitoneally. The ERG commenced ten minutes after administration of anesthetic. Standardised flashes of light were presented to the mouse in a Ganzfeld bowl to ensure uniform retinal illumination. The ERG responses were recorded simultaneously from both eyes by means of gold wire electrodes (Roland Consulting Gmbh) using Vidisic (Dr Mann Pharma, Germany) as a conducting agent and to maintain corneal hydration. The eye was maintained in a proposed position throughout the examination by means of a small plastic band placed behind the globe. Reference and ground electrodes were positioned subcutaneously, approximately 1 mm from the temporal canthus and anterior to the tail respectively. Body temperature was maintained at 37° C. using a heating device controlled by a rectal temperature probe. Responses were analysed using a RetiScan RetiPort electrophysiology unit (Roland Consulting Gmbh). The protocol was based on that approved by the International Clinical Standards Committee for human electroretinography.

Immunohistochemical Analysis of Flatmounted Retinas

Whole eyes were fixed for 4 hours in 4% paraformaldehyde followed by 3 washes with phosphate buffered saline (PBS). Retinas were dissected out of the eyes and blocked/permeabilised by incubation with PBS containing 0.5% Triton X-100 and 5 normal goat serum (NGS). Retinas were subsequently incubated overnight in permeabilisation buffer containing 1% NGS and a 1:50 dilution of Rabbit anti-claudin-5 antibody (Zymed). Following 10 washes with PBS over a period of 2 hours, retinas were incubated for 6 hours at room temperature with a rabbit IgG antibody conjugated with the fluorescent probe Cy-3. Following 10 washes with PBS over a period of 2 hours, retinas were flatmounted and viewed using a confocal microscope.

Endothelial Cell Morphology of Major Organs

Following hydrodynamic injection of siRNA targeting claudin-5, cryosections were prepared of all the major organs, the heart, liver, lung and kidney. Sections were incubated overnight at 4° C. with HRP-conjugated *Griffonia simplicifolia*-isolectin B4 in order to stain the endothelial cells of organs.

Results

Hydrodynamic Tail Vein Injection of CLDN5 siRNA Attenuates Claudin-5 Expression

Following delivery of 20 µg claudin-5 siRNA, mice were left for 24, 48, 72 hours and 1 week, after which time brains were dissected and protein and RNA isolated as described previously. After 24 hours, levels of expression of Claudin-5 were markedly decreased when compared to Control (Un-injected), PBS injected and Non-targeting (Rhodopsin) controls. Mice injected with CLDN5 siRNA and subsequently left for 48 hours also showed significant decreases in Claudin-5 expression when compared to the controls employed. At 72 hours post-injection, this observed decrease in Claudin-5 expression was less evident, and levels of expression appeared similar to those observed in the control groups. One week post injection of claudin-5 siRNA, levels of expression of claudin-5 were similar to those in the control groups of animals. All blots are representative of at least 3 separate experiments (FIG. 1A).

Levels of claudin-5 mRNA were determined by RT-PCR analysis and showed a significant decrease 24 hours post-injection of siRNA targeting claudin-5. This highly significant decrease was not observed at the later time points, and showed claudin-5 mRNA levels suppressed up to 95% with respect to the non-targeting control siRNA (FIG. 1B). Levels of claudin-5 mRNA 48 hours, 72 hours and 1 week post injection were similar to those observed in the control groups (FIG. 1B).

Claudin-5 Expression and Localisation Becomes Altered in Brain Capillary Endothelial Cells Following Injection of Claudin-5 siRNA The level of expression of claudin-5 at the TJ in brain capillary endothelial cells changed dramatically following suppression of claudin-5 expression. As shown in FIG. 2, immunohistochemical analysis of claudin-5 expression and localisation in the microvessels of the brain which revealed a linear and distinct pattern of staining at the periphery of endothelial cells of the BBB in the un-injected, PBS injected and non-targeting control (Rhodopsin) mice at all time points after injection.

Claudin-5 expression was linear and intense at the periphery of endothelial cells lining the microvessels of the un-injected, PBS injected and non-targeting siRNA (Rhodopsin) injected control groups. However, 24 hours post injection of claudin-5 siRNA, this staining pattern appeared less intense, and by 48 hours post-injection there was a marked decrease in the presence of claudin-5 expression at the periphery of brain capillary endothelial cells throughout the brain when compared to un-injected, PBS-injected or non-targeting siRNA injected mice. At 72 hours post-injection, claudin-5 expression was still attenuated, yet a linear pattern of staining was evident in the cryosections (FIG. 2).

These results are representative of at least 5 separate experiments

Claudin-5 siRNA Causes Increased Permeability at the BBB

FIG. 5 shows the results of the assessment of the blood brain barrier integrity by perfusion of a biotinylated tracer molecule. EZ-Link™ Sulfo-NHS-Biotin was perfused through the left ventricle in mice following exposure to experimental conditions. Upon incubation of cryosections with streptavidin conjugated to the fluorescent probe FITC, the integrity of the BBB was observed as green fluorescence within the microvessels in the control groups (un-injected, PBS injected and a non-targeting siRNA. However, 24 hours post-injection of siRNA targeting claudin-5, it was observed that the fluorescence detected was diffuse and outside of the microvessels in contrast to the control groups at the same time point. At 48 hours post-injection of claudin-5 siRNA, the distribution of the biotinylated molecule was abundant in the brain parenchyma, while this permeability was still evident 72 hours post-delivery of siRNA when compared to the control groups at the same time points. In mice 1 week post-injection of siRNA targeting claudin-5, it was observed that the primary amine-reactive biotinylated reagent did not deposit in the parenchyma following perfusion for 5 minutes. The EZ-Link™ Sulfo-NHS-Biotin was observed to remain in the microvessels of the brain due to an intact BBB.

All tracer experiments were repeated in mice at least 5 times.

In summary, upon delivery of siRNA targeting claudin-5 to brain capillary endothelial cells, an increase in permeability to a small biotinylated molecule (443 Da) was observed after 24 hours. The passage of this molecule across the BBB became very distinct 48 hours post-injection, with large quantities of EZ-Link™ Sulfo-NHS-Biotin infiltrating the parenchymal tissue of the brain. The passage of this molecule across the BBB was still evident 72 hours post-injection of claudin-5 siRNA, however 1 week post-injection, there was no evidence for BBB compromise and the EZ-Link™ Sulfo-NHS-Biotin was shown to remain within the microvessels of the brain (FIG. 5).

FIG. 6 shows the results of the assessment of the blood brain barrier integrity by perfusion of a biotinylated tracer molecule at a high magnification. It was observed that upon perfusion of the primary amine reactive biotinylated reagent (443 Da) for 5 minutes 24 hours post-injection of siRNA targeting claudin-5 caused an infiltration of the molecule into the parenchyma of the brain when compared to the un-injected, PBS injected and non-targeting siRNA injected mice. This infiltration was detected in abundance 48 hours post-delivery of siRNA, and was still evidenced up to and including 72 hours following injection of claudin-5 siRNA. In mice 1 week post-injection of claudin-5 siRNA, it was observed that the EZ-Link™ Sulfo-NHS-biotin remained in the microvessels of the brain and failed to deposit in the parenchyma.

In summary, upon analysis of brain cryosections at a higher magnification in the dentate gyrus region of the hippocampus (for ease of recognition), it was apparent that 1 week post-injection of claudin-5 siRNA, the BBB did not allow for the passage of EZ-Link™ Sulfo-NHS-Biotin that was so clearly evidenced 48 hours post-injection of siRNA (FIG. 6).

Claudin-5 siRNA Causes Increased Permeability at the BBB and BRB to a Molecule of 562 Daltons Intriguingly, upon perfusion of the nuclear stain Hoechst H33342 (562 Daltons) and the FITC labelled dextran, FD-4 (4,400 Daltons), extravasation of Hoechsct was observed up to and including 48 hours post-delivery of siRNA targeting claudin-5, however, unlike EZ-Link™ Sulfo-NHS-Biotin, this extravasation was not evident 72 hours post siRNA delivery, suggesting a restoration of barrier integrity to a molecule of 562 Daltons, and implying a time dependent and size-selective opening of the BBB. Hoechst H33342 dye extravasation from the brain microvessels was manifested by nuclear staining of surrounding neural and glial cells in the parenchyma. FD-4 remained within the microvessels of the brain vasculature and no extravasation was evident at any time point post-injection of siRNA (FIG. 6B). Moreover, upon analysis of retinal cryosections, we observed that Hoechst H33342 extravasated from the retinal microvessels, staining the Inner Nuclear Layer (INL) and Outer Nuclear Layer (ONL) of the retina up to 48 hour post-delivery of siRNA targeting claudin-5 (FIG. 6A).

MRI Analysis Showed Impairment of BBB Integrity 48 Hours Post-Injection of Claudin-5 siRNA FIG. 7A shows the results of an MRI Scan post injection to assess the blood brain barrier integrity in vivo. The magnetic resonance imaging (MRI) contrasting agent Gd-DTPA was used to ascertain BBB integrity in mice following ablation of claudin-5 transcripts. At 48 hours post-injection of claudin-5 siRNA, it was observed that Gd-DTPA crossed the BBB and was deposited in the parenchymal tissue of the brain. The image to the left of the figure is the contrasting of the mouse brain before injection of Gd-DTPA, while the image to the right is the contrasting of the mouse brain following injection of Gd-DTPA. The images are taken coronally moving from the ventral aspect of the brain to the dorsal aspect, and reveal significant deposition of Gd-DTPA (742 Da) in the parenchyma 48 hours post-injection of siRNA targeting claudin-5.

This infiltration of the contrasting agent was not present in the un-injected, PBS injected or non-targeting siRNA injected mice, nor was it present in mice 72 hours or 1 week post-injection of siRNA targeting claudin-5.

In summary, infiltration of Gd-DTPA into the brain parenchymal tissue was observed as widespread and intense contrasting throughout the brain when compared to un-injected, PBS injected and non-targeting siRNA injected mice, indicating that the BBB was compromised enough to allow for the passage of a molecule of 742 Da in size. MRI scans on mice 72 hours and 1 week post-injection of claudin-5 siRNA revealed an intact barrier with no deposition of Gd-DTPA in the parenchymal tissue, highlighting this BBB disruption as a transient event (FIG. 7A).

Conclusion

As shown in Example 1, the hydrodynamic approach for delivery of siRNA's to endothelial cells of the brain microvasculature is highly efficient in suppressing claudin-5 expression (FIGS. 1A and 1B). This method of delivery caused little harm and was well tolerated in mice. The Western data showed that maximum suppression of claudin-5 was achieved 48 hours after delivery of the siRNA, with levels of expression of claudin-5 returning to normal between 72 hours and 1 week after injection. Thus, the reversible RNAi-mediated opening of the BBB using siRNA targeting claudin-5 is now possible.

It was then determined whether similar to the claudin-5 knockout mouse, the BBB became compromised to small molecules when claudin-5 expression was suppressed. At the periphery of endothelial cells in the brain microvasculature, levels of claudin-5 appeared strong and "linear-like" upon immunohistochemical analysis of all the control groups employed. However, when claudin-5 was targeted, this linear appearance of expression became discontinuous and fragmented, with levels appearing dramatically reduced 48 hours after injection of claudin-5 siRNA (FIG. 2). Moreover, upon perfusion of mice with the biotinylated molecule EZ-Link™ Sulfo-NHS-Biotin for 5 minutes, a significant compromise in barrier function was observed up to and including 72 hours post delivery of siRNA targeting claudin-5. EZ-Link™ Sulfo-NHS-Biotin has a molecular weight of 443 Da, and will normally not cross the BBB if the TJ's are intact as observed in the control groups. Interestingly, 1 week after delivery of claudin-5 siRNA, this molecule no longer crossed the BBB, suggesting that consistent with Real-Time PCR and Western analyses, this compromise in BBB function is a transient and reversible process.

During this study, no distinct or noticeable behavioural changes in these mice, while the gross histology of both vibratome and cryosections of the brain appeared normal under all experimental conditions.

Similar to claudin-5 knockout mouse, the MRI contrasting agent Gd-DTPA was also found to cross the BBB and deposit in the parenchymal tissue of the brain post siRNA injection. In fact extremely large quantities of Gd-DTPA were deposited in the brain 48 hours post delivery of claudin-5 siRNA. This BBB breakage to a molecule of 742 Da was a transient event, as 72 hours and 1 week post injection of siRNA targeting claudin-5, there appeared to be no deposition of Gd-DTPA. The significance of these results was that as well as being a transient event, suppression of claudin-5 appeared to be causing a size-selective change in the permeability of the barrier, as evidenced from the observation that while a molecule of 443 Da crossed the BBB 72 hours post delivery of siRNA, a molecule of 742 Da failed to do so at the same time point (FIG. 7A), and a molecule of 562 Da crossed the BBB at 24 and 48 hours post delivery of siRNA while a molecule of 4,400 Da failed to do so (FIGS. 6A and 6B).

As siRNA was administered via the tail vein, and given the fact that claudin-5 is expressed in microvascular endothelial cells of the lung and the heart, we wished to assess whether siRNA targeting claudin-5 would adversely affect endothelial cell morphology in the liver, lung, kidney or heart. Cryosections of each of these organs were prepared at all time points following injection of siRNA targeting claudin-5 and incorporating the appropriate controls. Sections were stained with HRP-conjugated *Griffonia simplicifolia*-isolectin B4, which binds to intact endothelial cells, and showed that endothelial cell morphology appeared similar at all time points and in all major organs following siRNA injection when compared to the control groups (FIGS. 9-12). The role of claudin-5 in organs other than the brain and eye has not been well characterised, and it is important to note that it does not appear to be fundamental in maintaining the size-selective properties of the tight junctions associated with these other organs.

In conclusion, it is now possible to systemically deliver siRNA molecules to the endothelial cells of the BBB and BRB. Targeted suppression of the TJ protein claudin-5 causes both a transient and size-selective increase in paracellular permeability of the barrier, which may allow for the delivery of molecules which would otherwise be excluded from the brain.

Example 2

Delivery of Thyrotropin Releasing Hormone (TRH) Across the Blood Brain Barrier (BBB) to Claudin-5 Suppressed Mice

Materials & Method
Thyrotropin Releasing Hormone (TRH) (Sigma Aldrich, Ireland)

TRH has been proposed as having distinct neuroprotective effects. It also induces "wet dog shake" behavioural outputs when administered to rats. However, TRH has several disadvantages, including its instability and resulting short duration of action and its slow permeation across the BBB.

Delivery of TRH to Claudin-5 Suppressed Mice
The protocol of Example 1 was followed to produce transiently claudin-5 suppressed mice.

48 hours post-delivery of siRNA targeting claudin-5 or a non-targeting siRNA, a 200 µl of a solution containing 20 mg/kg Thyrotropin Releasing Hormone (TRH) was injected to the claudin-5 suppressed mice. TRH was injected in the tail vein and immediately, the behavioural output of mice was assessed by filming them in a clear Perspex box.

Results and Conclusion
As shown in FIG. 8, following ablation of claudin-5 protein, a distinct increase in the length of time C57/Bl6 mice remain immobile upon administration of 20 mg/kg TRH was observed.

This behavioural output was significantly different from the behaviour observed in the non-targeting control mice, and clearly suggested that delivery of TRH was significantly enhanced when the BBB was compromised.

These results show that the protocol of Example 1 can be used to open the BBB to allow delivery of compositions to the BBB which previously would not have been possible. These results clearly suggest that delivery of TRH (359.5 Da) was significantly enhanced when the BBB was reversibly, transiently opened in a controlled size selective manner.

Example 3

In Vivo Suppression of Claudin-1 Expression at the Blood Brain Barrier of C57/Bl-6 Mice Using Systemic Hydrodynamic Tail Vein Delivery of siRNA Targeting Claudin-1

Materials:
Web-Based siRNA Design Protocols Targeting Claudin-1

|  |  |
|---|---|
| CLDN1 (1) target sequence: | (SEQ ID NO: 32)<br>GCAAAGCACCGGGCAGAUA: |
| Sense sequence: | (SEQ ID NO: 9)<br>AUAGACGGGCCACGAAACGUU |
| Anti-sense strand: | (SEQ ID NO: 10)<br>CGUUUCGUGGCCCGUCUAUUU |
| CLDN1 (2) target sequence: | (SEQ ID NO: 33)<br>GAACAGUACUUUGCAGGCA: |
| Sense strand: | (SEQ ID NO: 11)<br>ACGGACGUUUCAUGACAAGUU |
| Anti-sense strand: | (SEQ ID NO: 12)<br>CUUGUCAUGAAACGUCCGUUU |
| CLDN1 (4) target sequence: | (SEQ ID NO. 34)<br>UUUCAGGUCUGGCGACAUU: |
| Sense sequence: | (SEQ ID NO: 13)<br>UUACAGCGGUCUGGACUUUUU |
| Anti-sense strand: | (SEQ ID NO: 14)<br>AAAGUCCAGACCGCUGUAAUU |

Methods:
The protocols used were identical to the protocols used in Example 1.

Results and Conclusions:
Results are shown in FIGS. 3A, 23 and 24.

This example shows that siRNA directed against claudin-1 causes an increase in paracellular permeability at the BBB to a molecule of 562 Daltons but not 4,400 Daltons. Suppression of claudin-1 appears to cause a size-selective opening of the BBB in a manner similar to that observed when claudin-5 was suppressed.

Example 4

In Vivo Suppression of Occludin Expression at the Blood Brain Barrier of C57/Bl-6 Mice Using Systemic Hydrodynamic Tail Vein Delivery of siRNA Targeting Occludin

Materials:
Web-Based siRNA Design Protocols Targeting Occludin

|  |  |
|---|---|
| Occl (1) target sequence: | (SEQ ID NO: 35)<br>GUUAUAAGAUCUGGAAUGU: |
| Sense sequence: | (SEQ ID NO: 15)<br>UGUAAGGUCUAGAAUAUUGUU |
| Anti-sense sequence: | (SEQ ID NO: 16)<br>CAAUAUUCUAGACCUUACAUU |
| Occl (2) target sequence: | (SEQ ID NO: 36)<br>GAUAUUACUUGAUCGUGAU: |
| Sense sequence: | (SEQ ID NO: 17)<br>UAGUGCUAGUUCAUUAUAGUU |
| Anti-sense sequence: | (SEQ ID NO: 18)<br>CUAUAAUGAACUAGCACUAUU |
| Occl (3) target sequence: | (SEQ ID NO: 37)<br>CAAAUUAUCGCACAUCAAG: |
| Sense sequence: | (SEQ ID NO: 19)<br>GAACUACACGCUAUUAAACUU |
| Anti-sense sequence: | (SEQ ID NO: 20)<br>GUUUAAUAGCGUGUAGUUCUU |
| Occl (4) target sequence: | (SEQ ID NO: 38)<br>AGAUGGAUCGGUAUGAUAA: |
| Sense sequence: | (SEQ ID NO: 21)<br>AAUAGUAUGGCUAGGUAGAUU |
| Anti-sense sequence: | (SEQ ID NO: 22)<br>UCUACCUAGCCAUACUAUUUU |

Methods:

The protocols used were identical to the protocols used in Example 1.

Results and Conclusions:

Results are shown in FIGS. 3B, 19, 20, 21 and 22

This example shows that siRNA directed against Occludin causes an increase in paracellular permeability at the BBB to molecules greater than 70,000 Daltons, as this is the approximate weight of albumin. Suppression of occludin at the BBB does produce a larger size-exclusion limit however. It was observed that while albumin deposition occurred 24 hours post-injection of occludin siRNAs 3 & 4, there was no extravasation of immunoglobulins (IgGs) in the blood. IgG's have an approximate molecular weight of 120,000 daltons.

Example 5

In Vivo Suppression of Claudin 12 Expression at the Blood Brain Barrier of C57/Bl-6 Mice Using Systemic Hydrodynamic Tail Vein Delivery of siRNA Targeting Claudin 12

Materials:
Web-Based siRNA Design Protocols Targeting Claudin-12

```
CLDN12 SIRNA (3) Target sequence:
GUAACACGGCCUUCAAUUC             (SEQ ID NO: 41)

5'-GUAACACGGCCUUCAAUUCUU-        (SEQ ID No. 28)
3'

5'-GAAUUGAAGGCCGUGUUACUU-        (SEQ ID No. 29)
3'

CLDN12 SIRNA (4) Target sequence:
GGUCUUUACCUUUGACUAU      (SEQ ID NO: 42)

5'-AAUCUUUACCUUUGACUAUUU-        (SEQ ID No. 30)
3'

5'-AUAGUCAAAGGUAAAGAUUUU-        (SEQ ID No. 31)
3'
```

Methods:

The protocols used were identical to the protocols used in Example 1.

Results and Conclusions:

Claudin-12 levels were shown to decrease following hydrodynamic tail vein injection of siRNA targeting claudin-12 (FIG. 12). The pattern of claudin-12 staining was observed to be associated with the brain microvasculature 48 hours post-injection of a non-targeting control siRNA. However, 48 hours post-injection of siRNA targeting claudin-12, levels of expression at the microvessels of the brain were shown to be decreased in both siRNAs tested (i.e., CLDN12 siRNA (3) and CLDN12 siRNA (4)).

Following hydrodynamic tail vein injection of a non-targeting siRNA or siRNA targeting claudin-12, mice were perfused through the left ventricle with a solution containing FITC-dextran-4 and Hoechst 33342 (562 Da). It was observed that following injection of siRNA targeting claudin-12, there was extravasation of Hoechst from the microvasculature as evidenced by staining of the extravascular nuclei. FD-4 was observed in the microvessels and in both the non-targeting siRNA and following injection of siRNA targeting claudin-12 (FIG. 31).

Example 6

Gd-DTPA 48 Hours Post-Delivery of siRNA Targeting Claudin-5

Materials & Methods:

The protocol of Example 1 was followed to produce transiently claudin-5 suppressed mice.

48 hours post-delivery of siRNA targeting claudin-5 or a non-targeting siRNA, a solution containing Gd-DTPA injected to the claudin-5 suppressed mice. Gd-DTPA was injected in the tail vein to assess whether Gd-TPA would permeate across the BBB. Following injection of siRNA and using appropriate controls, BBB integrity to a molecule of 742 Daltons (Gd-DTPA) was assessed via MRI, using a dedicated small rodent Bruker BioSpec 70/30 (i.e. 7 T, 30 cm bore) with an actively shielded USR Magnet. Mice were anaesthetised with isofluorane, and physiologically monitored (ECG, respiration and temperature) and placed on an MRI-compatible support cradle, which has a built-in system for maintaining the animal's body temperature at 37° C. The cradle was then positioned within the MRI scanner. Accurate positioning is ensured by acquiring an initial rapid pilot image, which is then used to ensure the correct geometry is scanned in all subsequent MRI experiments. Upon insertion into the MRI scanner, high resolution anatomical images of the brain were acquired (100 μm in-plane and 500 μm through-plane spatial resolution). BBB integrity was then visualised in high resolution $T_1$ weighted MR images before and after injection of a 0.1 mM/L/kg bolus of Gd-DTPA (Gadolinium diethylene-triamine pentaacetic acid), administered via the tail vein. Following injection of Gd-DTPA, repeated 3 minute $T_1$-weighted scans were performed over a period of 30 minutes, and images shown are representative of the final scans of this 30 minute period. Statistical analysis of all densitometric results of combined regions of the Cerebellum, Hippocampus and Cortex was performed using ANOVA, with significance represented by a P value of ≤0.05, and results are presented both graphically and in a quantitative image depicting the rate of Gd-DTPA deposition within the brain. All MRI scans were performed on 2 mice from each experimental treatment.

Results:

FIG. 26 shows T1-weighted MRI images of the Hippocampal region of the mouse brain 48 hours post-delivery of siRNA targeting claudin-5 clearly shows enhanced contrasting within the brain as Gd-DTPA extravasates from brain microvessels. Gd-DTPA has a molecular weight of 742 Daltons, and its permeation into the brain was only observed at 24 and 48 hours post delivery of siRNA.

FIG. 27 shows MRI information related to blood flow/volume changes within the brains of mice 24 and 48 hours post-high volume tail vein injection of siRNA targeting claudin-5. This data gives information on two things, the mean transit time (MTT) and capillary transit time (CTT). The MTT represents the time taken for the labelled spins to travel from the labelling plane (carotid artery ~1 cm from imaging slice) to the imaging slice.

This is calculated from the first moment or mean of the curve. From the second moment of the curve (variance) we get the CTT, which is the time taken for the labelled spins to be distributed over the imaging slice by exchange from capillary bed to tissue. With up to 8 animals per group, we are seeing no significant differences in blood flow within the major vessels in the brain or the capillaries, which is quite promising given the high volume of injection required to deliver claudin-5 siRNA to brain microvascular endothelial cells.

FIG. 28 shows the theoretical model for cerebral blood flow and cerebral blood volume fitted to the experimental data for each experimental group tested group. These are almost exactly the same for each group which agrees with the findings of the histograms presented in FIG. 27.

Conclusion:

In conclusion, these results show that we are not observing any difference in blood flow or blood volume in the large vessels in the brain or in the microvasculature and suggests that in cases of cerebral oedema, claudin-5 siRNA may in fact allow for an increased rate water diffusion at the site of injury in the brain.

Example 7

Water Diffusion in the Brains of Mice 24 and 48 Hours after Receiving Non-Targeting or Claudin-5 siRNA Materials & Methods:

The protocol of Example 1 was followed to produce transiently claudin-5 suppressed mice.

24 and 48 hours post-delivery of siRNA targeting claudin-5 or a non-targeting siRNA mice were anaesthetised with isofluorane, and physiologically monitored (ECG, respiration and temperature) and placed on an MRI-compatible support cradle, which has a built-in system for maintaining the animal's body temperature at 37° C. The cradle was then positioned within the MRI scanner. Accurate positioning is ensured by acquiring an initial rapid pilot image, which is then used to ensure the correct geometry is scanned in all subsequent MRI experiments. Upon insertion into the MRI scanner, high resolution anatomical images of the brain were acquired (100 µm in-plane and 500 µm through-plane spatial resolution). Water diffusion scans were subsequently undertaken. Using a standard diffusion imaging sequence such as a spin-echo EPI imaging sequence with diffusion gradients (Stejskal-Taner gradients) in order to acquire images over a large range of b-values. In this way, the effect of the technique in the vascular compartment and in the brain parenchymal tissue can be compared. All experiments were carried out on a 7 T Brüker small-bore system with 400 mT/m maximum gradient strength. Image processing and calculation of ADCs was carried out using IDL.

Results:

FIG. 29 shows the B-values (x-axis) plotted above with MRI signal intensity (y-axis) show no change in the rate of water diffusion in the brains of mice at 24 and 48 hours post injection of a non-targeting siRNA or siRNA targeting claudin-5. This constant rate of water diffusion from the brain to the blood suggests that the transient BBB opening in itself does not have any profound impact on water diffusion in the brains of mice.

In conclusion, the results shown in FIG. 30 show the rates of water diffusion in the brains of mice 24 and 48 hours after receiving non-targeting or claudin-5 siRNA. Essentially, there are no changes in diffusion in any mice under these experimental conditions. This is another important observation and as Example 6 also suggests that in cases of cerebral oedema, claudin-5 siRNA may in fact allow for an increased rate of water diffusion at the site of injury in the brain.

The invention claimed is:

1. A method for the treatment of a traumatic brain injury or stroke wherein the treatment comprises the systemic or viral mediated delivery of a RNAi inducing agent targeting claudin-5 to allow the permeation and free diffusion of water across the blood brain barrier, and results in the reversible and transient RNAi-mediated suppression of claudin-5 in brain capillary endothelial cells and wherein RNAi-mediated suppression commences from approximately 24 hours post delivery of the RNAi inducing agent and lasts up to approximately 72 hours post delivery of the RNAi inducing agent.

2. The method according to claim 1 further comprising the sequential or simultaneous application of an active agent.

3. A method for reducing intercranial pressure and/or reduction of cerebral oedema in a patient, wherein the method comprises:
   systemic or viral mediated delivery to the patient of an RNAi-inducing agent that targets claudin-5 to allow the permeation and free diffusion of water across the blood brain barrier,
   thereby resulting in reversible and transient RNAi-mediated suppression of claudin-5 in brain capillary endothelial cells and wherein RNAi-mediated suppression commences from approximately 24 hours post delivery of the RNAi inducing agent and lasts up to approximately 72 hours post delivery of the RNAi inducing agent.

4. The method according to claim 1, wherein the RNAi inducing agent is chosen from one of the following: sRNA, shRNA or an RNAi-inducing vector whose presence within a cell results in production of an sRNA or shRNA.

5. The method according to claim 3, wherein the RNAi inducing agent is chosen from one of the following: sRNA, shRNA or an RNAi-inducing vector whose presence within a cell results in production of an sRNA or shRNA.

6. The method according to claim 2 in which the active agent is a hypertonic solution which provides an osmotic gradient to facilitate water diffusion.

7. The method according claim 2 in which the active agent is a hypertonic solution selected from mannitol and hypertonic saline solution, or a hypertonic sugar solution.

8. The method according to claim 3 further comprising the sequential or simultaneous application of an active agent.

9. The method according to claim 8 in which the active agent is a hypertonic solution which provides an osmotic gradient to facilitate water diffusion.

10. The method according claim 8 in which the active agent is a hypertonic solution selected from mannitol and hypertonic saline solution, or a hypertonic sugar solution.

* * * * *

SEQUENCE LISTING

```
<160> NUMBER OF SEQ ID NOS: 49

<210> SEQ ID NO 1
<211> LENGTH: 21
<212> TYPE: RNA
<213> ORGANISM: Artificial
<220> FEATURE:
<223> OTHER INFORMATION: Claudin-5 siRNA sense strand

<400> SEQUENCE: 1
cguuggaaau ucugggucuu u                                           21

<210> SEQ ID NO 2
<211> LENGTH: 21
<212> TYPE: RNA
<213> ORGANISM: artificial
<220> FEATURE:
<223> OTHER INFORMATION: Claudin-5 siRNA antisense strand

<400> SEQUENCE: 2
agacccagaa uuuccaacgu u                                           21

<210> SEQ ID NO 3
<211> LENGTH: 21
<212> TYPE: RNA
<213> ORGANISM: artificial
<220> FEATURE:
<223> OTHER INFORMATION: Claudin-5 siRNA sense strand

<400> SEQUENCE: 3
caauggcgau uacgacaagu u                                           21
```

<210> SEQ ID NO 4
<211> LENGTH: 21
<212> TYPE: RNA
<213> ORGANISM: artificial
<220> FEATURE:
<223> OTHER INFORMATION: Claudin-5 siRNA antisense strand

<400> SEQUENCE: 4 cugucguaa ucgccauugu u                                                    21

<210> SEQ ID NO 5
<211> LENGTH: 21
<212> TYPE: RNA
<213> ORGANISM: artificial
<220> FEATURE:
<223> OTHER INFORMATION: Claudin-5 siRNA sense strand

<400> SEQUENCE: 5
ucacgggagg agcgcuuuau u                                                   21

<210> SEQ ID NO 6
<211> LENGTH: 21
<212> TYPE: RNA
<213> ORGANISM: artificial
<220> FEATURE:
<223> OTHER INFORMATION: Claudin-5 siRNA antisense strand

<400> SEQUENCE: 6
uaaagcgcuc cucccgugau u                                                   21

<210> SEQ ID NO 7
<211> LENGTH: 21
<212> TYPE: RNA
<213> ORGANISM: artificial
<220> FEATURE:
<223> OTHER INFORMATION: Claudin-5 siRNA sense strand

<400> SEQUENCE: 7
gcgcagacga cuuggaaggu u                                                   21

<210> SEQ ID NO 8
<211> LENGTH: 21
<212> TYPE: RNA
<213> ORGANISM: artificial
<220> FEATURE:
<223> OTHER INFORMATION: Claudin-5 siRNA antisense strand

<400> SEQUENCE: 8
ccuuccaagu cgucugcgcu u                                                   21

<210> SEQ ID NO 9
<211> LENGTH: 21
<212> TYPE: RNA
<213> ORGANISM: artificial
<220> FEATURE:
<223> OTHER INFORMATION: Claudin-1 siRNA sense strand

<400> SEQUENCE: 9
auagacgggc cacgaaacgu u                                                   21

<210> SEQ ID NO 10
<211> LENGTH: 20
<212> TYPE: RNA
<213> ORGANISM: artificial
<220> FEATURE:
<223> OTHER INFORMATION: Claudin-1 siRNA antisense strand

```
<400> SEQUENCE: 10
cguuucgugg cccgucuauu                                          20

<210> SEQ ID NO 11
<211> LENGTH: 21
<212> TYPE: RNA
<213> ORGANISM: artificial
<220> FEATURE:
<223> OTHER INFORMATION: Claudin-1 siRNA sense strand

<400> SEQUENCE: 11
acggacguuu caugacaagu u                                        21

<210> SEQ ID NO 12
<211> LENGTH: 21
<212> TYPE: RNA
<213> ORGANISM: artificial
<220> FEATURE:
<223> OTHER INFORMATION: Claudin-1 siRNA antisense strand

<400> SEQUENCE: 12 cuugcauga aacguccguu u                                         21

<210> SEQ ID NO 13
<211> LENGTH: 21
<212> TYPE: RNA
<213> ORGANISM: artificial
<220> FEATURE:
<223> OTHER INFORMATION: Claudin-1 siRNA sense strand

<400> SEQUENCE: 13
uuacagcggu cuggacuuuu u                                        21

<210> SEQ ID NO 14
<211> LENGTH: 21
<212> TYPE: RNA
<213> ORGANISM: artificial
<220> FEATURE:
<223> OTHER INFORMATION: Claudin-1 siRNA antisense strand

<400> SEQUENCE: 14
aaaguccaga ccgcuguaau u                                        21

<210> SEQ ID NO 15
<211> LENGTH: 21
<212> TYPE: RNA
<213> ORGANISM: artificial
<220> FEATURE:
<223> OTHER INFORMATION: Occludin siRNA sense strand

<400> SEQUENCE: 15
uguaaggucu agaauauugu u                                        21

<210> SEQ ID NO 16
<211> LENGTH: 21
<212> TYPE: RNA
<213> ORGANISM: artificial
<220> FEATURE:
<223> OTHER INFORMATION: Occludin siRNA antisense strand

<400> SEQUENCE: 16
caauauucua gaccuuacau u                                        21

<210> SEQ ID NO 17
```

```
<211> LENGTH: 21
<212> TYPE: RNA
<213> ORGANISM: artificial
<220> FEATURE:
<223> OTHER INFORMATION: Occludin siRNA sense strand

<400> SEQUENCE: 17
uagugcuagu ucauuauagu u                                              21

<210> SEQ ID NO 18
<211> LENGTH: 21
<212> TYPE: RNA
<213> ORGANISM: artificial
<220> FEATURE:
<223> OTHER INFORMATION: Occludin siRNA antisense strand

<400> SEQUENCE: 18
cuauaaugaa cuagcacuau u                                              21

<210> SEQ ID NO 19
<211> LENGTH: 21
<212> TYPE: RNA
<213> ORGANISM: artificial
<220> FEATURE:
<223> OTHER INFORMATION: Occludin siRNA sense strand

<400> SEQUENCE: 19
gaacuacacg cuauuaaacu u                                              21

<210> SEQ ID NO 20
<211> LENGTH: 21
<212> TYPE: RNA
<213> ORGANISM: artificial
<220> FEATURE:
<223> OTHER INFORMATION: Occludin siRNA antisense strand

<400> SEQUENCE: 20
guuuaauagc guguaguucu u                                              21

<210> SEQ ID NO 21
<211> LENGTH: 21
<212> TYPE: RNA
<213> ORGANISM: artificial
<220> FEATURE:
<223> OTHER INFORMATION: Occludin siRNA sense strand

<400> SEQUENCE: 21
aauaguaugg cuagguagau u                                              21

<210> SEQ ID NO 22
<211> LENGTH: 21
<212> TYPE: RNA
<213> ORGANISM: artificial
<220> FEATURE:
<223> OTHER INFORMATION: Occludin siRNA antisense strand

<400> SEQUENCE: 22
ucuaccuagc cauacuauuu u                                              21

<210> SEQ ID NO 23
<211> LENGTH: 1413
<212> TYPE: DNA
<213> ORGANISM: Mus musculus
<220> FEATURE:
<221> NAME/KEY: mRNA
<222> LOCATION: (1)..(1413)
<223> OTHER INFORMATION: Claudin-5 mRNA
```

<400> SEQUENCE: 23

```
agttggtgta gttaaaacct cctcttctgc tccaggactg gaggctccag agcagaggca    60
ccagaaccaa ttcccagctc ccagcctaag cagcgcagag agcacccgga ggccccaagg   120
gccgtcgggt gagcattcag tctttagcca tggggtctgc agcgttggaa attctgggtc   180
tggtgctgtg tctggtagga tgggtgggct tgatcctggc gtgtgggctg cccatgtggc   240
aggtgactgc cttcctggac cacaacatcg tgacggcgca gacgacttgg aaggggctgt   300
ggatgtcgtg cgtggtgcag agtaccgggc acatgcagtg caaggtgtat gaatctgtgc   360
tggcgctgag tgcggaggtg caggcagctc gggcactcac cgtgggcgct gtgctgctgg   420
cgctggtggc actctttgtt accttgaccg gcgctcagtg caccacctgc gtggccccgg   480
gcccagttaa ggcacgggta gcactcacgg gaggagcgct ttacgcggtg tgcgggctgc   540
tggcactcgt gccgctctgc tggttcgcca acatcgttgt ccgcgagttc tatgatccga   600
cggtgccggt gtcacagaag tacgagctgg gcgcggcgct gtacatcggc tgggcggcct   660
ccgcactgct catgtgcggt ggcggcctcg tgtgttgcgg cgcctgggtc tcaccgggcg   720
ccctgagttc agcttcccgg tcaagtactc agcgccgcgg cggcccacgg ccaatggcga   780
ttacgacaag aagaactatg tctaagggcg ggaggcatgg cggggctctt cccgcagcta   840
agcccgcgat gggaaagacc gatgcgggaa gccgtgtgtg gatgacgacc accgctgggt   900
tgcgcagcgc aagtcatgct gggttcgggc cagacttgcc cgctctcaga gtccgttgac   960
catcactagc cggccctgc tcagaacaga ctacaggcac ttttaagaac ttgaccgacc   1020
ttttcttcta tgcgcagttg gccacgacgt gggtggaacg ctcagatttc atcggtgaag  1080
taggcaccaa actgccgcga acagttccta ctgagatcct gggggcacta atgctgcct   1140
taatgtccag tggcacctgc taacctgaaa gggcagctgg agaaacccg gggctgccag   1200
agggacgtgt taaaagggc attttctttg ttagtggaga agaacctact gaaccaaagg   1260
acttagcctg gacctggtct cactccagca ctcccccaag gtgggggccc tgtaggtacc   1320
agagccttag aggggttgcc ttcctcctgg aagcttgggg cttgggggt gggccgggca   1380
agaatttgct cagtaaatgg tttgaacact ttc                                1413
```

<210> SEQ ID NO 24
<211> LENGTH: 21
<212> TYPE: RNA
<213> ORGANISM: artificial
<220> FEATURE:
<223> OTHER INFORMATION: Claudin-12 siRNA sense strand

<400> SEQUENCE: 24

```
gaaaucgaca uuccaguagu u                                              21
```

<210> SEQ ID NO 25
<211> LENGTH: 21
<212> TYPE: RNA
<213> ORGANISM: artificial
<220> FEATURE:
<223> OTHER INFORMATION: Claudin-12 siRNA antisense strand

<400> SEQUENCE: 25

```
cuacuggaau gucgauuucu u                                              21
```

<210> SEQ ID NO 26
<211> LENGTH: 21
<212> TYPE: RNA

```
<213> ORGANISM: artificial
<220> FEATURE:
<223> OTHER INFORMATION: Claudin-12 siRNA sense strand

<400> SEQUENCE: 26
cgugguaccu gucgguugau u                                              21

<210> SEQ ID NO 27
<211> LENGTH: 21
<212> TYPE: RNA
<213> ORGANISM: artificial
<220> FEATURE:
<223> OTHER INFORMATION: Claudin-12 antisense strand

<400> SEQUENCE: 27
ucaaccgaca gguaccacgu u                                              21

<210> SEQ ID NO 28
<211> LENGTH: 21
<212> TYPE: RNA
<213> ORGANISM: artificial
<220> FEATURE:
<223> OTHER INFORMATION: Claudin-12 siRNA sense strand

<400> SEQUENCE: 28
guaacacggc cuucaauucu u                                              21

<210> SEQ ID NO 29
<211> LENGTH: 21
<212> TYPE: RNA
<213> ORGANISM: artificial
<220> FEATURE:
<223> OTHER INFORMATION: Claudin-12 antisense strand

<400> SEQUENCE: 29
gaauugaagg ccguguuacu u                                              21

<210> SEQ ID NO 30
<211> LENGTH: 21
<212> TYPE: RNA
<213> ORGANISM: artificial
<220> FEATURE:
<223> OTHER INFORMATION: Claudin-12 siRNA sense strand

<400> SEQUENCE: 30
aaucuuuacc uuugacuauu u                                              21

<210> SEQ ID NO 31
<211> LENGTH: 21
<212> TYPE: RNA
<213> ORGANISM: artificial
<220> FEATURE:
<223> OTHER INFORMATION: Claudin-12 siRNA antisense strand

<400> SEQUENCE: 31
auagucaaag guaaagauuu u                                              21

<210> SEQ ID NO 32
<211> LENGTH: 19
<212> TYPE: RNA
<213> ORGANISM: Mus musculus

<400> SEQUENCE: 32
gcaaagcacc gggcagaua                                                 19
```

```
<210> SEQ ID NO 33
<211> LENGTH: 19
<212> TYPE: RNA
<213> ORGANISM: mus musculus

<400> SEQUENCE: 33
gaacaguacu uugcaggca                                                  19

<210> SEQ ID NO 34
<211> LENGTH: 19
<212> TYPE: RNA
<213> ORGANISM: mus musculus

<400> SEQUENCE: 34
uuucaggucu ggcgacauu                                                  19

<210> SEQ ID NO 35
<211> LENGTH: 19
<212> TYPE: RNA
<213> ORGANISM: mus musculus

<400> SEQUENCE: 35
guuauaagau cuggaaugu                                                  19

<210> SEQ ID NO 36
<211> LENGTH: 19
<212> TYPE: RNA
<213> ORGANISM: mus musculus

<400> SEQUENCE: 36
gauauuacuu gaucgugau                                                  19

<210> SEQ ID NO 37
<211> LENGTH: 19
<212> TYPE: RNA
<213> ORGANISM: mus musculus

<400> SEQUENCE: 37
caaauuaucg cacaucaag                                                  19

<210> SEQ ID NO 38
<211> LENGTH: 19
<212> TYPE: RNA
<213> ORGANISM: mus musculus

<400> SEQUENCE: 38
agauggaucg guaugauaa                                                  19

<210> SEQ ID NO 39
<211> LENGTH: 19
<212> TYPE: RNA
<213> ORGANISM: mus musculus

<400> SEQUENCE: 39
gaaaucgaca uuccaguag                                                  19

<210> SEQ ID NO 40
<211> LENGTH: 19
<212> TYPE: RNA
<213> ORGANISM: mus musculus

<400> SEQUENCE: 40
cgugguaccu gucgguuga                                                  19
```

```
<210> SEQ ID NO 41
<211> LENGTH: 19
<212> TYPE: RNA
<213> ORGANISM: mus musculus

<400> SEQUENCE: 41
guaacacggc cuucaauuc                                               19

<210> SEQ ID NO 42
<211> LENGTH: 19
<212> TYPE: RNA
<213> ORGANISM: mus musculus

<400> SEQUENCE: 42
ggucuuuacc uuugacuau                                               19

<210> SEQ ID NO 43
<211> LENGTH: 21
<212> TYPE: DNA
<213> ORGANISM: mus musculus

<400> SEQUENCE: 43
aacgttggaa attctgggtc t                                            21

<210> SEQ ID NO 44
<211> LENGTH: 19
<212> TYPE: RNA
<213> ORGANISM: homo sapiens

<400> SEQUENCE: 44
cgcucaagcc ggaggucaa                                               19

<210> SEQ ID NO 45
<211> LENGTH: 19
<212> TYPE: RNA
<213> ORGANISM: homo sapiens

<400> SEQUENCE: 45
uugaccuccg gcuugagcg                                               19

<210> SEQ ID NO 46
<211> LENGTH: 20
<212> TYPE: DNA
<213> ORGANISM: artificial
<220> FEATURE:
<223> OTHER INFORMATION: claudin-5 forward primer sequence

<400> SEQUENCE: 46
tttcttctat gcgcagttgg                                              20

<210> SEQ ID NO 47
<211> LENGTH: 20
<212> TYPE: DNA
<213> ORGANISM: artificial
<220> FEATURE:
<223> OTHER INFORMATION: claudin-5 reverse primer sequence

<400> SEQUENCE: 47
gcagtttggt gcctacttca                                              20

<210> SEQ ID NO 48
<211> LENGTH: 22
<212> TYPE: DNA
<213> ORGANISM: artificial
```

```
<220> FEATURE:
<223> OTHER INFORMATION: beta-actin forward primer sequence

<400> SEQUENCE: 48
tcacccacac tgtgcccatc ta                                            22

<210> SEQ ID NO 49
<211> LENGTH: 21
<212> TYPE: DNA
<213> ORGANISM: artificial
<220> FEATURE:
<223> OTHER INFORMATION: beta-actin reverse primer sequence

<400> SEQUENCE: 49
cagcggaacc gctcattgcc a                                             21
```